US012577249B2

(12) United States Patent
Ahn et al.

(10) Patent No.: US 12,577,249 B2
(45) Date of Patent: Mar. 17, 2026

(54) GCN2 AND PERK KINASE INHIBITORS AND METHODS OF USE THEREOF

(71) Applicant: Deciphera Pharmaceuticals, LLC, Waltham, MA (US)

(72) Inventors: Yu Mi Ahn, Waltham, MA (US); Gada Al-Ani, Waltham, MA (US); Daniel L. Flynn, Waltham, MA (US); Salim Javed, Waltham, MA (US); Patrick Kearney, Waltham, MA (US); Bertrand LeBourdonnec, Waltham, MA (US); Kristen Stoltz, Waltham, MA (US); Jeffery Zwicker, Waltham, MA (US)

(73) Assignee: Deciphera Pharmaceuticals, LLC, Waltham, MA (US)

( * ) Notice: Subject to any disclaimer, the term of this patent is extended or adjusted under 35 U.S.C. 154(b) by 38 days.

(21) Appl. No.: 18/073,886

(22) Filed: Dec. 2, 2022

(65) Prior Publication Data

US 2023/0382915 A1 Nov. 30, 2023

Related U.S. Application Data

(60) Provisional application No. 63/348,557, filed on Jun. 3, 2022, provisional application No. 63/285,833, filed on Dec. 3, 2021.

(51) Int. Cl.

| | |
|---|---|
| ***C07D 487/04*** | (2006.01) |
| ***A61K 45/06*** | (2006.01) |
| ***A61P 35/00*** | (2006.01) |
| ***C07D 491/048*** | (2006.01) |
| ***C07D 495/04*** | (2006.01) |

(52) U.S. Cl.

CPC ............ *C07D 487/04* (2013.01); *A61K 45/06* (2013.01); *A61P 35/00* (2018.01); *C07D 491/048* (2013.01); *C07D 495/04* (2013.01)

(58) Field of Classification Search

CPC ........ C07D 487/04; A61P 35/00; A61K 45/06
See application file for complete search history.

(56) References Cited

U.S. PATENT DOCUMENTS

| | | | |
|---|---|---|---|
| 6,001,839 A | 12/1999 | Calderwood et al. | |
| 6,391,885 B1 | 5/2002 | Piazza et al. | |
| 6,660,744 B1 | 12/2003 | Hirst et al. | |
| 6,713,474 B2 | 3/2004 | Hirst et al. | |
| 6,921,763 B2 | 7/2005 | Hirst et al. | |
| 7,071,199 B1 | 7/2006 | Hirst et al. | |
| 7,144,911 B2 | 12/2006 | Flynn et al. | |
| 7,202,257 B2 | 4/2007 | Flynn et al. | |
| 7,202,363 B2 | 4/2007 | Betschmann et al. | |
| 7,276,506 B2 | 10/2007 | Waer et al. | |
| 7,279,576 B2 | 10/2007 | Flynn et al. | |
| 7,342,037 B2 | 3/2008 | Flynn et al. | |
| 7,423,038 B2 | 9/2008 | Ren et al. | |
| 7,446,112 B2 | 11/2008 | Grootenhuis et al. | |
| 7,449,582 B2 | 11/2008 | Ding et al. | |
| 7,501,513 B2 | 3/2009 | Waer et al. | |
| 7,531,566 B2 | 5/2009 | Flynn et al. | |
| 7,592,352 B2 | 9/2009 | Miyazaki | |
| 7,662,819 B2 | 2/2010 | Chisholm et al. | |
| 7,666,895 B2 | 2/2010 | Flynn et al. | |
| 7,678,792 B2 | 3/2010 | Chianelli et al. | |
| 7,696,213 B2 | 4/2010 | Cheng et al. | |
| 7,737,283 B2 | 6/2010 | Flynn et al. | |
| 7,790,756 B2 | 9/2010 | Flynn et al. | |
| 7,829,570 B2 | 11/2010 | Hirst et al. | |
| 7,863,444 B2 * | 1/2011 | Calderwood ........ | C07D 487/04 544/280 |
| 7,893,066 B2 | 2/2011 | Koltun et al. | |
| 7,897,762 B2 | 3/2011 | Flynn et al. | |
| 8,143,293 B2 | 3/2012 | Flynn et al. | |
| 8,143,394 B2 | 3/2012 | Watkins et al. | |
| 8,163,756 B2 | 4/2012 | Flynn et al. | |
| 8,188,113 B2 | 5/2012 | Flynn et al. | |
| 8,278,331 B2 | 10/2012 | Flynn et al. | |
| 8,461,179 B1 | 6/2013 | Flynn et al. | |
| 8,486,951 B2 | 7/2013 | Flynn et al. | |
| 8,536,187 B2 | 9/2013 | Canales et al. | |
| 8,569,319 B2 | 10/2013 | Flynn et al. | |
| 8,586,565 B2 | 11/2013 | Flynn et al. | |
| 8,637,549 B2 | 1/2014 | Engelhardt et al. | |
| 8,637,672 B2 | 1/2014 | Flynn et al. | |
| 8,697,709 B2 | 4/2014 | Dar et al. | |
| 8,741,911 B2 | 6/2014 | Allgeier et al. | |

(Continued)

FOREIGN PATENT DOCUMENTS

| | | |
|---|---|---|
| CN | 102746241 B | 11/2014 |
| CN | 109721531 A | 5/2019 |

(Continued)

OTHER PUBLICATIONS

Liu et al. Ligand-independent Dimerization Activates the Stress Response Kinases IRE1 and PERK in the Lumen of the Endoplasmic Reticulum, JBC, Aug. 2000, pp. 24881-24885. (Year: 2000).*

(Continued)

*Primary Examiner* — Sarah Pihonak
*Assistant Examiner* — Mikhail O'Donnel Robinson
(74) *Attorney, Agent, or Firm* — Goodwin Procter LLP

(57) ABSTRACT

Described herein are compounds that are inhibitors of GCN2 kinase or PERK kinase, and methods of treating diseases, including diseases associated with GCN2 kinase or PERK kinase, with said compounds.

28 Claims, 15 Drawing Sheets

Specification includes a Sequence Listing.

(56) References Cited

U.S. PATENT DOCUMENTS

| | | | |
|---|---|---|---|
| 8,921,565 | B2 | 12/2014 | Flynn et al. |
| 8,940,756 | B2 | 1/2015 | Flynn et al. |
| 8,940,893 | B2 | 1/2015 | Bosanac et al. |
| 8,980,899 | B2 | 3/2015 | Korennykh et al. |
| 9,012,635 | B2 | 4/2015 | Flynn et al. |
| 9,133,183 | B2 | 9/2015 | Flynn et al. |
| 9,181,223 | B2 | 11/2015 | Kaufman et al. |
| 9,187,474 | B2 | 11/2015 | Flynn et al. |
| 9,193,719 | B2 | 11/2015 | Flynn et al. |
| 9,309,224 | B2 | 4/2016 | Flynn et al. |
| 9,334,267 | B2 | 5/2016 | Flynn et al. |
| 9,376,438 | B2 | 6/2016 | Goldstein et al. |
| 9,382,228 | B2 | 7/2016 | Flynn et al. |
| 9,387,202 | B2 | 7/2016 | Flynn et al. |
| 9,457,019 | B2 | 10/2016 | Flynn et al. |
| 10,399,988 | B2 | 9/2019 | Yoon et al. |
| 10,544,104 | B2 | 1/2020 | Van Voorhis et al. |
| 10,561,660 | B2 | 2/2020 | Bindi et al. |
| 10,745,379 | B2 | 8/2020 | Vacca et al. |
| 10,966,966 | B2 | 4/2021 | Soto et al. |
| 11,103,507 | B2 | 8/2021 | Flynn et al. |
| RE48,731 | E | 9/2021 | Flynn et al. |
| 11,185,535 | B2 | 11/2021 | Kaufman et al. |
| 11,266,635 | B2 | 3/2022 | Soto et al. |
| 11,344,536 | B1 | 5/2022 | Soto et al. |
| 11,395,818 | B2 | 7/2022 | Kaufman et al. |
| 11,426,390 | B2 | 8/2022 | Soto et al. |
| 11,433,056 | B1 | 9/2022 | Soto et al. |
| 11,518,758 | B2 | 12/2022 | Flynn et al. |
| 11,529,336 | B2 | 12/2022 | Soto et al. |
| 11,530,206 | B2 | 12/2022 | Flynn et al. |
| 11,534,432 | B2 | 12/2022 | Soto et al. |
| 11,576,903 | B2 | 2/2023 | Kaufman et al. |
| 11,576,904 | B2 | 2/2023 | Soto et al. |
| 11,590,134 | B2 | 2/2023 | Flynn et al. |
| 11,612,591 | B2 | 3/2023 | Kaufman et al. |
| 11,679,110 | B2 | 6/2023 | Flynn et al. |
| 2003/0199525 | A1 | 10/2003 | Hirst et al. |
| 2005/0008640 | A1 | 1/2005 | Waegell et al. |
| 2005/0026944 | A1 | 2/2005 | Betschmann et al. |
| 2006/0025383 | A1 | 2/2006 | Wishart et al. |
| 2007/0004721 | A1 | 1/2007 | Waer et al. |
| 2007/0054916 | A1 | 3/2007 | Patel et al. |
| 2007/0060601 | A1 | 3/2007 | Arrington et al. |
| 2009/0306107 | A1 | 12/2009 | Perez et al. |
| 2009/0318456 | A1 | 12/2009 | Herdewijn et al. |
| 2011/0136766 | A1 | 6/2011 | Zhuang et al. |
| 2011/0313156 | A1 | 12/2011 | Engelhardt et al. |
| 2013/0116263 | A1 | 5/2013 | Campbell et al. |
| 2013/0267526 | A1 | 10/2013 | Chen et al. |
| 2014/0038991 | A1 | 2/2014 | Yu et al. |
| 2014/0163026 | A1 | 6/2014 | Campbell et al. |
| 2015/0031693 | A1 | 1/2015 | Mckew et al. |
| 2016/0045503 | A1 | 2/2016 | Goldstein et al. |
| 2016/0257676 | A1 | 9/2016 | Zhang et al. |
| 2020/0108075 | A1 | 4/2020 | Liang et al. |
| 2020/0157079 | A1 | 5/2020 | Vacca et al. |
| 2020/0352920 | A1 | 11/2020 | Flynn et al. |
| 2021/0128559 | A1 | 5/2021 | Xu et al. |
| 2021/0145805 | A1 | 5/2021 | Flynn et al. |
| 2021/0261544 | A1 | 8/2021 | Deng et al. |
| 2022/0047573 | A1 | 2/2022 | Flynn et al. |
| 2022/0184050 | A1 | 6/2022 | Flynn |
| 2022/0184054 | A1 | 6/2022 | Flynn |
| 2022/0184077 | A1 | 6/2022 | Flynn |
| 2022/0184092 | A1 | 6/2022 | Flynn |
| 2022/0184093 | A1 | 6/2022 | Flynn |
| 2022/0193083 | A1 | 6/2022 | Flynn |
| 2022/0274934 | A1 | 9/2022 | Flynn et al. |
| 2022/0370423 | A1 | 11/2022 | Flynn et al. |
| 2022/0370424 | A1 | 11/2022 | Flynn et al. |
| 2022/0370426 | A1 | 11/2022 | Soto et al. |
| 2023/0039712 | A1 | 2/2023 | Flynn et al. |
| 2023/0047915 | A1 | 2/2023 | Flynn et al. |
| 2023/0145926 | A1 | 5/2023 | Soto et al. |
| 2023/0201175 | A1 | 6/2023 | Kaufman et al. |
| 2023/0201176 | A1 | 6/2023 | Kaufman et al. |

FOREIGN PATENT DOCUMENTS

| | | | |
|---|---|---|---|
| DE | 4038932 | A1 | 6/1992 |
| EP | 1836174 | B1 | 2/2013 |
| EP | 3929195 | A1 | 12/2021 |
| WO | WO-98/41525 | A1 | 9/1998 |
| WO | WO-2000017202 | A1 | 3/2000 |
| WO | WO-2001019829 | A3 | 9/2001 |
| WO | WO-2001072751 | A1 | 10/2001 |
| WO | WO-2006/039718 | A2 | 4/2006 |
| WO | WO-2008043087 | A2 | 4/2008 |
| WO | WO-2008077649 | A1 | 7/2008 |
| WO | WO-2009126123 | A1 | 10/2009 |
| WO | WO-2016023401 | A1 | 2/2016 |
| WO | WO-2016075224 | A1 | 5/2016 |
| WO | WO-2017220477 | A1 | 12/2017 |
| WO | WO-2018106459 | A1 | 6/2018 |
| WO | WO-2020117635 | A1 | 6/2020 |
| WO | WO-2020142612 | A1 | 7/2020 |
| WO | WO-2020147097 | A1 | 7/2020 |
| WO | WO-2020172093 | A1 | 8/2020 |
| WO | WO-2020177729 | A1 | 9/2020 |
| WO | WO-2020210828 | A1 | 10/2020 |
| WO | WO-2020232401 | A1 | 11/2020 |
| WO | WO-2020232403 | A1 | 11/2020 |
| WO | WO-2020243376 | A1 | 12/2020 |
| WO | WO-2020252165 | A1 | 12/2020 |
| WO | WO-2021145521 | A1 | 7/2021 |
| WO | WO-2021165346 | A1 | 8/2021 |
| WO | WO-2022109001 | A1 | 5/2022 |

OTHER PUBLICATIONS

U.S. Appl. No. 11/963,740, filed Dec. 21, 2007, Patented, U.S. Pat. No. 8,163,756.
U.S. Appl. No. 11/870,388, filed Oct. 10, 2007, Patented, U.S. Pat. No. 7,790,756.
U.S. Appl. No. 12/829,561, filed Jul. 2, 2010, Patented, U.S. Pat. No. 8,586,565.
U.S. Appl. No. 11/854,354, filed Sep. 12, 2007, Patented, U.S. Pat. No. 8,188,113.
U.S. Appl. No. 10/746,460, filed Dec. 24, 2003, Patented, U.S. Pat. No. 7,144,911.
U.S. Appl. No. 10/886,329, filed Jul. 6, 2004, Patented, U.S. Pat. No. 7,202,257.
U.S. Appl. No. 11/450,840, filed Jun. 9, 2006, Patented, U.S. Pat. No. 7,342,037.
U.S. Appl. No. 11/336,708, filed Jan. 20, 2006, Patented, U.S. Pat. No. 7,531,566.
U.S. Appl. No. 11/450,850, filed Jun. 9, 2006, Patented, U.S. Pat. No. 7,666,895.
U.S. Appl. No. 10/746,607, filed Dec. 24, 2003, Patented, U.S. Pat. No. 7,279,576.
U.S. Appl. No. 11/854,293, filed Sep. 12, 2007, Patented, U.S. Pat. No. 7,897,762.
U.S. Appl. No. 12/105,408, filed Apr. 18, 2008, Patented, U.S. Pat. No. 8,143,293.
U.S. Appl. No. 13/590,955, filed Aug. 21, 2012, Patented, U.S. Pat. No. 8,486,951.
U.S. Appl. No. 11/450,849, filed Jun. 9, 2006, Patented, U.S. Pat. No. 7,737,283.
U.S. Appl. No. 13/785,575, filed Mar. 5, 2013, Patented, U.S. Pat. No. 8,741,911.
U.S. Appl. No. 12/608,578, filed Oct. 29, 2009, Patented, U.S. Pat. No. 8,278,331.
U.S. Appl. No. 13/098,247, filed Apr. 29, 2011, Patented, U.S. Pat. No. 8,569,319.
U.S. Appl. No. 13/559,170, filed Jul. 26, 2012, Patented, U.S. Pat. No. 8,637,672.
U.S. Appl. No. 14/214,134, filed Mar. 14, 2014, Patented, U.S. Pat. No. 9,133,183.

(56) References Cited

OTHER PUBLICATIONS

U.S. Appl. No. 14/383,803, filed Mar. 5, 2013, Patented, U.S. Pat. No. 9,187,474.
U.S. Appl. No. 13/491,394, filed Jun. 7, 2012, Patented, U.S. Pat. No. 8,461,179.
U.S. Appl. No. 13/801,753, filed Mar. 13, 2013, Patented, U.S. Pat. No. 8,940,756.
U.S. Appl. No. 16/387,315, filed Apr. 17, 2019, Patented, U.S. Pat. No. Re. 48,731.
U.S. Appl. No. 14/214,127, filed Mar. 14, 2014, Patented, U.S. Pat. No. 9,012,635.
U.S. Appl. No. 13/683,277, filed Nov. 21, 2012, Patented, U.S. Pat. No. 8,921,565.
U.S. Appl. No. 14/549,125, filed Nov. 20, 2014, Patented, U.S. Pat. No. 9,387,202.
U.S. Appl. No. 14/214,160, filed Mar. 14, 2014, Patented, U.S. Pat. No. 9,193,719.
U.S. Appl. No. 14/214,171, filed Mar. 14, 2014, Patented, U.S. Pat. No. 9,181,223.
U.S. Appl. No. 14/214,185, filed Mar. 14, 2014, Patented, U.S. Pat. No. 9,382,228.
U.S. Appl. No. 14/214,179, filed Mar. 14. 2014, Patented, U.S. Pat. No. 9,309,224.
U.S. Appl. No. 14/383,799, filed Mar. 5, 2013, Patented, U.S. Pat. No. 9,334,267.
U.S. Appl. No. 14/535,900, filed Nov. 7, 2014, Patented, U.S. Pat. No. 9,457,019.
U.S. Appl. No. 17/845,275, filed Jun. 21, 2022, Pending, US 2022-0370423 A1.
U.S. Appl. No. 17/845,278, filed Jun. 21, 2022, Pending, US 2022-0370424 A1.
U.S. Appl. No. 16/943,821, filed Jul. 30, 2020, Pending, US 2021-0145805 A1.
U.S. Appl. No. 16/943,871, filed Jul. 30, 2020, Pending, US 2020-0352920 A1.
U.S. Appl. No. 16/725,282, filed Dec. 23, 2019, Patented, U.S. Pat. No. 11,103,507.
U.S. Appl. No. 17/358,137, filed Jun. 25, 2021, Patented, U.S. Pat. No. 11,679,110.
U.S. Appl. No. 18/140,942, filed Apr. 28, 2023, Pending.
U.S. Appl. No. 16/870,384, filed May 8, 2020, Patented, U.S. Pat. No. 11,530,206.
U.S. Appl. No. 17/833,272, filed Jun. 6, 2022, Pending, US 2023-0039712 A1.
U.S. Appl. No. 16/870,418, filed May 8, 2020, Patented, U.S. Pat. No. 11,518,758.
U.S. Appl. No. 17/832,224, filed Jun. 3J, 2022, Pending, US 2023-0047915 A1.
U.S. Appl. No. 16/902,989, filed Jun. 16, 2020, Patented, U.S. Pat. No. 11,590,134.
U.S. Appl. No. 18/152,993, filed Jan. 11, 2023, Pending.
U.S. Appl. No. 16/991,644, filed Aug. 12, 2020, Pending, US 2022-0047573 A1.
U.S. Appl. No. 17/028,640, filed Sep. 22, 2020, Patented, U.S. Pat. No. 10,966,966.
U.S. Appl. No. 17/180,218, filed Feb. 19, 2021, Patented, U.S. Pat. No. 11,266,635.
U.S. Appl. No. 17/583,977, filed Jan. 25, 2022, Patented, U.S. Pat. No. 11,426,390.
U.S. Appl. No. 17/583,985, filed Jan. 25, 2022, Patented, U.S. Pat. No. 11,344,536.
U.S. Appl. No. 17/727,307, filed Apr. 22, 2022, Patented, U.S. Pat. No. 11,534,432.
U.S. Appl. No. 17/735,678, filed May 3, 2022, Patented, U.S. Pat. No. 11,529,336.
U.S. Appl. No. 17/735,682, filed May 3, 2022, Patented, U.S. Pat. No. 11,576,904.
U.S. Appl. No. 17/735,862, filed May 3, 2022, Patented, U.S. Pat. No. 11,433,056.
U.S. Appl. No. 18/091,743, filed Dec. 30, 2022, Pending, US 2023-0145926 A1.
U.S. Appl. No. 17/869,108, filed Jul. 20, 2022, Pending, US 2022-0370426 A1.
U.S. Appl. No. 17/180,234, filed Feb. 19, 2021, Patented, U.S. Pat. No. 11,185,535.
U.S. Appl. No. 17/504,133, filed Oct. 18, 2021, Patented, U.S. Pat. No. 11,576,903.
U.S. Appl. No. 18/314,348, filed May 9, 2023, Pending.
U.S. Appl. No. 17/180,241, filed Feb. 19, 2021, Patented, U.S. Pat. No. 11,395,818.
U.S. Appl. No. 17/735,820, filed May 3, 2022, Patented, U.S. Pat. No. 11,612,591.
U.S. Appl. No. 18/148,766, filed Dec. 30, 2022, Pending, US 2023-0201175 A1.
U.S. Appl. No. 18/178,789, filed Mar. 6, 2023, Pending, US 2023-0201176 A1.
U.S. Appl. No. 17/528,478, filed Nov. 17, 2021, Pending, US 2022-0274934 A1.
U.S. Appl. No. 17/534,795, filed Nov. 24, 2021, Pending, US 2022-0193083 A1.
U.S. Appl. No. 17/534,762, filed Nov. 24, 2021, Pending, US 2022-0184092 A1.
U.S. Appl. No. 17/534,764, filed Nov. 24, 2021, Pending, US 2022-0184054 A1.
U.S. Appl. No. 17/534,768, filed Nov. 24, 2021, Pending, US 2022-0184050 A1.
U.S. Appl. No. 17/534,769, filed Nov. 24, 2021, Pending, US 2022-0184077 A1.
U.S. Appl. No. 17/534,771, filed Nov. 24, 2021, Pending, US 2022-0184093 A1.
U.S. Appl. No. 18/078,269, filed Dec. 9, 2022, Pending.
U.S. Appl. No. 18/078,271, filed Dec. 9, 2022, Pending.
U.S. Appl. No. 18/073,721, filed Dec. 2, 2022, Pending.
U.S. Appl. No. 17/938,353, filed Oct. 6, 2022, Pending.
Alasiri, G. et al., "Reciprocal regulation between GCN2 (eIF2AK4) and PERK (eIF2AK3) through the JNK-FOXO3 axis to modulate cancer drug resistance and clonal survival", Molecular and Cellular Endocrinology, 2020, 515, 15 pages.
Alberga, Domenico et al. A New Approach for Drug Target and Bioactivity Prediction: The Multifingerprint Similarity Search Algorithm (MuSSeL); Journal of Chemical Information and Modeling (2019), 59(1), 586-596.
Axten, J. M. et al., "Discovery of 7-Methyl-5-(1 {[3-(trifluoromethyl)phenyl]}-2,3-dihydro-1H-indol-5-yl)-7H-pyrrolo[2,3-d]pyrimidin-4-amine(GSK2606414), a Potent and Selective First-in-Class Inhibitor of Protein Kinase R (PKR)-like Endoplasmic Reticulum Kinase (PERK)", J. Med. Chem., 2012, 25 pages.
Axten, J. M. et al., "Discovery of GSK2656157: An Optimized PERK Inhibitors Selected for Preclinical Development", ACS Medicinal Chemistry Letters, 2013, 4, pp. 964-968.
Fujimoto, J. et al., "Identification of novel, potent and orally available GCN2 inhibitors with type I half binding mode", ACS Medicinal Chemistry Letters, Sep. 19, 2019, 50 pages.
Giglio, P. et al., "PKR and GCN2 stress kinases promote an ER stress-independent eIF2α phosphorylation responsible for calreticulin exposure in melanoma cells", Oncoimmunology, 2018, vol. 7, e1466765, 14 pages.
Hamanaka, R. B. et al., "PERK and GCN2 Contribute to eIF2α Phosphorylation and Cell Cycle Arrest after Activation of the Unfolded Protein Response Pathway", Molecular Biology of the Cell, vol. 16, pp. 5493-5501, Dec. 2005.
International Search Report and Written Opinion of PCT/US2021/059678 dated Mar. 15, 2022, 15 pages.
International Search Report and Written Opinion of PCT/US2022/051717 dated Mar. 31, 2023, 11 pages.
Lehman, S. L., "The Role of the Integrated Stress Response Kinase Gon2 in Cell Regulation and Tumorigenesis", Univ. of Pennsylvania Scholarly Commons, 2015, 102 pages.
Lin, Songwen, et al. 2-Amino-4-methylquinazoline Derivatives as Highly Potent Phosphatidylinositol 3-Kinase Inhibitors for Cancer Treatment; Journal of Medicinal Chemistry (2018), 61(14), 6087-6109.

(56) References Cited

OTHER PUBLICATIONS

Lin, Songwen, et al. Discovery of 4-Methylquinazoline Based PI3K Inhibitors for the Potential Treatment of Idiopathic Pulmonary Fibrosis; Journal of Medicinal Chemistry (2019), 62(19), 8873-8879.
Smith, A. L. et al., "Discovery of 1H-Pyrazol-3(2H)-ones as Potent and Selective Inhibitors of Protein Kinase R-like Endoplasmic Reticulum Kinase (PERK)", Journal of Medicinal Chemistry, 2015, 58, pp. 1426-1441.
International Preliminary Report on Patentability of PCT/US2022/051717 dated Jun. 13, 2024, 19 pages.
Chen, C. et al., Multifaceted role of GCN2 in tumor adaptation and therapeutic targeting, Translational Oncology, 49 (2024), 17 pages.

* cited by examiner

| Dose (mg/kg) | Time point (h) | Drug levels in plasma (ng/ml) | % Inhibition of ATF4 |
|---|---|---|---|
| 50 | 2 | 32603 | 88 |
| 50 | 6 | 28141 | 91 |
| 50 | 10 | 27880 | 87 |
| 25 | 2 | 11443 | 79 |
| 25 | 6 | 24759 | 93 |
| 25 | 10 | 2210 | 57 |

| Dose (mg/kg) | Time point (hr) | Compound 2 plasma level (ng/ml) |
|---|---|---|
| 10 | 2 | 12041 |
| 10 | 6 | 4797 |
| 10 | 10 | 2759 |
| 5 | 2 | 9497 |
| 5 | 6 | 842 |
| 5 | 10 | 470 |
| 1 | 2 | 812 |
| 1 | 6 | 362 |
| 1 | 10 | 199 |

SEQUENCE LISTING

```
Sequence total quantity: 3
SEQ ID NO: 1           moltype = AA  length = 1894
FEATURE                Location/Qualifiers
source                 1..1894
                       mol_type = protein
                       organism = synthetic construct
SEQUENCE: 1
MAPILGYWKI KGLVQPTRLL LEYLEEKYEE HLYERDEGDK WRNKKFELGL EFPNLPYYID  60
GDVKLTQSMA IIRYIADKHN MLGGCPKERA EISMLEGAVL DIRYGVSRIA YSKDFETLKV  120
DFLSKLPEML KMFEDRLCHK TYLNGDHVTH PDFMLYDALD VVLYMDPMCL DAFPKLVCFK  180
KRIEAIPQID KYLKSSKYIA WPLQGWQATF GGGDHPPKSD LEVLFQGPLG AMGSGIQRPT  240
STSSLVMAGG RGAPGRGRDE PPESYPQRQD HELQALEAIY GADFQDLRPD ACGPVKEPPE  300
INLVLYPQGL TGEEVYVKVD LRVKCPPTYP DVVPEIELKN AKGLSNESVN LLKSRLEELA  360
KKHCGEVMIF ELAYHVQSFL SEHNKPPPKS FHEEMLERRA QEEQQRLLEA KRKEEQEQRE  420
ILHEIQRRKE EIKEEKKRKE MAKQERLEIA SLSNQDHTSK KDPGGHRTAA ILHGGSPDFV  480
GNGKHRANSS GRSRRERQYS VCNSEDSPGS CEILYFNMGS PDQLMVHKGK CIGDEQLGKL  540
VYNALETATG GFVLLYEWVL QWQKKMGPFL TSQEKEKIDK CKKQIQGTET EFNSLVKLSH  600
PNVVRYLAMN LKEQDDSIVV DILVEHISGV SLAAHLSHSG PIPVHQLRRY TAQLLSGLDY  660
LHSNSVVHKV LSASNVLVDA EGTVKITDYS ISKRLADICK EDVFEQTRVR FSDNALPYKT  720
GKKGDVWRLG LLLLSLSQGQ ECGEYPVTIP SDLPADFQDF LKKCVCLDDK ERWSPQQLLK  780
HSFINPQPKM PLVEQSPEDS GGQDYVETVI PSNRLPSAAF FSETQRQFSR YFIEFEELQL  840
LGKGAFGAVI KVQNKLDGCC YAVKRIPINP ASRQFRRIKG EVTLLSRLHH ENIVRYYNAW  900
IERHERPAGP GTPPPDSGPL AKDDRAARGQ PASDTDGLDS VEAAAPPPIL SSSVEWSTSG  960
ERSASARFPA TGPGSSDDED DDEDEHGGVF SQSFLPASDS ESDIIFDNED ENSKSQNQDE  1020
DCNEKNGCHE SEPSVTTEAV HYLYIQMEYC EKSTLRDTID QGLYRDTVRL WRLFREILDG  1080
LAYIHEKGMI HRDLKPVNIF LDSDDHVKIG DFGLATDHLA FSADSKQDDQ TGDLIKSDPS  1140
GHLTGMVGTA LYVSPEVQGS TKSAYNQKVD LFSLGIIFFE MSYHPMVTAS ERIFVLNQLR  1200
DPTSPKFPED FDDGEHAKQK SVISWLLNHD PAKRPTATEL LKSELLPPPQ MEESELHEVL  1260
HHTLTNVDGK AYRTMMAQIF SQRISPAIDY TYDSDILKGN FSIRTAKMQQ HVCETIIRIF  1320
KRHGAVQLCT PLLLPRNRQI YEHNEAALFM DHSGMLVMLP FDLRIPFARY VARNNILNLK  1380
RYCIERVFRP RKLDRFHPKE LLECAFDIVT STTNSFLPTA EIIYTIYEII QEFPALQERN  1440
YSIYLNHTML LKAILLHCGI PEDKLSQVYI ILYDAVTEKL TRREVEAKFC NLSLSSNSLC  1500
RLYKFIEQKG DLQDLMPTIN SLIKQKTGIA QLVKYGLKDL EEVVGLLKKL GIKLQVLINL  1560
GLVYKVQQHN GIIFQFVAFI KRRQRAVPEI LAAGGRYDLL IPQFRGPQAL GPVPTAIGVS  1620
IAIDKISAAV LNMEESVTIS SCDLLVVSVG QMSMSRAINL TQKLWTAGIT AEIMYDWSQS  1680
QEELQEYCRH HEITYVALVS DKEGSHVKVK SFEKERQTEK RVLETELVDH VLQKLRTKVT  1740
DERNGREASD NLAVQNLKGS FSNASGLFEI HGATVVPIVS VLAPEKLSAS TRRRYETQVQ  1800
TRLQTSLANL HQKSSEIEIL AVDLPKETIL QFLSLEWDAD EQAFNTTVKQ LLSRLPKQRY  1860
LKLVCDEIYN IKVEKKVSVL FLYSYRDDYY RILF                              1894

SEQ ID NO: 2           moltype = AA  length = 779
FEATURE                Location/Qualifiers
source                 1..779
```

-continued

```
                         mol_type = protein
                         organism = synthetic construct
SEQUENCE: 2
MSPILGYWKI KGLVQPTRLL LEYLEEKYEE HLYERDEGDK WRNKKFELGL EFPNLPYYID  60
GDVKLTQSMA IIRYIADKHN MLGGCPKERA EISMLEGAVL DIRYGVSRIA YSKDFETLKV  120
DFLSKLPEML KMFEDRLCHK TYLNGDHVTH PDFMLYDALD VVLYMDPMCL DAFPKLVCFK  180
KRIEAIPQID KYLKSSKYIA WPLQGWQATF GGGDHPPKSD LVPRGSKYDS VSGEANDSSW  240
NDIKNSGYIS RYLTDFEPIQ CLGRGGFGVV FEAKNKVDDC NYAIKRIRLP NRELAREKVM  300
REVKALAKLE HPGIVRYFNA WLEAPPEKWQ EKMDEIWLKD ESTDWPLSSP SPMDAPSVKI  360
RRMDPFSTKE HIEIIAPSPQ RSRSFSVGIS CDQTSSSESQ FSPLEFSGMD HEDISESVDA  420
AYNLQDSCLT DCDVEDGTMD GNDEGHSFEL CPSEASPYVR SRERTSSSIV FEDSGCDNAS  480
SKEEPKTNRL HIGNHCANKL TAFKPTSSKS SSEATLSISP PRPTTLSLDL TKNTTEKLQP  540
SSPKVYLYIQ MQLCRKENLK DWMNGRCTIE ERERSVCLHI FLQIAEAVEF LHSKGLMHRD  600
LKPSNIFFTM DDVVKVGDFG LVTAMDQDEE EQTVLTPMPA YARHTGQVGT KLYMSPEQIH  660
GNSYSHKVDI FSLGLILFEL LYPFSTQMER VRTLTDVRNL KFPPLFTQKY PCEYVMVQDM  720
LSPSPMERPE AINIIENAVF EDLDFPGKTV LRQRSRSLSS SGTKHSRQSN NSHSPLPSN   779

SEQ ID NO: 3             moltype = AA  length = 10
FEATURE                  Location/Qualifiers
source                   1..10
                         mol_type = protein
                         organism = synthetic construct
MOD_RES                  1
                         note = pyro-Glutamic acid
MOD_RES                  6
                         note = O-t-butyl-D-Serine
MOD_RES                  10
                         note = Amidated azaglycine
SEQUENCE: 3
EHWSYSLRPG                                                          10
```

GCN2 AND PERK KINASE INHIBITORS AND METHODS OF USE THEREOF

CROSS REFERENCE TO RELATED APPLICATIONS

This application claims priority to U.S. Provisional Application No. 63/285,833 filed Dec. 3, 2021, and U.S. Provisional Application No. 63/348,557 filed Jun. 3, 2022, the contents of each of which are incorporated herein by reference in their entireties.

REFERENCE TO A SEQUENCE LISTING XML

This application contains a Sequence Listing which has been submitted electronically in XML format. The Sequence Listing XML is incorporated herein by reference. Said XML file, created on Jun. 15, 2023, is named DCP-106_SL.xml and is 7,457 bytes in size.

BACKGROUND

Cancer cells need a continuous supply of nutrients to maintain their abnormal growth and rapid division. As part of these nutrients, amino acids are essential to support the high metabolic demands of tumor cells.

GCN2 is a serine/threonine protein kinase, one of the eukaryotic initiation factor 2a (eIF2α) kinases that are master regulators in the integrated stress response (ISR). The ISR is essential for maintaining cellular homeostasis under a wide range of stressors and is activated when cells adapt to stress conditions such as hypoxia and amino acid deprivation. The ISR is regulated by phosphorylation and activation of eIF2α kinases, including GCN2, that act as early responders to disturbances in cellular homeostasis. In addition to GCN2, there are three other eIF2α kinases family including PKR-like ER kinase (PERK), double-stranded RNA-dependent protein kinase (PKR), and heme-regulated eIF2α kinase (HRI). All four eIF2α kinases share extensive homology in their kinase catalytic domains but possess distinct regulatory domains. Each of the IF2α kinases responds to distinct environmental and physiological stresses, which reflect their unique regulatory mechanisms. PERK kinase is activated under stress conditions including ATP depletion and the unfolded protein response, and like GCN2, PERK kinase activation leads to up-regulation of the key ISR transcription factor ATF4.

Under conditions of essential amino-acid limitation or other stressors (UV irradiation, redox stress or proteasome inhibition), GCN2 phosphorylates eIF2α, which inhibits the formation of a new ternary complex and hence inhibition of mRNA translation initiation. While decreasing global mRNA translation, in tumor cells eIF2α phosphorylation also increases the translation of the ISR transcription factor ATF4, which increases the expression of many stress response genes including genes dedicated to providing amino acids to the tumor cell: i.e., amino acid synthesis enzymes and transporters that mediate influx of amino acids into the tumor cell. ATF4 is over-expressed in human solid and liquid tumors suggesting an important function in tumor progression.

Asparagine is an important amino acid involved in several biosynthetic pathways that significantly influence carcinogenesis and tumor biology. All cells need asparagine for their protein synthesis and growth. Normal cells will obtain most of their asparagine requirements through internal synthesis. Compared to normal cells, cancer cells require elevated amounts of asparagine to grow and proliferate, cannot produce that required amount themselves, and must rely on circulating asparagine in order to survive. Asparagine Synthetase (ASNS) catalyzes the synthesis of asparagine from aspartate and glutamine. L-asparaginase (ASNase) removes circulating asparagine, thereby depriving cancer cells of a key nutrient and causing them to die. The use of L-asparaginase, the first example of anti-cancer treatment targeting a tumor-specific metabolic feature, is a well-established treatment in pediatric acute lymphoblastic leukemia (ALL), but toxicity has limited its use beyond this patient population. The particularly low-level expression of ASNS in numerous ALL cell lines, as compared to that of normal cells, makes asparagine depletion an effective method of treatment due to the cells' unusual dependency on circulating serum asparagine as a necessary nutrition for growth. A poor response to asparaginase is associated with increased relapse risk. Other hematological and solid cancers express low levels of ASNS and, therefore, should also be asparagine auxotroph and asparaginase sensitive. Conversely, in some cancer types ASNS is overexpressed, promoting cell proliferation, chemoresistance, and a metastatic behavior. In case of asparaginase resistant cancers, the effect of blood asparagine depletion through L-asparaginase instead leads to significant ASNS overexpression to compensate, effectively nullifying the effect of the chemotherapy drug. Numerous studies have shown that ASNS is at the center of the cell response to amino acid deprivation and other forms of cellular stress. Through transcriptional regulation, the ASNS gene is a target of two signaling pathways aimed at ensuring cell survival. The first, named Amino Acid Response (AAR), is activated by the GCN2 kinase under conditions of imbalanced amino acid availability. The second pathway, named the Unfolded Protein Response (UPR), is activated by the PERK kinase under conditions of increased endoplasmic reticulum stress. The AAR and UPR pathways converge on the phosphorylation of eIF2α, which provokes the attenuation of global protein synthesis and, at the same time, the preferential translation of a selected population of mRNAs, including the transcription factor ATF4. ATF4 is the major factor for ASNS induction, working as a trans-activator through the binding to an enhancer element within ASNS promoter.

GCN2 sensitizes cancer cells with low basal level expression of ASNS to the antileukemic agent L-asparaginase in vitro and in vivo. Treatment with GCN2 inhibitors rendered acute lymphoblastic leukemia cells sensitive to L-asparaginase by preventing the induction of ASNS. GCN2 inhibitors exhibit synergistic antiproliferative effects with L-asparaginase in ASNS-low/deficient cancers. Therefore, combined treatment with GCN2 inhibitors and L-asparaginase shows promise for achieving improved outcomes in acute lymphoblastic leukemia and other types of cancer. Acute lymphoblastic leukemia, acute myeloid leukemia, and pancreatic cancer cells are particularly sensitive to combined treatment with L-asparaginase and GCN2 inhibitors. Previously reported studies demonstrated robust antitumor activities of combined treatment with ASNase and GCN2 inhibitors in acute lymphoblastic leukemia, acute myeloid leukemia, and pancreatic cancer cells compared with the results of single-agent L-asparaginase or GCN2 inhibitor treatment. Thus, GCN2 inhibitors may represent sensitizing agents to L-asparaginase used for treating these tumors. In summary, GCN2 inhibition enhances the sensitivity to L-asparaginase treatment by preventing ASNS induction in cancer cells with low ASNS expression at basal levels.

Inhibition of GCN2 may also be an effective strategy for targeting the tumor microenvironment, including the immune system, including tryptophan-dependent immunosurveillance of tumor cells.

The tumor microenvironment [TME; a series of extracellular components and stromal cells (endothelial cells, cancer-associated fibroblasts, tumor-associated macrophages, tumor-infiltrating T cells) that surround the tumor cells] is characterized by deficiencies in oxygen and key nutrients, such as glucose and amino acids, resulting in an overall immune suppressive environment.

Many tumors evolved to escape immune surveillance by taking advantage of their metabolic flexibility and redirecting nutrients for their own advantage. Stromal cells and myeloid-derived suppressor cells (MDSC) within the tumor create a nutrient-poor environment that inhibits immune function and supports tumor growth.

Elevated catabolism of tryptophan, one of the essential amino acids, driven by overexpression of critical enzymes in tryptophan metabolism [Indoleamine-2,3-dioxygenase (IDO) and tryptophan-2,3-dioxygenase (TDO)] is driven by cells of the tumor microenvironment, leading to an immunosuppressive microenvironment in many types of cancer. Local tryptophan depletion is considered to be a crucial T-cell immunosuppressive mechanism. In T cells, the GCN2 kinase has been identified as a molecular sensor of tryptophan deprivation. GCN2 activation by tryptophan depletion induces apoptosis and mitigates T cell proliferation. GCN2 is a key effector signaling component for IDO/TDO and is considered as a metabolic checkpoint of highly tryptophan-dependent T-cells.

The GCN2 pathway is not only important for tumoral immune escape but also plays an active role in modulating other aspects of the tumor microenvironment. GCN2 knockdown has been demonstrated to prevent amino acid deprivation (AAD)-induced expression of Vascular Endothelial Growth Factor (VEGF) which tumors use to enhance nutrient supply via increased vascularization. Thus, activation of the GCN2/ATF4 pathway promotes tumor growth and angiogenesis through AAD-mediated VEGF expression. Abrogation of ATF4 or GCN2 expression significantly inhibited tumor growth in vivo.

Therefore, selective inhibition of GCN2 can both increase the activity of the immune system and decrease vascularization in the tumor microenvironment. The GCN2-eIF2α-ATF4 pathway is critical for maintaining metabolic homeostasis in tumor cells under conditions of stress, and for maintaining an immunosuppressed immune cell microenvironment. The PERK-ATF4 pathway is also critical for maintaining homeostasis in tumors cells under conditions of stress. It has been reported that there is cross talk regulation of both the GCN2 and PERK signaling pathways, such that inhibition of GCN2 can activate PERK as a compensatory mechanism, and vice versa, that inhibition of PERK an activate GCN2 as a compensatory mechanism.

There is a need for inhibitors of GCN2 and/or PERK that modulate the pro-tumoral aspects of GCN2 and/or PERK, both in the tumor cell (tumor cell autonomous) and in the tumor immune cell microenvironment.

SUMMARY

Described herein are compounds that modulate (e.g., inhibit or activate) the GCN2 (general control nonderepressible 2) kinase and/or PERK (PKR-like ER kinase) kinase and methods of use thereof for the treatment of disorders, including GCN2 or PERK associated diseases.

In one embodiment, described herein is a compound represented by Formula I-A:

Formula I-A

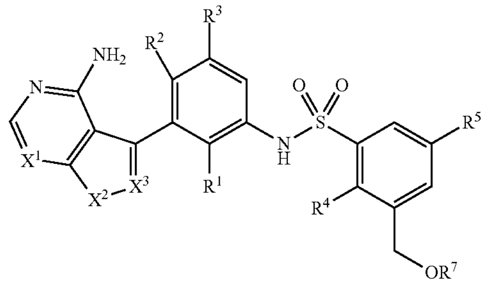

or a pharmaceutically acceptable salt, enantiomer, stereoisomer, or tautomer thereof, wherein: $X^1$ and $X^3$ are each independently selected from the group consisting of CH and N; $X^2$ is selected from the group consisting of $NR^6$, O, and S; $R^1$, $R^2$, and $R^3$ are each independently selected from the group consisting of H, halogen, cyano, and alkoxy; $R^4$ is selected from the group consisting of halogen, alkoxy and alkyl; $R^5$ is selected from the group consisting of H, halogen and alkyl; $R^6$ is selected from the group consisting of H, alkyl, alkenyl, alkenylalkyl, alkynyl, alkynylalkyl, cycloalkyl, cycloalkylalkyl, alkoxyalkyl, cycloalkenyl, heterocyclyl, heterocyclylalkyl, aryl, heteroaryl, and heteroarylalkyl; and $R^7$ is selected from the group consisting of H, alkyl, and acyl.

In another embodiment, described herein is a pharmaceutical composition comprising a compound described herein (e.g., a compound of Formulae I-A, I-B, I-C, and I-D described herein) and a pharmaceutically acceptable carrier or excipient.

In another embodiment, described herein is a method of treating a disease caused by a dysregulation of an integrated stress response in a patient in need thereof, comprising administering to the patient a therapeutically effective amount of a compound described herein, or a pharmaceutically acceptable salt thereof, or of a pharmaceutical composition described herein.

In another embodiment, described herein is a method of treating a disease caused by a dysregulation of an integrated stress response and/or an unfolded protein response in a patient in need thereof, comprising administering to the patient a therapeutically effective amount of a compound described herein, or a pharmaceutically acceptable salt thereof, or of a pharmaceutical composition described herein.

In another embodiment, described herein is a method of modulating the activity of GCN2 kinase in a patient in need thereof, comprising administering to the patient a therapeutically effective amount of a compound described herein, or a pharmaceutically acceptable salt thereof, or of a pharmaceutical composition described herein.

In another embodiment, described herein is a method of activating GCN2 kinase in a patient in need thereof, comprising administering to the patient a therapeutically effective amount of a compound described herein, or a pharmaceutically acceptable salt thereof, or of a pharmaceutical composition described herein.

In another embodiment, described herein is a method of modulating the activity of PERK kinase in a patient in need thereof, comprising administering to the patient a therapeutically effective amount of a compound described herein, or a pharmaceutically acceptable salt thereof, or of a pharmaceutical composition described herein.

In another embodiment, described herein is a method of activating PERK kinase in a patient in need thereof, comprising administering to the patient a therapeutically effective amount of a compound described herein, or a pharmaceutically acceptable salt thereof, or of a pharmaceutical composition described herein.

In another embodiment, described herein is a method of inhibiting GCN2 kinase and inhibiting PERK kinase in a patient in need thereof, comprising administering to the patient a therapeutically effective amount of a compound described herein, or a pharmaceutically acceptable salt thereof, or of a pharmaceutical composition described herein.

In another embodiment, described herein is a method of modulating the activity of GCN2 kinase in a patient in need thereof, comprising administering to the patient a therapeutically effective amount of a compound described herein, or a pharmaceutically acceptable salt thereof, or of a pharmaceutical composition described herein.

In another embodiment, described herein is a method of inhibiting the activity of PERK kinase in a patient in need thereof, comprising administering to the patient a therapeutically effective amount of a compound described herein, or a pharmaceutically acceptable salt thereof, or of a pharmaceutical composition described herein.

In another embodiment, described herein is a method of treating a disease selected from a GCN2 associated disease and a PERK associated disease, in a patient in need thereof, comprising administering to the patient a therapeutically effective amount of a compound described herein, or a pharmaceutically acceptable salt thereof, or of a pharmaceutical composition described herein.

In another embodiment, described herein is a method of treating a disease selected from a GCN2 associated disease and a PERK associated disease, in a patient in need thereof, comprising administering to the patient a therapeutically effective amount of a compound described herein, or a pharmaceutically acceptable salt thereof, and a therapeutically effective amount of one or more therapeutic agents.

In another embodiment, described herein is a method of treating a cancer in a patient in need thereof, comprising administering to the patient a therapeutically effective amount of a compound described herein (e.g., a compound of Formulae I-A, I-B, I-C, and I-D described herein) or a pharmaceutically acceptable salt thereof, or pharmaceutical composition described herein.

In another embodiment, described herein is a method of treating a disorder selected from the group consisting of melanoma, fibrosarcoma, thyroid cancer, ovarian cancer, colon cancer, pancreatic cancer, lung cancer, bladder cancer, gastrointestinal stromal tumors, solid tumors, blood-borne cancers, acute myelogenous leukemia (AML), acute lymphoblastic leukemia (ALL) and other cancers caused by activation of the GCN2 signaling pathway in a patient in need thereof, comprising administering to the patient a therapeutically effective amount of a compound described herein (e.g., a compound of Formulae I-A, I-B, I-C, and I-D described herein) or a pharmaceutically acceptable salt thereof.

BRIEF DESCRIPTION OF THE DRAWINGS

FIG. 7A shows data plots of results obtained from the PK/PD model studies and FIG. 7B depicts results in tabular form.

FIG. 10B, H358; FIG. 10C, HT-1080) cell lines.

FIG. 11A illustrates cell regression in the H2030 solid tumor spheroids by Compound 2 as a single agent in the H2030 solid tumor spheroids as a single agent. FIGS. 11B and 11C show effects of Compound 2 on cell proliferation of H358 (FIG. 11B) and the HT-1080 (FIG. 11C) solid tumor spheroids as a single agent.

FIG. 12A represents a cell proliferation experiment of H2030 NSCLC spheroids treated with Compound 2 titer in combination with or without sotorasib. FIG. 12B represents a cell proliferation experiment of H2030 NSCLC spheroids treated with Compound 2 titer in combination with or without sotorasib. FIG. 12C represents a cell proliferation experiment of H2030 NSCLC spheroids treated with Compound 2 titer in combination with or without trametinib.

FIG. 13A illustrates GCN2 and PERK knowndown using targeting shRNAs in the HT-1080 cell line. FIG. 13B represents Western blot quantification of ATF4 signal. FIG. 13C illustrates effects of Compound 2 on spheroid growth inhibition.

FIG. 14A shows upregulation of ATF4 levels by Compound 2 at different doses. FIG. 14B shows the corresponding plasma levels of Compound 2 at various time points post dose.

FIG. 15A shows effect of Compound 2 on tumor growth in the LoVo colorectal xenograft model and FIG. 15B shows effect of Compound 2 on tumor growth of the HT-1080 fibrosarcoma xenograft model.

DETAILED DESCRIPTION

Figure 1:
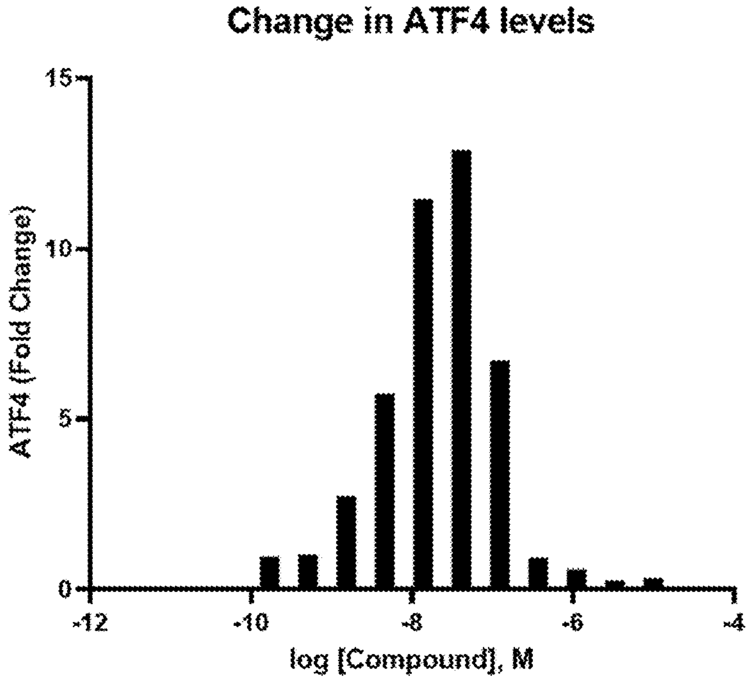
FIG. 1 is a graphical representation demonstrating the unexpected stimulation of the UPR/ISR marker ATF4 (black bars) in response to increasing concentrations of Compound 2.

The features and other details of the disclosure are more particularly described below. Certain terms employed in the specification, examples and appended claims are collected here. These definitions should be read in light of the remainder of the disclosure and as understood by a person of skill in the art. Unless defined otherwise, all technical and scientific terms used herein have the same meaning as commonly understood by a person of ordinary skill in the art.

Definitions

The definitions set forth in this application are intended to clarify terms used throughout this application.

Unless defined otherwise, all technical and scientific terms used herein have the same meaning as is commonly understood by one of skill in the art to which the subject matter herein belongs. As used in the specification and the appended claims, unless specified to the contrary, the following terms have the meaning indicated in order to facilitate the understanding of the present disclosure.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents, positions of substituents and/or variables are permissible if such combinations result in stable compounds.

As used herein, the singular forms "a", "an" and "the" encompass plural references unless the context clearly indicates otherwise.

As used herein, the term "herein" means the entire application.

As used herein, "deuterated" mean that at least one hydrogen atom is replaced by deuterium. In any sample of a deuterated compound, some discrete molecules of the compound will likely have hydrogen, rather than deuterium, at the specified position. However, the percent of molecules of the deuterated compound which have deuterium at the specified position will be much greater than would naturally occur. The deuterium at the deuterated position is enriched.

As used herein, the terms "optional" or "optionally" mean that the subsequently described event or circumstance may occur or may not occur, and that the description includes instances where the event or circumstance occurs as well as instances in which it does not. For example, "optionally substituted alkyl" refers to the alkyl may be substituted as well as where the alkyl is not substituted.

It is understood that substituents and substitution patterns on the disclosed compounds can be selected by one of ordinary skilled person in the art to result chemically stable compounds which can be readily synthesized by techniques known in the art, as well as those methods set forth below, from readily available starting materials. If a substituent is itself substituted with more than one group, it is understood that these multiple groups may be on the same carbon or on different carbons, so long as a stable structure result.

As used herein, the term "optionally substituted" refers to the replacement of one to six hydrogen atoms in a given structure with the radical of a specified substituent including, but not limited to: hydroxy, hydroxyalkyl, alkoxy, halogen, alkyl, aryl, cycloalkyl, heterocyclyl, amino, aminoalkyl, cyano, haloalkyl, haloalkoxy, $—OC(=O)—CH_2$-Oalkyl. Preferably, "optionally substituted" refers to the replacement of one to four hydrogen atoms in a given structure with the substituents mentioned above. More preferably, one to three hydrogen atoms are replaced by the substituents as mentioned above. It is understood that the substituent can be further substituted.

As used herein, the term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this application, the heteroatoms such as nitrogen may have hydrogen substituents and/or any permissible substituents of organic compounds described herein which satisfy the valences of the heteroatoms.

Substituents can include any substituents described herein, for example, such substituents, if not otherwise specified, can include, for example, a halogen, a hydroxy, a carbonyl (such as a carboxyl, an alkoxycarbonyl, a formyl, or an acyl), an alkoxy, an amino, an amido, an imine, a cyano, a sulfonyl, a heterocyclyl, an aralkyl, a heteroaralkyl, or an aromatic or heteroaromatic moiety. It will be understood by those skilled in the art that substituents can themselves be substituted, if appropriate. For instance, the substituents of a substituted alkyl may include substituted and unsubstituted forms of amino, amido, sulfonyl and as well as ethers, carbonyls (including carboxylates, and esters), $—CF_3$, —CN and the like. Unless specifically stated as "unsubstituted," references to chemical moieties herein are understood to include substituted variants. For example, reference to an "aryl" group or moiety implicitly includes both substituted and unsubstituted variants.

As used herein, the term "alkyl" refers to a straight chained or branched non-aromatic hydrocarbon which is completely saturated. Typically, a straight chained or branched alkyl group has from 1 to about 20 carbon atoms, preferably from 1 to about 10, e.g., may be $C_1$-$C_{10}$alkyl or e.g., $C_1$-$C_6$alkyl unless otherwise defined. Examples of straight chained and branched alkyl groups include, but are not limited to, methyl, ethyl, 1-propyl (n-propyl), 2-propyl, n-butyl, sec-butyl, tertbutyl, 1-pentyl, 2-pentyl, 3-pentyl, neo-pentyl, 1-hexyl, 2-hexyl, 3-hexyl, 1-heptyl, 2-heptyl, 3-heptyl, 4-heptyl, 1-octyl, 2-octyl, 3-octyl or 4-octyl and the like. Moreover, the term "alkyl" used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. The "alkyl" group may be optionally substituted.

The term "$C_x$-$C_y$" when used in conjunction with a chemical moiety, such as, acyl, acyloxy, alkyl, alkenyl, alkynyl, or alkoxy is meant to include groups that contain from x to y carbons in the chain. For example, the term "$C_x$-$C_y$" refers to substituted or unsubstituted saturated hydrocarbon groups, including straight-chain alkyl and branched-chain alkyl groups that contain from x toy carbons in the chain, including haloalkyl groups such as trifluoromethyl and 2,2,2-trifluoroethyl, etc. $C_0$ alkyl indicates a hydrogen where the group is in a terminal position, a bond if internal.

The term "alkenyl" as used herein refers to an unsaturated straight or branched hydrocarbon having at least one carbon-carbon double bond. Exemplary alkenyl groups include, but are not limited to, a straight or branched group of 2-6 or 3-4 carbon atoms, referred to herein as $C_2$-$C_6$alkenyl, and $C_3$-$C_4$alkenyl, respectively. Exemplary alkenyl groups include, but are not limited to, vinyl, allyl, butenyl, pentenyl, etc.

The term "alkynyl" as used herein refers to an unsaturated straight or branched hydrocarbon having at least one carbon-carbon triple bond. Exemplary alkynyl groups include, but are not limited to, straight or branched groups of 2-6, or 3-6 carbon atoms, referred to herein as $C_2$-$C_6$alkynyl, and $C_3$-$C_6$alkynyl, respectively. Exemplary alkynyl groups include, but are not limited to, ethynyl, propynyl, butynyl, pentynyl, hexynyl, methylpropynyl, etc.

As used herein, the term "alkoxy" refers to a straight or branched, saturated aliphatic (alkyl) hydrocarbon radical bonded to an oxygen atom that is attached to a core structure. Preferably, alkoxy groups have one to six carbon atoms, i.e., may be $C_1$-$C_6$ alkoxy. Examples of alkoxy groups include but are not limited to methoxy, ethoxy, propoxy, isopropoxy, butoxy, isobutoxy, tert-butoxy, pentoxy, 3-methyl butoxy and the like.

As used herein, the term "alkoxyalkyl" refers to an alkyl group (as defined above) substituted with an alkoxy group and may be represented by the general formula alkyl-O-alkyl. Examples of alkoxyalkyl groups include but are not limited to methyl-O-ethylene-, ethyl-O-ethylene-.

As used herein, the term "haloalkyl" refers to alkyl group (as defined above) is substituted with one or more halogens. A monohaloalkyl radical, for example, may have a chlorine, bromine, iodine or fluorine atom. Dihalo and polyhaloalkyl radicals may have two or more of the same or different halogen atoms. Examples of haloalkyl include, but are not limited to, chloromethyl, dichloromethyl, trichloromethyl, dichloroethyl, dichloropropyl, fluoromethyl, difluoromethyl, trifluoromethyl, pentafluoroethyl, heptafluoropropyl, difluorochloromethyl, dichlorofluoromethyl, difluoroethyl, difluoropropyl and the like.

As used herein, the term "haloalkoxy" refers to radicals wherein one or more of the hydrogen atoms of the alkoxy group are substituted with one or more halogens. Representative examples of "haloalkoxy" groups include, but not limited to, difluoromethoxy ($—OCHF_2$), trifluoromethoxy ($—OCF_3$) or trifluoroethoxy ($—OCH_2CF_3$).

As used herein, the term "aryl" includes substituted or unsubstituted single-ring aromatic groups in which each atom of the ring is carbon. Preferably the ring is a 5- to 7-membered ring, more preferably a 6-membered ring. The term "aryl" also includes polycyclic ring systems having two or more cyclic rings in which two or more carbons are common to two adjoining rings (fused rings) wherein at least one of the rings is aromatic. e.g., the other cyclic rings can be cycloalkyls, cycloalkenyls, cycloalkynyls, aryls, heteroaryls, and/or heterocyclyls. The term "fused" means that the second ring is attached or formed by having two adjacent atoms in common with the first ring. The term "fused" is equivalent to the term "condensed". Examples of aryl groups include but are not limited to phenyl, naphthyl, phenanthryl, phenol, aniline, indanyl, dihydrobenzofuranyl, dihydroisobenzofuranyl, indolinyl, isoindolinyl, and the like. Unless otherwise specified, aryl groups described herein may be optionally substituted.

As used herein, the terms "polycyclyl", "polycycle", and "polycyclic" refer to two or more rings (e.g., cycloalkyls, cycloalkenyls, cycloalkynyls, aryls, heteroaryls, and/or heterocyclyls) in which one or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

As used herein, the term "acyl" refers to a group $—C(=O)—R^w$ wherein $R^w$ is optionally substituted alkyl. Examples of "acyl" include, but are not limited to, instances where $R^w$ is $C_1$-$C_{10}$alkyl ($C_1$-$C_{10}$acyl) or $C_1$-$C_6$-alkyl ($C_1$-$C_6$acyl). In some embodiments, each occurrence of the optionally substituted substituent is independently selected from the group consisting of H, OH, alkoxy, cyano, F, and amino. Additional examples of "acyl" include $—C(=O)—CH_3$, $—C(=O)—CH_2—CH_3$, $—C(=O)—CH_2—CH_2—CH_3$, or $—C(=O)—CH(CH_3)_2$.

As used herein, the terms "amine" and "amino" refer to both unsubstituted and substituted amines and salts thereof, e.g., a moiety that can be represented by:

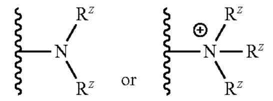

wherein each $R^z$ independently represents hydrogen or a hydrocarbyl group, or $R^z$ groups are taken together with the N atom to which they are attached complete a heterocycle having from 4 to 8 atoms in the ring structure.

As used herein, the terms "amide" and "amido" refers to a group represented by

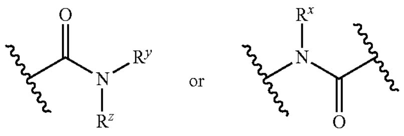

wherein $R^x$, $R^y$, and $R^z$ each independently represents hydrogen or a hydrocarbyl group, or $R^y$ and $R^z$ are taken together with the N atom to which they are attached complete a heterocyclyl having from 4 to 8 atoms in the ring structure.

As used herein, the term "acylamino" refers to an amino group, as defined above, substituted with an acyl group.

As used herein, the term "aminocarbonyl" refers to a carbonyl group substituted with an amino group.

As used herein, the term "alkenylalkyl" refers to an alkyl group substituted with an alkenyl group.

As used herein, the term "alkynylalkyl" refers to an alkyl group substituted with an alkynyl group.

As used herein, the term "alkylamino" refers to an amino group, as defined above, substituted with at least one alkyl group.

As used herein, the term "aminoalkyl" refers to an alkyl group substituted with an amino group.

As used herein, the term "amidoalkyl" refers to an alkyl group substituted with an amido group.

As used herein, the term "cyanoalkyl" refers to an alkyl group substituted with a cyano group.

As used herein, the term "cycloalkoxyalkyl" refers to an alkyl group (as defined above) substituted with a cycloalkoxy group and may be represented by the general formula cycloalkyl-O-alkyl. Examples of cycloalkoxyalkyl groups include but are not limited to cyclopropyl-O-methylene-, cyclopropyl-O-ethylene.

As used herein, the term "cycloalkylalkyl" refers to an alkyl group substituted with a cycloalkyl group.

As used herein, the term "heteroarylalkyl" refers to an alkyl group substituted with heteroaryl group.

As used herein, the term "heterocyclylalkyl" refers to an alkyl group substituted with a heterocyclyl group.

As used herein, the term "hydroxyalkyl" refers to an alkyl group substituted with a hydroxy group.

As used herein, the term "cycloalkyl" alone or in combination with other term(s) refers to a cyclic hydrocarbon which is completely saturated. "Cycloalkyl" includes monocyclic, bicyclic, and tricyclic rings. Typically, a monocyclic cycloalkyl group has from 3 to about 10 carbon atoms, more typically 3 to 8 carbon atoms (e.g., $C_3$-$C_{10}$cycloalkyl or e.g., $C_3$-$C_6$cycloalkyl unless otherwise defined. Examples of monocyclic cycloalkyls include cyclopropyl, cyclobutyl, cyclopentyl, cyclohexyl, cycloheptyl and the like. The second ring of a bicyclic cycloalkyl or, the second or third rings of a tricyclic cycloalkyl, may be selected from saturated, unsaturated and aromatic rings. Cycloalkyl includes bicyclic and tricyclic molecules in which one, two or three or more atoms are shared between the two rings. Cycloalkyls can be further substituted with alkyls, alkenyls, alkoxys, aminoalkyls, carbonyl-substituted alkyls, —$CF_3$, —CN, and the like.

As used herein, the term "cycloalkylalkyl" refers to an alkyl group substituted with a cycloalkyl group.

As used herein, the term "cyano" refers to —CN group.

As used herein, the term "hydroxy" or "hydroxyl" refers to —OH group.

As used herein, the term "halo" or "halogen" alone or in combination with other term(s) means chloro, fluoro, bromo, and iodo.

As used herein, the term "heteroatom" refers an atom of any element other than carbon or hydrogen. Exemplary heteroatoms are nitrogen (N), oxygen (O), sulfur (S), and silicon (Si).

As used herein, the terms "heterocyclyl", "heterocycloalkyl", "heterocycle", and "heterocyclic" refer to a non-aromatic, saturated or partially saturated, including monocyclic, polycyclic (e.g., bicyclic, tricyclic) bridged, or fused, ring system of 3 to 15 member having at least one heteroatom or hetero group selected from O, N, S, S(O), $S(O)_2$, NH or C(O) with the remaining ring atoms being independently selected from the group consisting of carbon, oxygen, nitrogen, and sulfur. Examples of "heterocycloalkyl" include, but are not limited to azetidinyl, oxetanyl, imidazolidinyl, pyrrolidinyl, oxazolidinyl, thiazolidinyl, pyrazolidinyl, tetrahydrofuranyl, piperidinyl, piperazinyl, tetrahydropyranyl, morpholinyl, thiomorpholinyl, 1,4-dioxanyl, dioxidothiomorpholinyl, oxapiperazinyl, oxapiperidinyl, tetrahydrofuryl, tetrahydropyranyl, tetrahydrothiophenyl, dihydropyranyl, indolinyl, indolinylmethyl, 2-azabicyclo[2.2.2]octanyl, azocinyl, chromanyl, xanthenyl and N-oxides thereof. Attachment of a heterocycloalkyl substituent can occur via either a carbon atom or a heteroatom. A heterocycloalkyl group can be optionally substituted with one or more suitable groups by one or more aforesaid groups. Preferably "heterocycloalkyl" refers to 5- to 6-membered ring selected from the group consisting of azetidinyl, oxetanyl, imidazolidinyl, pyrrolidinyl, oxazolidinyl, thiazolidinyl, pyrazolidinyl, tetrahydrofuranyl, piperidinyl, piperazinyl, tetrahydropyranyl, morpholinyl, thiomorpholinyl, 1,4-dioxanyl and N-oxides thereof. More preferably, "heterocycloalkyl" includes azetidinyl, pyrrolidinyl, morpholinyl and piperidinyl. Heterocycloalkyl are optionally substituted by one or more aforesaid groups.

As used herein, the term "heteroaryl" refers to substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The term "heteroaryl" also refers to substituted or unsubstituted aromatic or partly aromatic ring systems containing at least one heteroatom and having two or more cyclic rings (bicyclic, tricyclic, or polycyclic), containing 8 to 20 ring atoms, suitably 5 to 10 ring atoms, which may be linked covalently, or fused in which two or more atoms are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. The rings may contain an N or S atom, wherein the N or S atom is optionally oxidized, or the N atom is optionally quaternized. All heteroaryls are optionally substituted. Any suitable ring position of the heteroaryl moiety may be covalently linked to a defined chemical structure. Examples of heteroaryl include, but are not limited to: furanyl, thienyl, pyrrolyl, pyrazolyl, imidazolyl, oxazolyl, cinnolinyl, isoxazolyl, thiazolyl, isothiazolyl, 1H-tetrazolyl, oxadiazolyl, thiadiazolyl, triazolyl, pyridyl, pyrimidinyl, pyrazinyl, pyridazinyl, triazinyl, benzoxazolyl, benzisoxazolyl, benzothiazolyl, benzofuranyl, benzothienyl, benzotriazinyl, phthalazinyl, thianthrene, dibenzofuranyl, dibenzothienyl, benzimidazolyl, indolyl, isoindolyl, indazolyl, quinolinyl, isoquinolinyl, quinazolinyl, quinoxalinyl, purinyl, pteridinyl, 9H-carbazolyl, alpha-carboline, indolizinyl, benzoisothiazolyl, benzoxazolyl, pyrrolopyridyl, furopyridinyl, purinyl, benzothiadiazolyl, benzoxadiazolyl, benzotriazolyl, benzotriadiazolyl, carbazolyl, dibenzothienyl, acridinyl and the like.

As used herein, the term "hydrocarbyl" refers to a group that is bonded through a carbon atom that does not have a =O or =S substituent, and typically has at least one carbon-hydrogen bond and a primarily carbon backbone but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, cycloalkyl, heterocyclyl, alkyl, alkenyl, alkynyl, and combinations thereof.

As used herein, the term "sulfonamide" is represented by:

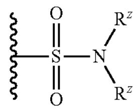

or

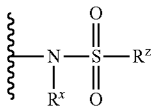

wherein $R^z$, at each occurrence, independently represents a hydrogen, alkyl or cycloalkyl group, or $R^z$ groups taken together with the N atom to which they are attached complete a heterocycle having from 4 to 8 atoms in the ring structure.

As used herein, the terms "sulfonyl" refers to the group $—S(O)_2—R^{6d}$ wherein $R^{6d}$ represents alkyl or cycloalkyl.

A "combination therapy" is a treatment that includes the administration of two or more therapeutic agents, e.g., a compound of Formula I and the enzyme asparaginase (ASNase) or a derivative thereof, to a patient in need thereof.

"Disease," "disorder," and "condition" are used interchangeably herein.

"Individual," "patient," or "subject" are used interchangeably and include any animal, including mammals, preferably mice, rats, other rodents, rabbits, dogs, cats, swine, cattle, sheep, horses, or primates, and most preferably humans. The compounds described herein can be administered to a mammal, such as a human, but can also be administered to other mammals such as an animal in need of veterinary treatment, e.g., domestic animals (e.g., dogs, cats, and the like), farm animals (e.g., cows, sheep, pigs, horses, and the like) and laboratory animals (e.g., rats, mice, guinea pigs, and the like).

The compounds described herein are useful for the treatment of diseases driven by GCN2 (sometimes to be abbreviated as "GCN2 associated disease" in the present specification), for example, cancer [e.g., colorectal cancer (e.g., colorectal cancer, rectal cancer, anal cancer, familial colorectal cancer, hereditary nonpolyposis colorectal cancer, gastrointestinal stromal tumor), lung cancer (e.g., non-small cell lung cancer, small cell lung cancer, malignant mesothelioma), mesothelioma, pancreatic cancer (e.g., pancreatic duct cancer, pancreatic endocrine tumor), pharyngeal cancer, laryngeal cancer, esophagus cancer, gastric cancer (e.g., papillary adenocarcinoma, mucinous adenocarcinoma, adenosquamous carcinoma), duodenal cancer, small intestinal cancer, breast cancer (e.g., invasive ductal carcinoma, ductal carcinoma in situ, inflammatory breast cancer), ovarian cancer (e.g., ovarian epithelial carcinoma, extragonadal germ cell tumor, ovarian germ cell tumor, ovarian low malignant potential tumor), testis tumor, prostate cancer (e.g., hormone-dependent prostate cancer, non-hormone dependent prostate cancer, castration-resistant prostate cancer), liver cancer (e.g., hepatoma, primary liver cancer, extrahepatic bile duct cancer), thyroid cancer (e.g., medullary thyroid carcinoma), renal cancer (e.g., renal cell carcinoma (e.g., clear cell renal cell carcinoma), transitional cell carcinoma of renal pelvis and ureter), uterine cancer (e.g., cervical cancer, uterine body cancer, uterus sarcoma), gestational choriocarcinoma, brain tumor (e.g., medulloblastoma, glioma, pineal astrocytoma, pilocytic astrocytoma, diffuse astrocytoma, anaplastic astrocytoma, hypophyseal adenoma), retina blastoma, skin cancer (e.g., basal cell carcinoma, malignant melanoma (melanoma)), sarcoma (e.g., rhabdomyosarcoma, leiomyosarcoma, soft tissue sarcoma, spindle cell sarcoma, osteosarcoma), malignant bone tumor, urinary bladder cancer, hematologic cancer (e.g., multiple myeloma, leukemia (e.g., acute myeloid leukemia, acute lymphocytic leukemia (including blast crisis of chronic leukemia)), malignant lymphoma, Hodgkin's disease, chronic myeloproliferative disease), cancer of unknown primary nucleus], cancer growth inhibitor, cancer metastasis inhibitor, apoptosis promoter, and for the prophylaxis or treatment of precancerous lesion (e.g., bone marrow myelodysplastic syndrome).

The compounds described herein, e.g., a compound of Formula I as defined herein, may be used in combination with one or more additional therapeutic agents to treat a disorder described herein, such as a cancer described herein. In some embodiments, the compounds described herein may be used in combination with hormonal therapeutic agents, chemotherapeutic agents, immunotherapeutic agents, medicaments inhibiting actions of cell growth factor and receptor thereof, such as PERK inhibitors and autophagy inhibitors, the enzyme asparaginase (ASNase), and the like.

"Pharmaceutically or pharmacologically acceptable" include molecular entities and compositions that do not produce an adverse, allergic or other untoward reaction when administered to an animal, or a human, as appropriate. For human administration, preparations should meet sterility, pyrogenicity, and general safety and purity standards as required by FDA Office of Biologics standards.

The term "pharmaceutically acceptable carrier" or "pharmaceutically acceptable excipient" as used herein refers to any and all solvents, dispersion media, coatings, isotonic and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions.

The term "pharmaceutical composition" as used herein refers to a composition comprising at least one compound as disclosed herein formulated together with one or more pharmaceutically acceptable carriers.

The term "pharmaceutically acceptable salt(s)" as used herein refers to salts of acidic or basic groups that may be present in compounds used in the compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including, but not limited to, malate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that are acidic in nature are capable of forming base salts with various pharmacologically acceptable cations. Examples of such salts include alkali metal or alkaline earth metal salts, particularly calcium, magnesium, sodium, lithium, zinc, potassium, and iron salts. Compounds included in the present compositions that include a basic or acidic moiety may also form pharmaceutically acceptable salts with various amino acids. The compounds of the disclosure may contain both acidic and basic groups; for example, one amino and one carboxylic acid group. In such a case, the compound can exist as an acid addition salt, a zwitterion, or a base salt.

The compounds of the disclosure may contain one or more chiral centers and, therefore, exist as stereoisomers. The term "stereoisomers" when used herein consist of all enantiomers or diastereomers. These compounds may be designated by the symbol "R" or "S" depending on the configuration of substituents around the stereogenic carbon atom, but the skilled artisan will recognize that a structure may denote a chiral center implicitly. These compounds may also be designated by "(+)" and "(−)" based on their optical rotation properties. The presently described compounds encompasses various stereoisomers of these compounds and mixtures thereof. Mixtures of enantiomers or diastereomers may be designated by the symbol "(±)" in nomenclature, but the skilled artisan will recognize that a structure may denote a chiral center implicitly.

In the present specification, the term "therapeutically effective amount" means the amount of the subject compound that will elicit the biological or medical response of a tissue, system or animal, (e.g., mammal or human) that is being sought by the researcher, veterinarian, medical doctor or other clinician. The compounds described herein are administered in therapeutically effective amounts to treat a disorder.

"Treating" includes any effect, e.g., lessening, reducing, modulating, or eliminating, that results in the improvement of the condition, disease, disorder, and the like.

The disclosure also embraces isotopically labeled compounds which are identical to those recited herein, except that one or more atoms are replaced by an atom having an atomic mass or mass number different from the atomic mass or mass number usually found in nature. Examples of isotopes that can be incorporated into the disclosed compounds include isotopes of hydrogen, carbon, nitrogen, oxygen, phosphorus, sulfur, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. For example, a compound of the disclosure may have one or more H atom replaced with deuterium.

Individual enantiomers and diastereomers of the disclosed compounds can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, (3) direct separation of the mixture of optical enantiomers on chiral liquid chromatographic columns or (4) kinetic resolution using stereoselective chemical or enzymatic reagents. Racemic mixtures can also be resolved into their component enantiomers by well-known methods, such as chiral-phase liquid chromatography or crystallizing the compound in a chiral solvent. Stereoselective syntheses, a chemical or enzymatic reaction in which a single reactant forms an unequal mixture of stereoisomers during the creation of a new stereocenter or during the transformation of a pre-existing one, are well known in the art. Stereoselective syntheses encompass both enantio- and diastereoselective transformations and may involve the use of chiral auxiliaries. For examples, see Carreira and Kvaerno, *Classics in Stereoselective Synthesis*, Wiley-VCH: Weinheim, 2009.

Compounds

In one embodiment, described herein is a compound represented by Formula I-A:

Formula I-A

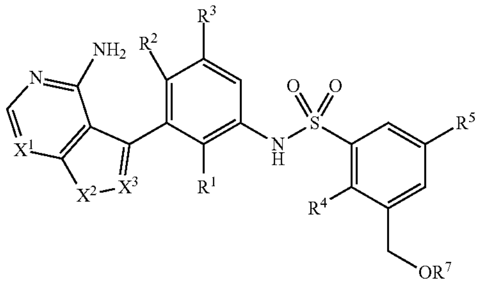

or a pharmaceutically acceptable salt, enantiomer, stereoisomer, or tautomer thereof, wherein: $X^1$ and $X^3$ are each independently selected from the group consisting of CH and N; $X^2$ is selected from the group consisting of $NR^6$, O, and S; $R^1$, $R^2$, and $R^3$ are each independently selected from the group consisting of H, halogen, cyano, and alkoxy; $R^4$ is selected from the group consisting of halogen, alkoxy and alkyl; $R^5$ is selected from the group consisting of H, halogen and alkyl; $R^6$ is selected from the group consisting of H, alkyl, alkenyl, alkenylalkyl, alkynyl, alkynylalkyl, cycloalkyl, cycloalkylalkyl, alkoxyalkyl, cycloalkenyl, heterocyclyl, heterocyclylalkyl, aryl, heteroaryl, and heteroarylalkyl; and $R^7$ is selected from the group consisting of H, alkyl, and acyl.

In some embodiments, at least one of $R^1$, $R^2$, and $R^3$ is halogen. In some embodiments, at least one of $R^1$, $R^2$, and $R^3$ is fluoro. In some embodiments, $R^1$ is fluoro. In some embodiments, $X^1$ is N.

In some embodiments, $R^6$ is not:

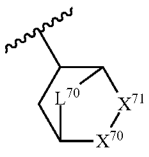

wherein $L^{70}$ is methylene or ethylene, and one of $X^{70}$ and $X^{71}$ is $CH_2$, and the other is N—CO—$R^{101}$, wherein $R^{101}$ is $C_{1-4}$ alkyl; $C_{2-4}$ alkenyl; or $C_{2-4}$ alkynyl, each of which is unsubstituted or substituted by one to three substituents each independently selected from the group consisting of halogen, cyano, hydroxy, amino, $NH(C_{1-4}$ alkyl), $N(C_{1-4}$ alkyl$)_2$, $C_{3-10}$ cycloalkyl, and $C_{3-10}$ heterocycloalkyl containing one or two heteroatoms each independently selected from the group consisting of nitrogen, and oxygen.

In another embodiment, described herein is a compound represented by Formula I-B:

Formula I-B

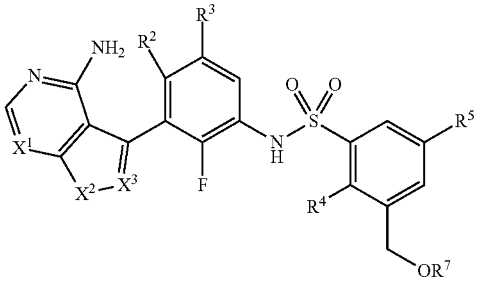

or a pharmaceutically acceptable salt, enantiomer, stereoisomer, or tautomer thereof, wherein: $X^1$ and $X^3$ are each independently selected from the group consisting of CH and N; $X^2$ is selected from the group consisting of $NR^6$, O, and S; $R^2$ and $R^3$ are each independently selected from the group consisting of H, halogen, cyano, and alkoxy; $R^4$ is selected from the group consisting of halogen, alkoxy and alkyl; $R^5$ is selected from the group consisting of H, halogen and alkyl; $R^6$ is selected from the group consisting of H, alkyl, alkenyl, alkenylalkyl, alkynyl, alkynylalkyl, cycloalkyl, cycloalkylalkyl, alkoxyalkyl, cycloalkenyl, heterocyclyl, heterocyclylalkyl, aryl, heteroaryl, and heteroarylalkyl; and $R^7$ is selected from the group consisting of H, alkyl, and acyl.

In some embodiments, $X^1$ is N.

In one embodiment, described herein is a compound represented by Formula I-C:

Formula I-C

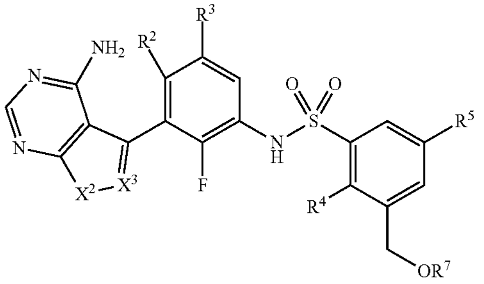

or a pharmaceutically acceptable salt, enantiomer, stereoisomer, or tautomer thereof, wherein: $X^2$ is selected from the group consisting of $NR^6$, O, and S; $X^3$ is selected from the group consisting of CH and N; $R^2$ and $R^3$ are each independently selected from the group consisting of H, halogen, cyano, and alkoxy; $R^4$ is selected from the group consisting of halogen, alkoxy, and alkyl; $R^5$ is selected from the group consisting of H, halogen, and alkyl; $R^6$ is selected from the group consisting of H, alkyl, alkenyl, alkenylalkyl, alkynyl, alkynylalkyl, cycloalkyl, cycloalkylalkyl, alkoxyalkyl, cycloalkenyl, heterocyclyl, heterocyclylalkyl, aryl, heteroaryl, and heteroarylalkyl; and $R^7$ is selected from the group consisting of H, alkyl, and acyl.

In some embodiments, $X^2$ is $NR^6$.

In another embodiment, described herein is a compound represented by Formula I-D:

Formula I-D

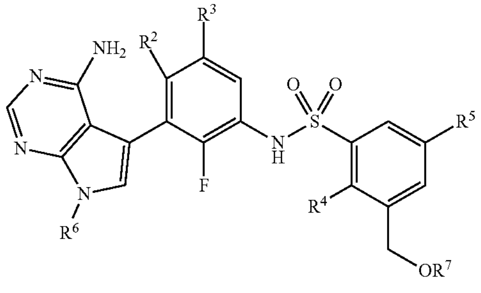

or a pharmaceutically acceptable salt, enantiomer, stereoisomer, or tautomer thereof, wherein: $R^2$ and $R^3$ are each independently selected from the group consisting of H, halogen, cyano, and alkoxy; $R^4$ is selected from the group consisting of halogen, alkoxy and alkyl; $R^5$ is selected from the group consisting of H, halogen and alkyl; $R^6$ is selected from the group consisting of H, alkyl, alkenyl, alkenylalkyl, alkynyl, alkynylalkyl, cycloalkyl, cycloalkylalkyl, alkoxyalkyl, cycloalkenyl, heterocyclyl, heterocyclylalkyl, aryl, heteroaryl, and heteroarylalkyl; and $R^7$ is selected from the group consisting of H, alkyl, and acetate.

In some embodiments, $R^2$ is H and $R^3$ is H. In some embodiments, $R^2$ is F and $R^3$ is H. In some embodiments, $R^2$ is H and $R^3$ is F. In some embodiments, $R^6$ is selected from the group consisting of $(C_1\text{-}C_8)$alkyl, $(C_2\text{-}C_8)$alkenyl, $(C_2\text{-}C_8)$alkenyl-$(C_1\text{-}C_4)$alkyl, $(C_2\text{-}C_8)$alkynyl, $(C_2\text{-}C_8)$alkynyl-$(C_1\text{-}C_4)$alkyl, $(C_3\text{-}C_8)$cycloalkyl, $(C_3\text{-}C_8)$cycloalkyl-$(C_1\text{-}C_4)$alkyl, $(C_3\text{-}C_8)$alkoxy-$(C_1\text{-}C_4)$alkyl, $(C_3\text{-}C_8)$cycloalkenyl, $(C_3\text{-}C_8)$cycloalkenyl-$(C_1\text{-}C_4)$alkyl, heterocyclyl, heterocyclyl-$(C_1\text{-}C_4)$alkyl, aryl, heteroaryl, and heteroaryl-$(C_1\text{-}C_4)$alkyl. In some embodiments, $R^6$ is selected from the group consisting of $(C_1\text{-}C_8)$alkyl, $(C_3\text{-}C_8)$cycloalkyl, $(C_3\text{-}C_8)$alkoxy-$(C_1\text{-}C_4)$alkyl, heterocyclyl, and heteroaryl. In some embodiments, $R^6$ is selected from the group consisting of:

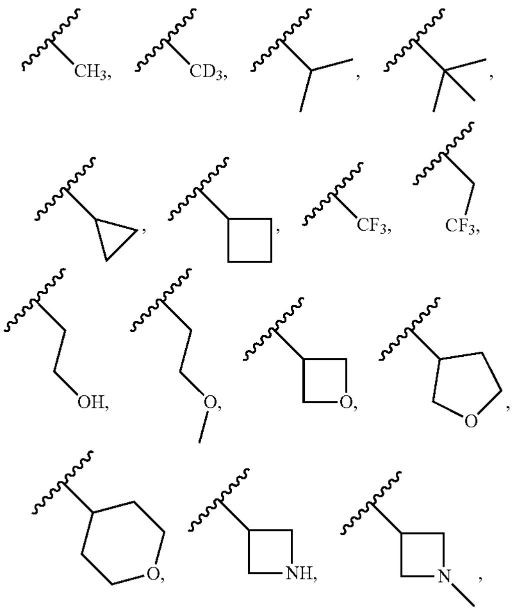

-continued

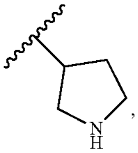, 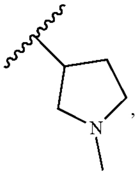, 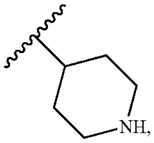,

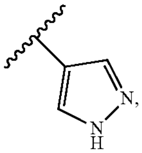, 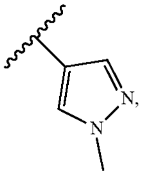, 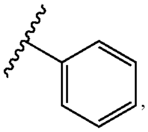,

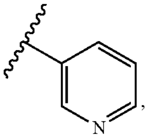, 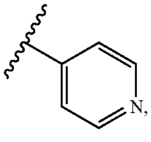, and 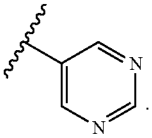.

In some embodiments, $R^6$ is not:

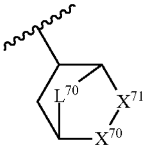

wherein $L^{70}$ is methylene or ethylene, and one of $X^{70}$ and $X^{71}$ is $CH_2$, and the other is N—CO—$R^{101}$, wherein $R^{101}$ is $C_{1-4}$ alkyl; $C_{2-4}$ alkenyl; or $C_{2-4}$ alkynyl, each of which is unsubstituted or substituted by one to three substituents each independently selected from the group consisting of halogen, cyano, hydroxy, amino, NH($C_{1-4}$ alkyl), N($C_{1-4}$ alkyl)$_2$, $C_{3-10}$ cycloalkyl, and $C_{3-10}$ heterocycloalkyl containing one or two heteroatoms each independently selected from the group consisting of nitrogen, and oxygen.

In some embodiments, $R^4$ is selected from the group consisting of halogen, ($C_1$-$C_6$)alkoxy and ($C_1$-$C_6$)alkyl. In some embodiments, $R^4$ is selected from the group consisting of chloro, fluoro, methoxy, and methyl. In some embodiments, $R^5$ is selected from the group consisting of H, halogen, and ($C_1$-$C_6$)alkyl. In some embodiments, $R^5$ is selected from the group consisting of chloro, fluoro, and methyl. In some embodiments, $R^7$ is H.

In an embodiment, described herein is a compound selected from the group consisting of:

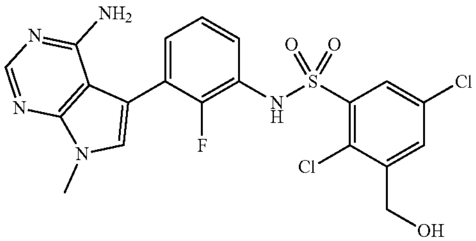

-continued

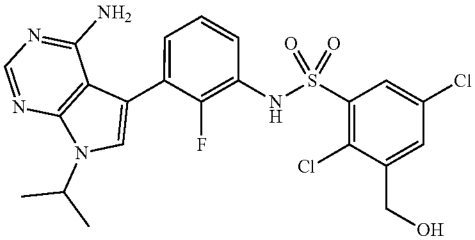

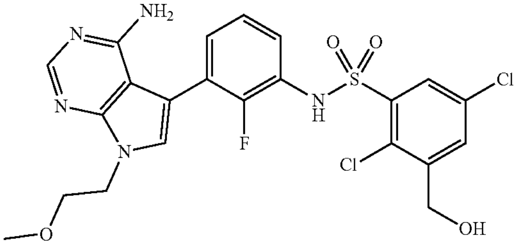

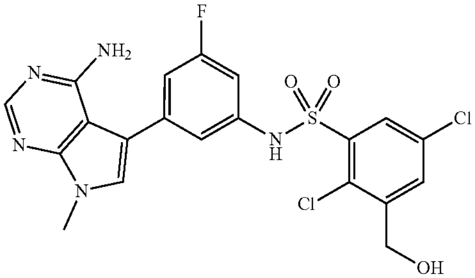

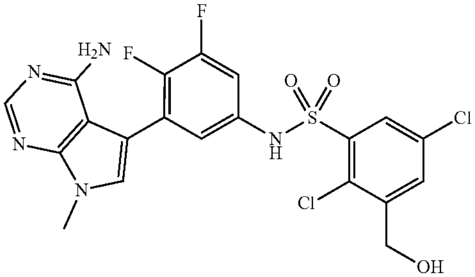

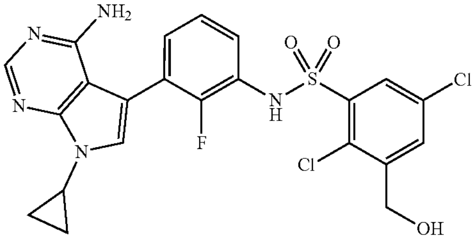

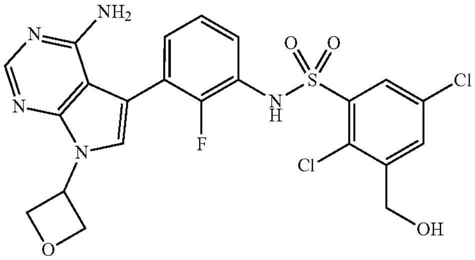

-continued
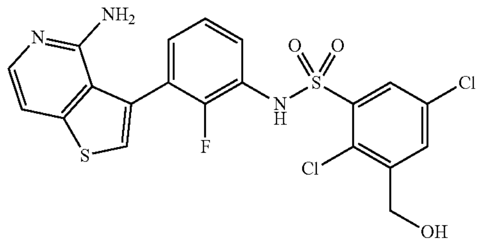
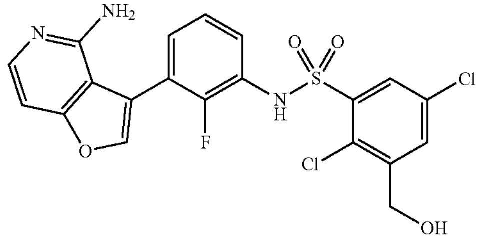
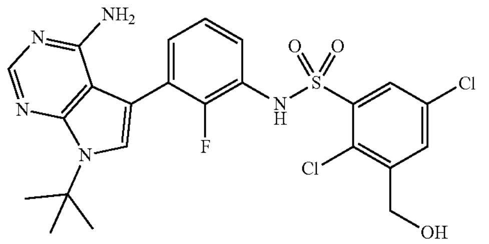
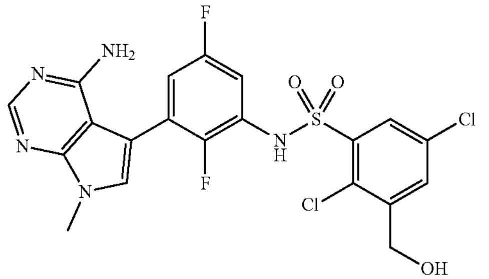
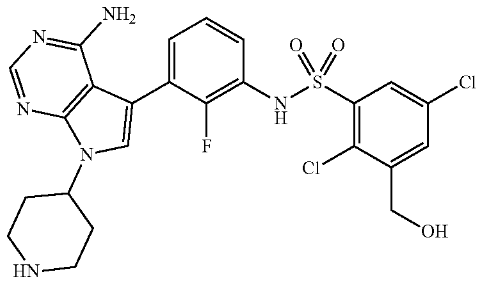
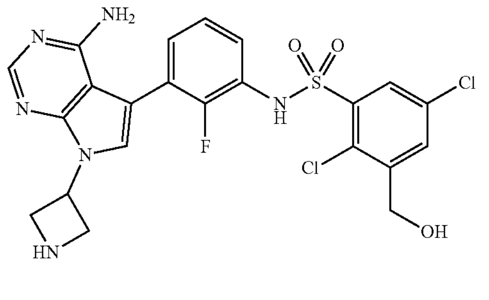
-continued
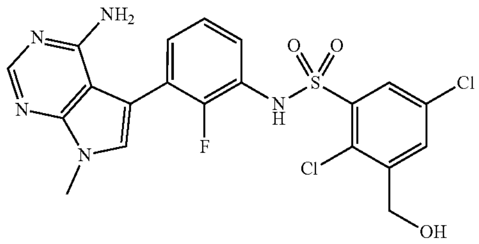
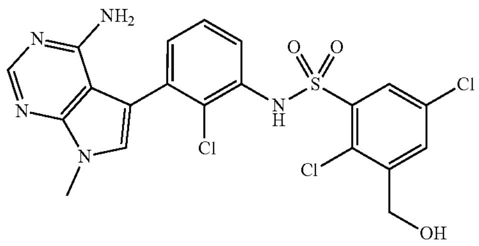
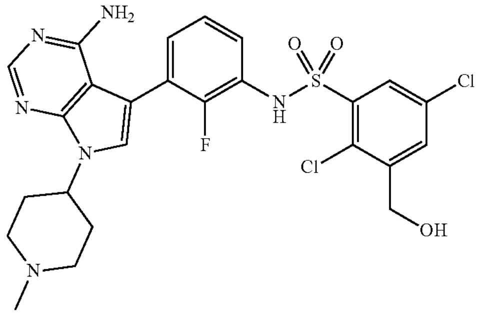
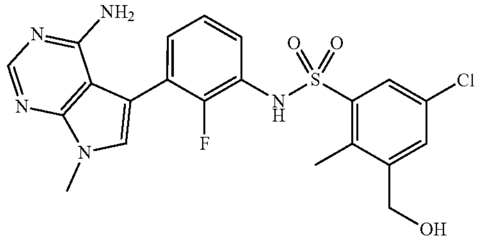
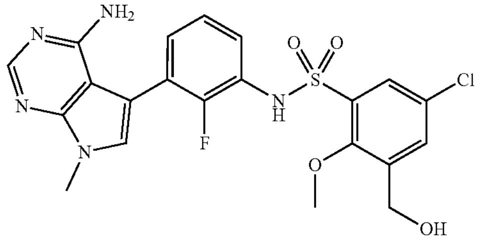
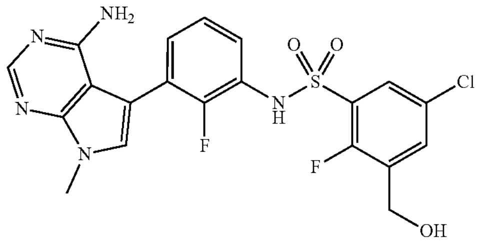

-continued
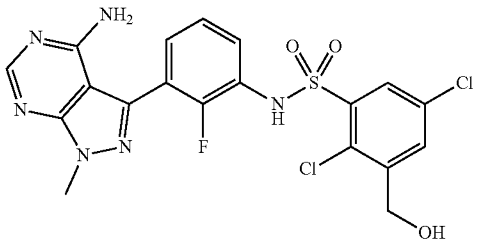
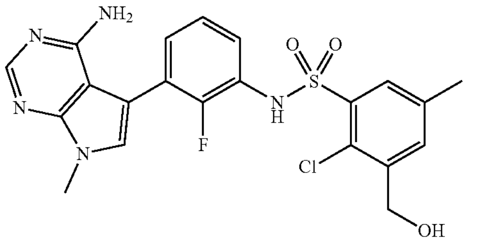
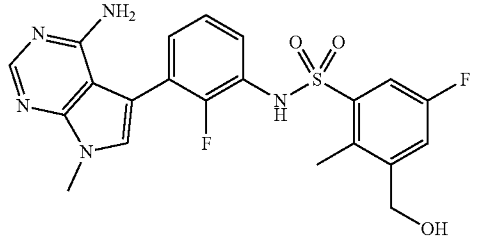
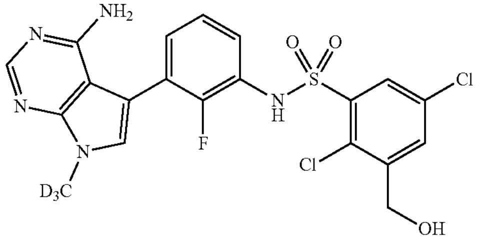
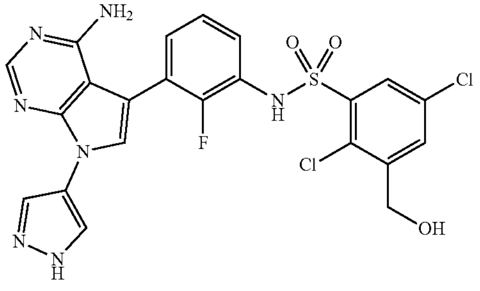
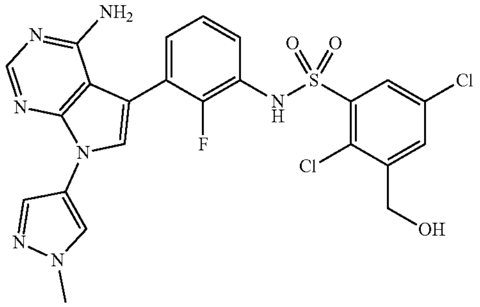
-continued
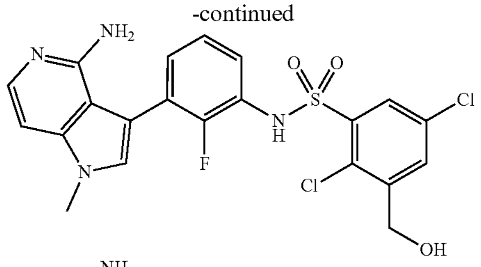
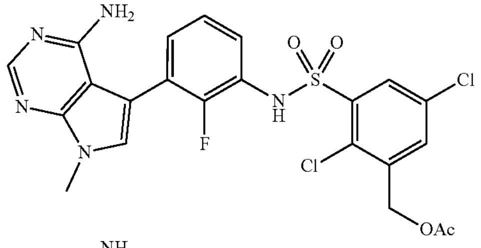
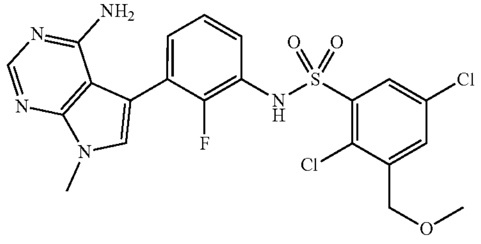
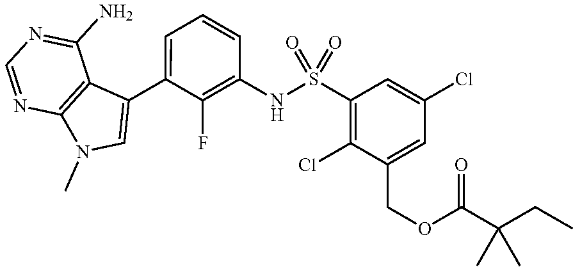
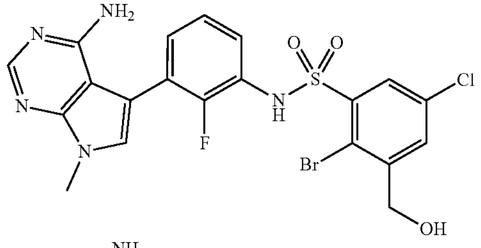
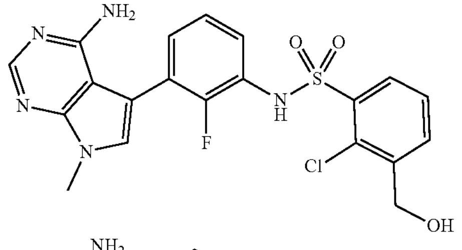
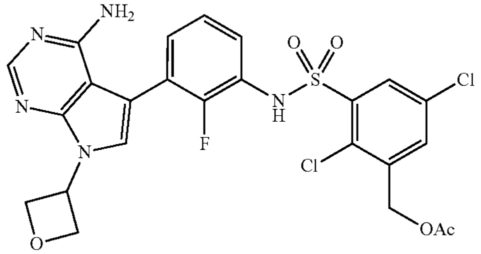

and pharmaceutically acceptable salts, enantiomers, stereoisomers, and tautomers thereof.

Methods of Treatment

Compounds described herein, e.g., compounds of Formula I as defined herein, can act as therapeutic agents for diseases driven by GCN2 or PERK kinase, and are useful in the treatment of diseases and disorders in patients in need thereof, such as cancer. Exemplary cancers include, but are not limited to, colorectal cancer, rectal cancer, anal cancer, familial colorectal cancer, hereditary nonpolyposis colorectal cancer, gastrointestinal stromal tumor, lung cancer (e.g., non-small cell lung cancer, small cell lung cancer, malignant mesothelioma), mesothelioma, pancreatic cancer (e.g., pancreatic duct cancer, pancreatic endocrine tumor), pharyngeal cancer, laryngeal cancer, esophagus cancer, gastric cancer (e.g., papillary adenocarcinoma, mucinous adenocarcinoma, adenosquamous carcinoma), duodenal cancer, small intestinal cancer, breast cancer (e.g., invasive ductal carcinoma, ductal carcinoma in situ, inflammatory breast cancer), ovarian cancer (e.g., ovarian epithelial carcinoma, extragonadal germ cell tumor, ovarian germ cell tumor, ovarian low malignant potential tumor), testis tumor, prostate cancer (e.g., hormone-dependent prostate cancer, non-hormone dependent prostate cancer, castration-resistant prostate cancer), liver cancer (e.g., hepatoma, primary liver cancer, extrahepatic bile duct cancer), thyroid cancer (e.g., medullary thyroid carcinoma), renal cancer (e.g., renal cell carcinoma (e.g., clear cell renal cell carcinoma), transitional cell carcinoma of renal pelvis and ureter), uterine cancer (e.g., cervical cancer, uterine body cancer, uterus sarcoma), gestational choriocarcinoma, brain tumor (e.g., medulloblastoma, glioma, pineal astrocytoma, pilocytic astrocytoma, diffuse astrocytoma, anaplastic astrocytoma, hypophyseal adenoma), retinoblastoma, skin cancer (e.g., basal cell carcinoma, malignant melanoma, melanoma), sarcoma (e.g., rhabdomyosarcoma, leiomyosarcoma, soft tissue sarcoma, spindle cell sarcoma, osteosarcoma), fibrosarcoma, malignant bone tumor, urinary bladder cancer, hematologic cancer (e.g., multiple myeloma, leukemia, acute myeloid leukemia (AML), acute lymphoblastic leukemia (ALL), including blast crisis of chronic leukemia), malignant lymphoma, Hodgkin's disease, chronic myeloproliferative disease), cancer of unknown primary nucleus], cancer growth inhibitor, cancer metastasis inhibitor, apoptosis promoter, and for the prophylaxis or treatment of precancerous lesion (e.g., bone marrow myelodysplastic syndrome).

Also described herein, in one embodiment, is a method of treating a disease caused by a dysregulation of an integrated stress response in a patient in need thereof, comprising administering to the patient a therapeutically effective amount of a compound described herein (e.g., a compound of Formulae I-A, I-B, I-C, and I-D described herein), or a pharmaceutically acceptable salt thereof, or of a pharmaceutical composition described herein. In some embodiments, the dysregulation of the integrated stress response and/or the unfolded protein response is caused by GCN2 kinase. In some embodiments, the dysregulation of the integrated stress response and/or the unfolded protein response is caused by PERK kinase. In some embodiments, the dysregulation of the integrated stress response is caused by GCN2 kinase. In some embodiments, the dysregulation of the unfolded protein response is caused by PERK kinase. In some embodiments, the dysregulation of the integrated stress response is caused by activation of a kinase selected from the group consisting of PERK kinase and GCN2 kinase. In some embodiments, the dysregulation of the integrated stress response is caused by activation of GCN2 kinase. In some embodiments, the dysregulation of the integrated stress response is caused by activation of PERK kinase.

Also described herein, in one embodiment, is a method of treating a disease caused by a dysregulation of an integrated stress response and/or an unfolded protein response in a patient in need thereof, comprising administering to the patient a therapeutically effective amount of a compound described herein (e.g., a compound of Formulae I-A, I-B, I-C, and I-D described herein), or a pharmaceutically acceptable salt thereof, or of a pharmaceutical composition described herein. In some embodiments, the dysregulation of the integrated stress response and/or the unfolded protein response is caused by activation of a kinase selected from the group consisting of PERK kinase and GCN2 kinase. In some embodiments, the dysregulation of the integrated stress response is caused by activation of GCN2 kinase. In some embodiments, the dysregulation of the unfolded protein response is caused by activation of PERK kinase.

In another embodiment, described herein is a method of modulating the activity of GCN2 kinase in a patient in need thereof, comprising administering to the patient a therapeutically effective amount of a compound described herein, or a pharmaceutically acceptable salt thereof, or of a pharmaceutical composition described herein.

In another embodiment, described herein is a method of activating GCN2 kinase in a patient in need thereof, comprising administering to the patient a therapeutically effective amount of a compound described herein, or a pharmaceutically acceptable salt thereof, or of a pharmaceutical composition described herein.

In another embodiment, described herein is a method of modulating the activity of PERK kinase in a patient in need thereof, comprising administering to the patient a therapeutically effective amount of a compound described herein, or a pharmaceutically acceptable salt thereof, or of a pharmaceutical composition described herein.

In another embodiment, described herein is a method of activating PERK kinase in a patient in need thereof, comprising administering to the patient a therapeutically effective amount of a compound described herein, or a pharmaceutically acceptable salt thereof, or of a pharmaceutical composition described herein.

In another embodiment, described herein is a method of inhibiting GCN2 kinase and inhibiting PERK kinase in a patient in need thereof, comprising administering to the patient a therapeutically effective amount of a compound described herein, or a pharmaceutically acceptable salt thereof, or of a pharmaceutical composition described herein.

In another embodiment, described herein is a method of modulating the activity of GCN2 kinase in a patient in need thereof, comprising administering to the patient a therapeutically effective amount of a compound described herein, or a pharmaceutically acceptable salt thereof, or of a pharmaceutical composition described herein.

In another embodiment, described herein is a method of inhibiting the activity of PERK kinase in a patient in need thereof, comprising administering to the patient a therapeutically effective amount of a compound described herein, or a pharmaceutically acceptable salt thereof, or of a pharmaceutical composition described herein.

In another embodiment, described herein is a method of treating a cancer in a patient in need thereof, comprising administering to the patient a therapeutically effective amount of a compound described herein (e.g., a compound of Formulae I-A, I-B, I-C, and I-D described herein), or a pharmaceutically acceptable salt thereof, or of a pharmaceutical composition described herein. In some embodiments, the cancer is selected from the group consisting of colorectal cancer, lung cancer, mesothelioma, pancreatic cancer, pharyngeal cancer, laryngeal cancer, esophagus cancer, gastric, duodenal cancer, small intestinal cancer, breast cancer, ovarian cancer, testis tumor, prostate, liver cancer, thyroid cancer, renal cancer, uterine cancer, gestational choriocarcinoma, brain tumor, retinoblastoma, skin cancer, melanoma, sarcoma, fibrosarcoma, malignant bone tumor, urinary bladder cancer, hematologic cancer, leukemia, acute myeloid leukemia, acute lymphoblastic leukemia, and malignant lymphoma. In some embodiments, the cancer is selected from the group consisting of colorectal cancer, lung cancer, mesothelioma, pancreatic cancer, pharyngeal cancer, laryngeal cancer, esophagus cancer, gastric, duodenal cancer, small intestinal cancer, breast cancer, ovarian cancer, testis tumor, prostate, liver cancer, thyroid cancer, renal cancer, uterine cancer, gestational choriocarcinoma, brain tumor, retinoblastoma, skin cancer, melanoma, sarcoma, fibrosarcoma, malignant bone tumor, urinary bladder cancer, hematologic cancer, leukemia, acute myeloid leukemia, acute lymphoblastic leukemia, chronic lymphocytic leukemia, chronic myeloid leukemia, multiple myeloma, B-cell lymphoma, Follicular lymphoma, mantle cell lymphoma, diffuse large B cell lymphoma, T-cell lymphoma, erythroleukemia, histocyctic lymphoma, waldenstrom macroglobulinemia, and malignant lymphoma. In some embodiments, the cancer is leukemia. In some embodiments, the cancer is acute myeloid leukemia. In some embodiments, the cancer is acute lymphoblastic leukemia. In some embodiments, the cancer is fibrosarcoma. In some embodiments, the cancer is multiple myeloma. In some embodiments, the cancer is lymphoma. In some embodiments, the cancer is B-cell lymphoma. In some embodiments, the cancer is T cell lymphoma.

In an embodiment, described herein is a method of treating amyloidosis in a patient in need thereof, comprising administering to the patient a compound described herein, or pharmaceutically acceptable salt thereof, or pharmaceutical composition described herein. In an embodiment, described herein is a method of treating light chain amyloidosis in a patient in need thereof, comprising administering to the patient a compound described herein, or pharmaceutically acceptable salt thereof, or pharmaceutical composition described herein.

In another embodiment, described herein is a method of treating a disease selected from a GCN2 associated disease and a PERK associated disease, in a patient in need thereof, comprising administering to the patient a therapeutically effective amount of a compound described herein (e.g., a compound of Formulae I-A, I-B, I-C, and I-D described herein), or a pharmaceutically acceptable salt thereof, or of a pharmaceutical composition described herein. In some embodiments, the disease is a GCN2 associated disease. In some embodiments, the disease is a PERK associated disease. In some embodiments, the disease is a cancer. In some embodiments, the cancer is selected from the group consisting of colorectal cancer, lung cancer, mesothelioma, pancreatic cancer, pharyngeal cancer, laryngeal cancer, esophagus cancer, gastric, duodenal cancer, small intestinal cancer, breast cancer, ovarian cancer, testis tumor, prostate, liver cancer, thyroid cancer, renal cancer, uterine cancer, gestational choriocarcinoma, brain tumor, retinoblastoma, skin cancer, melanoma, sarcoma, fibrosarcoma, malignant bone tumor, urinary bladder cancer, hematologic cancer, leukemia, acute myeloid leukemia, acute lymphoblastic leukemia, and malignant lymphoma. In some embodiments, the cancer is selected from the group consisting of colorectal cancer, lung cancer, mesothelioma, pancreatic cancer, pharyngeal cancer, laryngeal cancer, esophagus cancer, gastric, duodenal cancer, small intestinal cancer, breast cancer, ovarian cancer, testis tumor, prostate, liver cancer, thyroid cancer, renal cancer, uterine cancer, gestational choriocarcinoma, brain tumor, retinoblastoma, skin cancer, melanoma, sarcoma, fibrosarcoma, malignant bone tumor, urinary bladder cancer, hematologic cancer, leukemia, acute myeloid leukemia, acute lymphoblastic leukemia, chronic lymphocytic leukemia, chronic myeloid leukemia, multiple myeloma, B-cell lymphoma, Follicular lymphoma, mantle cell lymphoma, diffuse large B cell lymphoma, T-cell lymphoma, erythroleukemia, histocyctic lymphoma, waldenstrom macroglobulinemia, and malignant lymphoma. In some embodiments, the cancer is leukemia. In some embodiments, the cancer is acute myeloid leukemia. In some embodiments, the cancer is acute lymphoblastic leukemia. In some embodiments, the cancer is fibrosarcoma. In some embodiments, the cancer is multiple myeloma. In some embodiments, the cancer is lymphoma. In some embodiments, the cancer is B-cell lymphoma. In some embodiments, the cancer is T cell lymphoma. In some embodiments, the disease is amyloidosis. In some embodiments, the disease is light chain amyloidosis.

In another embodiment, described herein is a method of treating a disease selected from a GCN2 associated disease and a PERK associated disease, in a patient in need thereof, comprising administering to the patient a therapeutically effective amount of a compound described herein (e.g., a compound of Formulae I-A, I-B, I-C, and I-D described herein), or a pharmaceutically acceptable salt thereof, and a therapeutically effective amount of one or more therapeutic agents. In some embodiments, the disease is a GCN2 associated disease. In some embodiments, the disease is a PERK associated disease. In some embodiments, the disease is a cancer. In some embodiments, the cancer is selected from the group consisting of colorectal cancer, lung cancer, mesothelioma, pancreatic cancer, pharyngeal cancer, laryngeal cancer, esophagus cancer, gastric, duodenal cancer, small intestinal cancer, breast cancer, ovarian cancer, testis tumor, prostate, liver cancer, thyroid cancer, renal cancer, uterine cancer, gestational choriocarcinoma, brain tumor, retinoblastoma, skin cancer, melanoma, sarcoma, fibrosarcoma, malignant bone tumor, urinary bladder cancer, hematologic cancer, leukemia, acute myeloid leukemia, acute lymphoblastic leukemia, and malignant lymphoma. In some embodiments, the cancer is selected from the group consisting of colorectal cancer, lung cancer, mesothelioma, pancreatic cancer, pharyngeal cancer, laryngeal cancer, esophagus cancer, gastric, duodenal cancer, small intestinal cancer, breast cancer, ovarian cancer, testis tumor, prostate, liver cancer, thyroid cancer, renal cancer, uterine cancer, gestational choriocarcinoma, brain tumor, retinoblastoma, skin cancer, melanoma, sarcoma, fibrosarcoma, malignant bone tumor, urinary bladder cancer, hematologic cancer, leukemia, acute myeloid leukemia, acute lymphoblastic leukemia, chronic lymphocytic leukemia, chronic myeloid leukemia, multiple myeloma, B-cell lymphoma, Follicular lymphoma, mantle cell lymphoma, diffuse large B cell lymphoma, T-cell lymphoma, erythroleukemia, histocyctic lymphoma, waldenstrom macroglobulinemia, and malignant lymphoma. In some embodiments, the cancer is leukemia. In some embodiments, leukemia is acute myeloid leukemia. In some embodiments, leukemia is acute lymphoblastic leukemia. In some embodiments, the cancer is fibrosarcoma. In some embodiments, the cancer is multiple myeloma. In some embodiments, the cancer is lymphoma. In some embodiments, the cancer is B-cell lymphoma. In some embodiments, the cancer is T cell lymphoma. In some embodiments, the disease is amyloidosis. In some embodiments, the disease is light chain amyloidosis. In some embodiments, the one or more therapeutic agents is selected from the group consisting of L-asparaginase, pegylated asparaginase, a PERK inhibitor, a mTOR inhibitor, an immunomodulatory agent, a MAPK pathway inhibitor, a MEK inhibitor, an ERK inhibitor, and a Ras inhibitor. In some embodiments, the one or more therapeutic agents is selected from the group consisting of an IMiD agent, a proteasome inhibitor, a steroid, an anti-CD38 agent, an anti-CD20 agent, a Bcl-2 inhibitor, a PI3K inhibitor, a Bi-specific antibody, a nucleoside analog, a BTK inhibitor, a DNA alkylating agent, an EZH2 inhibitor, an anthracycline, a topoisomerase inhibitor, a platin, a tyrosine kinase inhibitor, an HDAC inhibitor, a nuclear export inhibitor, an anti-microtubule agent L-asparaginase, pegylated asparaginase, a PERK inhibitor, a mTOR inhibitor, an immunomodulatory agent, a MAPK pathway inhibitor, a MEK inhibitor, an ERK inhibitor, and a Ras inhibitor. In some embodiments, the one or more therapeutic agents is selected from the group consisting of L-asparaginase, pegaspargase, calaspargase pegol-mnkl, bortezomib, carfilzomib, ixazomib, thalidomide, pomalidomide, lenalidomide, dexamethasone, prednisone, daratumumab, daratumumab/hyaluronidase, isatuximab, rituximab, obinutuzumab, venetoclax, idelalisib, copanlisib, duvelisib, umbralisib, gemcitabine, cytarabine, ibrutinib, acalabrutinib, zanubrutinib, bendamustine, cyclophosphamide, tazemetostat, doxorubicin, daunorubicin, etoposide, oxaloplatin, carboplatin, cisplatinbosutinib, dasatinib, imatinib, nilotinib, ponatinib, panobinostat, selinexor, vincristine, JZP-458, eryaspase, PF745 (JZP-341), asparaginase *Erwinia chrysanthemi* (crisantaspase), *Escherichia coli* asparaginase (colaspase), an anti-PD1 agent, an anti-PDL1 agent, and an anti-CTLA4 agent.

In an embodiment, described herein is a compound described herein, or a pharmaceutically acceptable salt thereof, or the pharmaceutical composition described herein, for use in treating a disease caused by a dysregulation of an integrated stress response and/or the unfolded protein response in a patient in need thereof. In some embodiments, the dysregulation of the integrated stress response and/or the unfolded protein response is caused by a kinase selected from the group consisting of PERK kinase and GCN2 kinase. In some embodiments, the dysregulation of the integrated stress response and/or the unfolded protein response is caused by GCN2 kinase. In some embodiments, the dysregulation of the integrated stress response and/or the unfolded protein response is caused by PERK kinase. In some embodiments, the dysregulation of the integrated stress response is caused by GCN2 kinase. In some embodiments, the dysregulation of the unfolded protein response is caused by PERK kinase. In some embodiments, the dysregulation of the integrated stress response is caused by activation of a kinase selected from the group consisting of PERK kinase and GCN2 kinase. In some embodiments, the dysregulation of the integrated stress response is caused by activation of GCN2 kinase. In some embodiments, the dysregulation of the integrated stress response is caused by activation of PERK kinase. In an embodiment, described herein is a compound described herein, or a pharmaceutically acceptable salt thereof, or the pharmaceutical composition described herein, for use in modulating the activity of GCN2 kinase in a patient in need thereof. In an embodiment, described herein is a compound described herein, or a pharmaceutically acceptable salt thereof, or the pharmaceutical composition described herein, for use in activating GCN2 kinase in a patient in need thereof. In an embodiment, described herein is a compound described herein, or a pharmaceutically acceptable salt thereof, or the pharmaceutical composition described herein, for use in modulating the activity of PERK kinase in a patient in need thereof. In an embodiment, described herein is a compound described herein, or a pharmaceutically acceptable salt thereof, or the pharmaceutical composition described herein, for use in activating PERK kinase in a patient in need thereof.

In an embodiment, described herein is a compound described herein, or a pharmaceutically acceptable salt thereof, or the pharmaceutical composition described herein, for use in inhibiting GCN2 kinase and inhibiting PERK kinase in a patient in need thereof. In an embodiment, described herein is a compound described herein, or a pharmaceutically acceptable salt thereof, or the pharmaceutical composition described herein, for use in modulating the activity of GCN2 kinase in a patient in need thereof. In another embodiment, described herein is a compound described herein, or a pharmaceutically acceptable salt thereof, or the pharmaceutical composition described herein, for use in inhibiting the activity of PERK kinase in a patient in need thereof.

In an embodiment, described herein is a compound described herein, or a pharmaceutically acceptable salt thereof, or the pharmaceutical composition described herein, for use in treating a cancer in a patient in need thereof. In some embodiments, the cancer is selected from the group consisting of colorectal cancer, lung cancer, mesothelioma, pancreatic cancer, pharyngeal cancer, laryngeal cancer, esophagus cancer, gastric, duodenal cancer, small intestinal cancer, breast cancer, ovarian cancer, testis tumor, prostate, liver cancer, thyroid cancer, renal cancer, uterine cancer, gestational choriocarcinoma, brain tumor, retinoblastoma, skin cancer, melanoma, sarcoma, fibrosarcoma, malignant bone tumor, urinary bladder cancer, hematologic cancer, leukemia, acute myeloid leukemia, acute lymphoblastic leukemia, chronic lymphocytic leukemia, chronic myeloid leukemia, multiple myeloma, B-cell lymphoma, follicular lymphoma, mantle cell lymphoma, diffuse large B cell lymphoma, T-cell lymphoma, erythroleukemia, histocytic lymphoma, waldenstrom macroglobulinemia, and malignant lymphoma. In some embodiments, the cancer is leukemia. In some embodiments, the cancer is acute myeloid leukemia. In some embodiments, the cancer is acute lymphoblastic leukemia. In some embodiments, the cancer is fibrosarcoma. In some embodiments, the cancer is multiple myeloma. In some embodiments, the cancer is lymphoma. In some embodiments, the cancer is B-cell lymphoma. In some embodiments, the cancer is T cell lymphoma.

In an embodiment, described herein is a compound described herein, or a pharmaceutically acceptable salt thereof, or the pharmaceutical composition described herein, for use in treating amyloidosis in a patient in need thereof. In an embodiment, described herein is a compound described herein, or a pharmaceutically acceptable salt thereof, or the pharmaceutical composition described herein, for use in treating light chain amyloidosis in a patient in need thereof.

In an embodiment, described herein is a compound described herein, or a pharmaceutically acceptable salt thereof, or the pharmaceutical composition described herein, for use in treating a disease selected from a GCN2 associated disease and a PERK associated disease, in a patient in need thereof. In some embodiments, the disease is a GCN2 associated disease. In some embodiments, the disease is a PERK associated disease. In some embodiments, the disease is a cancer. In some embodiments, the cancer is selected from the group consisting of colorectal cancer, lung cancer, mesothelioma, pancreatic cancer, pharyngeal cancer, laryngeal cancer, esophagus cancer, gastric, duodenal cancer, small intestinal cancer, breast cancer, ovarian cancer, testis tumor, prostate, liver cancer, thyroid cancer, renal cancer, uterine cancer, gestational choriocarcinoma, brain tumor, retinoblastoma, skin cancer, melanoma, sarcoma, fibrosarcoma, malignant bone tumor, urinary bladder cancer, hematologic cancer, leukemia, acute myeloid leukemia, acute lymphoblastic leukemia, chronic lymphocytic leukemia, chronic myeloid leukemia, multiple myeloma, B-cell lymphoma, follicular lymphoma, mantle cell lymphoma, diffuse large B cell lymphoma, T-cell lymphoma, erythroleukemia, histocyctic lymphoma, waldenstrom macroglobulinemia, and malignant lymphoma. In some embodiments, the cancer is leukemia. In some embodiments, the cancer is acute myeloid leukemia. In some embodiments, the cancer is acute lymphoblastic leukemia. In some embodiments, the cancer is fibrosarcoma. In some embodiments, the cancer is multiple myeloma. In some embodiments, the cancer is lymphoma. In some embodiments, the cancer is B-cell lymphoma. In some embodiments, the cancer is T cell lymphoma. In some embodiments, the disease is amyloidosis. In some embodiments, the disease is light chain amyloidosis.

In an embodiment, described herein is a compound described herein, or a pharmaceutically acceptable salt thereof, or the pharmaceutical composition described herein, for use in treating a disease selected from a GCN2 associated disease and a PERK associated disease, in a patient in need thereof. In some embodiments, the disease is a GCN2 associated disease. In some embodiments, the disease is a PERK associated disease. In some embodiments, the disease is a cancer. In some embodiments, the cancer is selected from the group consisting of colorectal cancer, lung cancer, mesothelioma, pancreatic cancer, pharyngeal cancer, laryngeal cancer, esophagus cancer, gastric, duodenal cancer, small intestinal cancer, breast cancer, ovarian cancer, testis tumor, prostate, liver cancer, thyroid cancer, renal cancer, uterine cancer, gestational choriocarcinoma, brain tumor, retinoblastoma, skin cancer, melanoma, sarcoma, fibrosarcoma, malignant bone tumor, urinary bladder cancer, hematologic cancer, leukemia, acute myeloid leukemia, acute lymphoblastic leukemia, chronic lymphocytic leukemia, chronic myeloid leukemia, multiple myeloma, B-cell lymphoma, follicular lymphoma, mantle cell lymphoma, diffuse large B cell lymphoma, T-cell lymphoma, erythroleukemia, histocyctic lymphoma, waldenstrom macroglobulinemia, and malignant lymphoma. In some embodiments, the cancer is leukemia. In some embodiments, leukemia is acute myeloid leukemia. In some embodiments, leukemia is acute lymphoblastic leukemia. In some embodiments, the cancer is fibrosarcoma. In some embodiments, the cancer is multiple myeloma. In some embodiments, the cancer is lymphoma. In some embodiments, the cancer is B-cell lymphoma. In some embodiments, the cancer is T cell lymphoma. In some embodiments, the disease is amyloidosis. In some embodiments, the disease is light chain amyloidosis. In some embodiments, the one or more therapeutic agents is selected from the group consisting of an IMiD agent, a proteasome inhibitor, a steroid, an anti-CD38 agent, an anti-CD20 agent, a Bcl-2 inhibitor, a PI3K inhibitor, a Bi-specific antibody, a nucleoside analog, a BTK inhibitor, a DNA alkylating agent, an EZH2 inhibitor, an anthracycline, a topoisomerase inhibitor, a platin, a tyrosine kinase inhibitor, an HDAC inhibitor, a nuclear export inhibitor, an anti-microtubule agent, L-asparaginase, pegylated asparaginase, a PERK inhibitor, a mTOR inhibitor, an immunomodulatory agent, a MAPK pathway inhibitor, a MEK inhibitor, an ERK inhibitor, and a Ras inhibitor. In some embodiments, the one or more therapeutic agents is selected from the group consisting of bortezomib, carfilzomib, ixazomib, thalidomide, pomalidomide, lenalidomide, dexamethasone, prednisone, daratumumab, daratumumab/hyaluronidase, isatuximab, rituximab, obinutuzumab, venetoclax, idelalisib, copanlisib, duvelisib, umbralisib, gemcitabine, cytarabine, ibrutinib, acalabrutinib, zanubrutinib, bendamustine, cyclophosphamide, tazemetostat, doxorubicin, daunorubicin, etoposide, oxaloplatin, carboplatin, cisplatinbosutinib, dasatinib, imatinib, nilotinib, ponatinib, panobinostat, selinexor, vincristine, L-asparaginase, pegaspargase, calaspargase pegol-mnkl, JZP-458, eryaspase, PF745 (JZP-341), asparaginase *Erwinia chrysanthemi* (crisantaspase), *Escherichia coli* asparaginase (colaspase), anti-PD1, anti-PDL1 and anti-CTLA4.

The compounds provided herein may be administered to patients (animals and humans) in need of such treatment in dosages that will provide optimal pharmaceutical efficacy. It will be appreciated that the dose required for use in any particular application will vary from patient to patient, not only with the particular compound or composition selected, but also with the route of administration, the nature of the condition being treated, the age and condition of the patient, concurrent medication or special diets then being followed by the patient, and other factors which those skilled in the art will recognize, with the appropriate dosage ultimately being at the discretion of the attendant physician. For treating clinical conditions and diseases noted above, a compound provided herein may be administered orally, subcutaneously, topically, parenterally, by inhalation spray or rectally in dosage unit formulations containing conventional non-toxic pharmaceutically acceptable carriers, adjuvants and vehicles. Parenteral administration may include subcutaneous injections, intravenous or intramuscular injections or infusion techniques.

Treatment can be continued for as long or as short a period as desired. The compositions may be administered on a regimen of, for example, one to four or more times per day. A suitable treatment period can be, for example, at least about one week, at least about two weeks, at least about one month, at least about six months, at least about 1 year, or indefinitely. A treatment period can terminate when a desired result is achieved.

Combination Therapy

Compounds described herein, e.g., a compound of Formula I as defined herein, can be administered in combination with one or more additional therapeutic agents to treat a disorder described herein, such as a cancer described herein. For example, provided in the present disclosure is a pharmaceutical composition comprising a compound described herein, e.g., a compound of Formula I as defined herein, one or more additional therapeutic agents, and a pharmaceutically acceptable excipient. In some embodiments, a compound of Formula I as defined herein, and one additional therapeutic agent is administered. In some embodiments, a compound of Formula I as defined herein, and two additional therapeutic agents are administered. In some embodiments, a compound of Formula I as defined herein, and three additional therapeutic agents are administered. Combination therapy can be achieved by administering two or more therapeutic agents, each of which is formulated and administered separately. For example, a compound of Formula I as defined herein, and an additional therapeutic agent can be formulated and administered separately. Combination therapy can also be achieved by administering two or more therapeutic agents in a single formulation, for example a pharmaceutical composition comprising a compound of Formula I as one therapeutic agent and one or more additional therapeutic agents such as a chemotherapeutic agent. For example, a compound of Formula I as defined herein, and an additional therapeutic agent can be administered in a single formulation. Other combinations are also encompassed by combination therapy. While the two or more agents in the combination therapy can be administered simultaneously, they need not be. For example, administration of a first agent (or combination of agents) can precede administration of a second agent (or combination of agents) by minutes, hours, days, or weeks. Thus, the two or more agents can be administered within minutes of each other or within 1, 2, 3, 6, 9, 12, 15, 18, or 24 hours of each other or within 1, 2, 3, 4, 5, 6, 7, 8, 9, 10, 12, 14 days of each other or within 2, 3, 4, 5, 6, 7, 8, 9, or weeks of each other. In some cases, even longer intervals are possible. While in many cases it is desirable that the two or more agents used in a combination therapy be present in within the patient's body at the same time, this need not be so.

Combination therapy can also include two or more administrations of one or more of the agents used in the combination using different sequencing of the component agents. For example, if agent X and agent Y are used in a combination, one could administer them sequentially in any combination one or more times, e.g., in the order X-Y-X, X-X-Y, Y-X-Y, Y-Y-X, X-X-Y-Y, etc.

Combination therapy can also include two or more administrations of one or more of the agents used in the combination using different routes of administration. Each of the one or more of the agents may be independently administered orally, subcutaneously, topically, parenterally, by inhalation spray or rectally in dosage unit formulations containing conventional non-toxic pharmaceutically acceptable carriers, adjuvants and vehicles. Parenteral administration may include subcutaneous injections, intravenous or intramuscular injections or infusion techniques.

In some embodiments, the compounds of Formula I as described herein, are combined with asparaginase (ASNase, L-asparaginase) or its derivatives. In some embodiments, asparaginase is obtained from *Erwinia chrysanthemi* and is known as crisantaspase or asparaginase *Erwinia chrysanthemi*. Asparaginase *Erwinia chrysanthemi* is sold under the trademarks Erwinaze® or Erwinase®. In some embodiments, asparaginase is obtained from *Escherichia coli* and is known as colaspase. Colaspase is sold under the trademarks Elspar®, Leunase®, Kidrolase®, or Spectrila® (recombinant *E. coli* aparaginase). Pegylated derivatives of colaspase are pegaspargase, sold under the trademark Oncaspar®, and calaspargase pegol-mnkl, sold under the trademark Asparlas®. Other asparaginase products currently in preclinical or clinical development include JZP-458 (recombinant *Erwinia* asparaginase), PF745 (JZP-341), eryaspase (GRASPA®), and Xoncane.

In some embodiments, the compounds of Formula I as defined herein, are combined with an immunomodulatory agent. In some embodiments, the immunomodulatory enhances the adaptive immune response. In some embodiments, the immunomodulatory enhances the activity of antigen-presenting cells. In some embodiments, the immunomodulatory agent enhances the anti-tumor activity of myeloid cells including macrophages. In some embodiments, the immunomodulatory enhances the anti-tumor activity of Natural Killer cells. In some embodiments, the immunomodulatory agent enhances the activity of effector T Cells, including cytotoxic T Cells.

In some embodiments, the one or more additional therapeutic agents that may be administered in combination with a compound provided herein can be a MAPK pathway inhibitor. Such MAPK pathway inhibitors include, for example, MEK inhibitors, ERK inhibitors, and Ras inhibitors.

Exemplary MEK inhibitors include, but are not limited to, trametinib, selumetinib, cobimetinib, binimetinib, and pharmaceutically acceptable salts thereof. Exemplary ERK inhibitors include, but are not limited to, include, but are not limited to, ulixertinib, SCH772984, LY3214996, ravoxertinib, VX-Ile, ASN-007, GDC-0994, MK-8353, ASTX-029, LTT462, KO-947, and pharmaceutically acceptable salts thereof. Exemplary Ras inhibitors include, but are not limited to, AMG-510, MRTX849, ARS-1620, ARS-3248, LY3499446, and pharmaceutically acceptable salts thereof.

In some embodiments, the additional therapeutic agents can be immunomodulatory agents including but not limited to anti-PD-1 or anti-PDL-1 therapeutics including pembrolizumab, nivolumab, pidilizumab, cemiplimab, atezolizumab, durvalumab, BMS-936559, or avelumab. In some embodiments, the additional therapeutic agents can be anti-TIM3 (anti-HAVcr2) therapeutics including but not limited to TSR-022 or MBG453, anti-LAG3 therapeutics including but not limited to relatlimab, LAG525, or TSR-033, anti-4-1BB (anti-CD37, anti-TNFRSF9), CD40 agonist therapeutics including but not limited to SGN-40, CP-870,893 or RO7009789, anti-CD47 therapeutics including but not limited to Hu5F9-G4, anti-CD20 therapeutics, anti-CD38 therapeutics, STING agonists including but not limited to ADU-S100, MK-1454, ASA404, or amidobenzimidazoles. In some embodiments, the additional therapeutic agents can be anti-CTLA4 agents including ipilimumab, tremelimumab. In some embodiments, the additional therapeutic agents can be hypomethylating agents including but not limited to azacytidine or decitabine, other immunomodulatory therapeutics including but not limited to epidermal growth factor inhibitors, statins, metformin, angiotensin receptor blockers, thalidomide, lenalidomide, pomalidomide, prednisone, or dexamethasone. In some embodiments, the additional therapeutic agents can be immunotherapeutic agents including targeted therapeutic agents, cancer vaccines, and CAR-T cell therapy.

The compounds of Formula I as described herein may be administered in combination with other therapeutic agents known to treat cancers. Such other therapeutic agents include radiation therapy, anti-tubulin agents, DNA alkylating agents, DNA synthesis-inhibiting agents, DNA intercalating agents, anti-estrogen agents, anti-androgens, steroids, anti-EGFR agents, kinase inhibitors, mTOR inhibitors, PI3 kinase inhibitors, cyclin-dependent kinase inhibitors, CD4/CD6 kinase inhibitors, topoisomerase inhibitors, Histone Deacetylase (HDAC) inhibitors, DNA methylation inhibitors, anti-HER2 agents, anti-angiogenic agents, proteasome inhibitors, PARP (poly ADP ribose polymerase) inhibitors, cell cycle regulating kinase inhibitors, thalidomide, lenalidomide, pomalidomide, bortezomib, carfilzomib, ixazomib, daratumumab, daratumumab/hyaluronidase, isatuximab, dexamethasone, and antibody-drug-conjugates (ADCs).

In an embodiment, the additional therapeutic agents can be chemotherapeutic agents including but not limited to an anti-tubulin agents (for example, paclitaxel, paclitaxel protein-bound particles for injectable suspension including nab-paclitaxel, eribulin, docetaxel, ixabepilone, vincristine, auristatins, or maytansinoids), vinorelbine, DNA-alkylating agents (including cisplatin, carboplatin, oxaliplatin, cyclophosphamide, ifosfamide, temozolomide), DNA intercalating agents or DNA topoisomerase inhibitors (including anthracyclines such as doxorubicin, pegylated liposomal doxorubicin, daunorubicin, idarubicin, mitoxantrone, or epirubicin, camptothecins such as topotecan, irinotecan, or exatecan), 5-fluorouracil, capecitabine, cytarabine, decitabine, 5-aza cytadine, gemcitabine and methotrexate.

In some embodiments, the additional therapeutic agents can be kinase inhibitors including but not limited to erlotinib, gefitinib, neratinib, afatinib, osimertinib, lapatanib, crizotinib, brigatinib, ceritinib, alectinib, lorlatinib, everolimus, temsirolimus, abemaciclib, LEE011, palbociclib, cabozantinib, ripretinib, sunitinib, pazopanib, sorafenib, regorafenib, sunitinib, axitinib, dasatinib, imatinib, nilotinib, idelalisib, ibrutinib, BLU-667, Loxo 292, larotrectinib, and quizartinib, In some embodiments, the additional therapeutic agents can be anti-estrogen agents including but not limited to tamoxifen, fulvestrant, anastrozole, letrozole, and exemestane, anti-androgen agents including but not limited to abiraterone acetate, enzalutamide, nilutamide, bicalutamide, flutamide, cyproterone acetate, steroid agents including but not limited to prednisone and dexamethasone, PARP inhibitors including but not limited to neraparib, olaparib, talazoparib, and rucaparib, topoisomerase I inhibitors including but not limited to irinotecan, camptothecin, exatecan, and topotecan, topoisomerase II inhibitors including but not limited to anthracyclines, etoposide, etoposide phosphate, and mitoxantrone, Histone Deacetylase (HDAC) inhibitors including but not limited to vorinostat, romidepsin, panobinostat, valproic acid, and belinostat, DNA methylation inhibitors including but not limited to DZNep and 5-aza-2'-deoxycytidine, proteasome inhibitors including but not limited to bortezomib and carfilzomib, biological agents including but not limited to trastuzumab, ado-trastuzumab, pertuzumab, cetuximab, and panitumumab.

In some embodiments, the additional therapeutic agents can be anti-angiogenic agents including bevacizumab, aflibercept, and AMG386.

In some embodiments, the additional therapeutic agents can be antibody-drug-conjugates (ADCs) including DM1, DM4, MMAE, MMAF, or camptothecin payloads, brentuximab vedotin and trastuzumab emtansine, radiotherapy, therapeutic vaccines including but not limited to sipuleucel-T.

In some embodiments, the additional therapeutic agent can be an autophagy inhibitor including ULK inhibitors, VPS34 inhibitors, PIKfyve inhibitors, PPT1 inhibitors, or lysosomal blocking agents. In some embodiments, the additional therapeutic agent can be DCC-3116, SAR405, SB02024, hydroxychloroquinine, chloroquine, apilimod, MRT403, and LYS05.

In some embodiments, the additional therapeutic agent is selected from a luteinizing hormone-releasing hormone (LHRH) analog, including goserelin and leuprolide.

In some embodiments, the additional therapeutic agent is selected from the group consisting of everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, pemetrexed, erlotinib, dasatanib, nilotinib, decatanib, panitumumab, amrubicin, oregovomab, Lep-etu, nolatrexed, AZD 2171, batabulin, of atumtunab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, $IPdR_1$ KRX-0402, lucanthone, LY 317615, neuradiab, vitespan, Rta 744, alanosine (Sdx 102), talampanel, atrasentan, XR 311, romidepsin, ADS-100380, sunitinib, 5-fluorouracil, vorinostat, etoposide, gemcitabine, doxorubicin, irinotecan, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo[2,3-d]pyrimidin-5-yl)-ethyl]benzoyl]-, disodium salt, heptahydrate, camptothecin, PEG-labeled irinotecan, tamoxifen, toremifene citrate, anastrazole, exemestane, letrozole, DES (diethylstilbestrol), estradiol, estrogen, conjugated estrogen, bevacizumab, IMC-1C11, CHIR-258, 345-(methylsulfonylpiperadinemethyl)-indolylj-quinolone, vatalanib, AG-013736, AVE-0005, the acetate salt of [D-Ser(tBu) 6, Azgly 10] (pyro-Glu-His-Trp-Ser-Tyr-D-Ser(tBu)-Leu-Arg-Pro-Azgly-$NH_2$ acetate [$C_{59}H_{84}N_{18}O_{14}$—$(C_2H_4O_2)_x$ where x=1 to 2.4] (SEQ ID NO: 3), goserelin acetate, leuprolide acetate, triptorelin pamoate, medroxyprogesterone acetate, hydroxyprogesterone caproate, megestrol acetate, raloxifene, bicalutamide, flutanide, nilutamide, megestrol acetate, CP-724714; TAK-165, HKI-272, erlotinib, lapatanib, canertinib, ABX-EGF antibody, erbitux, EKB-569, PKI-166, GW-572016, ionafarnib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, amsacrine, anagrelide, L-asparaginase, Bacillus Calmette-Guerin (BCG) vaccine, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gemcitabine, gleevac, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, irinotecan, topotecan, doxorubicin, docetaxel, vinorelbine, bevacizumab (monoclonal antibody) and erbitux, cremophor-free paclitaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transsretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonist, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa and darbepoetin alfa, ipilumumab, and mixtures thereof.

Pharmaceutical Compositions and Kits

Another aspect of this disclosure provides pharmaceutical compositions comprising compounds as disclosed herein formulated together with a pharmaceutically acceptable carrier. In particular, the present disclosure provides pharmaceutical compositions comprising compounds as disclosed herein formulated together with one or more pharmaceutically acceptable carriers. These formulations include those suitable for oral, rectal, topical, buccal, parenteral (e.g., subcutaneous, intramuscular, intradermal, or intravenous) rectal, vaginal, or aerosol administration, although the most suitable form of administration in any given case will depend on the degree and severity of the condition being treated and on the nature of the particular compound being used. For example, disclosed compositions may be formulated as a unit dose, and/or may be formulated for oral or subcutaneous administration.

Exemplary pharmaceutical compositions may be used in the form of a pharmaceutical preparation, for example, in solid, semisolid or liquid form, which contains one or more of the compounds described herein, as an active ingredient, in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The active object compound is included in the pharmaceutical composition in an amount sufficient to produce the desired effect upon the process or condition of the disease.

For preparing solid compositions such as tablets, the principal active ingredient may be mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound provided herein, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules.

In solid dosage forms for oral administration (capsules, tablets, pills, dragees, powders, granules and the like), the subject composition is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the subject composition moistened with an inert liquid diluent. Tablets, and other solid dosage forms, such as dragees, capsules, pills and granules, may optionally be scored or prepared with coatings and shells, such as enteric coatings and other coatings well known in the pharmaceutical-formulating art.

Compositions for inhalation or insufflation include solutions and suspensions in pharmaceutically acceptable, aqueous or organic solvents, or mixtures thereof, and powders. Liquid dosage forms for oral administration include pharmaceutically acceptable emulsions, microemulsions, solutions, suspensions, syrups and elixirs. In addition to the subject composition, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, cyclodextrins and mixtures thereof.

Suspensions, in addition to the subject composition, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing a subject composition with one or more suitable non-irritating excipients or carriers comprising, for example, cocoa butter, polyethylene glycol, a suppository wax or a salicylate, and which is solid at room temperature, but liquid at body temperature and, therefore, will melt in the body cavity and release the active agent.

Dosage forms for transdermal administration of a subject composition include powders, sprays, ointments, pastes, creams, lotions, gels, solutions, patches and inhalants. The active component may be mixed under sterile conditions with a pharmaceutically acceptable carrier, and with any preservatives, buffers, or propellants which may be required.

The ointments, pastes, creams, and gels may contain, in addition to a subject composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays may contain, in addition to a subject composition, excipients such as lactose, talc, silicic acid, aluminum hydroxide, calcium silicates and polyamide powder, or mixtures of these substances. Sprays may additionally contain customary propellants, such as chlorofluorohydrocarbons and volatile unsubstituted hydrocarbons, such as butane and propane.

Compositions and compounds of the present disclosure may alternatively be administered by aerosol. This is accomplished by preparing an aqueous aerosol, liposomal preparation or solid particles containing the compound. A non-aqueous (e.g., fluorocarbon propellant) suspension could be used. Sonic nebulizers may be used because they minimize exposing the agent to shear, which may result in degradation of the compounds contained in the subject compositions. Ordinarily, an aqueous aerosol is made by formulating an aqueous solution or suspension of a subject composition together with conventional pharmaceutically acceptable carriers and stabilizers. The carriers and stabilizers vary with the requirements of the particular subject composition, but typically include non-ionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Pharmaceutical compositions of the present disclosure suitable for parenteral administration comprise a subject composition in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions provided herein include water, ethanol, polyols (such as glycerol, propylene glycol, polyethylene glycol, and the like), and suitable mixtures thereof, vegetable oils, such as olive oil, and injectable organic esters, such as ethyl oleate and cyclodextrins. Proper fluidity may be maintained, for example, by the use of coating materials, such as lecithin, by the maintenance of the required particle size in the case of dispersions, and by the use of surfactants.

In another embodiment, provided are enteral pharmaceutical formulations including a disclosed compound and an enteric material, and a pharmaceutically acceptable carrier or excipient thereof. Enteric materials refer to polymers that are substantially insoluble in the acidic environment of the stomach, and that are predominantly soluble in intestinal fluids at specific pHs. The small intestine is the part of the gastrointestinal tract (gut) between the stomach and the large intestine, and includes the duodenum, jejunum, and ileum. The pH of the duodenum is about 5.5, the pH of the jejunum is about 6.5 and the pH of the distal ileum is about 7.5.

Accordingly, enteric materials are not soluble, for example, until a pH of about 5.0, of about 5.2, of about 5.4, of about 5.6, of about 5.8, of about 6.0, of about 6.2, of about 6.4, of about 6.6, of about 6.8, of about 7.0, of about 7.2, of about 7.4, of about 7.6, of about 7.8, of about 8.0, of about 8.2, of about 8.4, of about 8.6, of about 8.8, of about 9.0, of about 9.2, of about 9.4, of about 9.6, of about 9.8, or of about 10.0. Exemplary enteric materials include cellulose acetate phthalate (CAP), hydroxypropyl methylcellulose phthalate (HPMCP), polyvinyl acetate phthalate (PVAP), hydroxypropyl methylcellulose acetate succinate (HPMCAS), cellulose acetate trimellitate, hydroxypropyl methylcellulose succinate, cellulose acetate succinate, cellulose acetate hexahydrophthalate, cellulose propionate phthalate, cellulose acetate maleate, cellulose acetate butyrate, cellulose acetate propionate, copolymer of methylmethacrylic acid and methyl methacrylate, copolymer of methyl acrylate, methylmethacrylate and methacrylic acid, copolymer of methylvinyl ether and maleic anhydride (Gantrez ES series), ethyl methyacrylate-methylmethacrylate-chlorotrimethylammonium ethyl acrylate copolymer, natural resins such as zein, shellac and copal collophorium, and several commercially available enteric dispersion systems (e.g., Eudragit L30D55, Eudragit FS30D, Eudragit L100, Eudragit S100, Kollicoat EMM30D, Estacryl 30D, Coateric, and Aquateric). The solubility of each of the above materials is either known or is readily determinable in vitro. The foregoing is a list of possible materials, but one of skill in the art with the benefit of the disclosure would recognize that it is not comprehensive and that there are other enteric materials that would meet the objectives described herein.

Advantageously, provided herein are kits for use by a e.g., a consumer in need of treatment of cancer. Such kits include a suitable dosage form such as those described above and instructions describing the method of using such dosage form to mediate, reduce or prevent inflammation. The instructions would direct the consumer or medical personnel to administer the dosage form according to administration modes known to those skilled in the art. Such kits could advantageously be packaged and sold in single or multiple kit units. An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc. . . . Second Week, Monday, Tuesday, . . . " etc. Other variations of memory aids will be readily apparent. A "daily dose" can be a single tablet or capsule or several pills or capsules to be taken on a given day. Also, a daily dose of a first compound can consist of one tablet or capsule while a daily dose of the second compound can consist of several tablets or capsules and vice versa. The memory aid should reflect this.

EXAMPLES

The compounds described herein can be prepared in a number of ways based on the teachings contained herein and disclosures of synthetic procedures in the art. In the description of the synthetic methods described below, it is to be understood that all proposed reaction conditions, including choice of solvent, reaction atmosphere, reaction temperature, duration of the experiment and workup procedures, can be chosen to be the conditions standard for that reaction, unless otherwise indicated. It is understood by one skilled in the art of organic synthesis that the functionality present on various portions of the molecule should be compatible with the reagents and reactions proposed. Substituents not compatible with the reaction conditions will be apparent to one skilled in the art, and alternate methods are therefore indicated. The starting materials for the examples are either commercially available or are readily prepared by standard methods from known materials.

The following abbreviation are used in this disclosure and have the following definitions: “AcOH’ is acetic acid, “ADP” is adenosine diphosphate, “Ar” is argon gas, “ASNase” is Asparaginase, “Boc” is t-butylcarbonate, “conc.” is concentrated, “$Cs_2CO_3$” is cesium carbonate, “DCM” is dichloromethane, “DIAD” is diisopropyl azodicarboxylate, “DIEA” is N,N-diisopropylethylamine, “DMF” is N,N-dimethylformamide, “dppf” is 1,1'-bis(diphenylphosphino)ferrocene, “DMSO” is dimethylsulfoxide, “EDTA” is ethylenediaminetetraacetic acid, “ESI” is electrospray ionization, “EtOAc” is ethyl acetate, “EtOH” is ethanol, “GST” is glutathione S-transferase, “h” is hour or hours, “HCl” is hydrochloric acid, “Hex” is hexane, “$H_2O$” is water, “$IC_{50}$” is half maximal inhibitory concentration, “$K_2CO_3$” is potassium carbonate, “KOAc” is potassium acetate, “$NaBH_4$” is sodium borohydride, “LAH” is lithium aluminum hydride, “$CH_3CN$” is acetonitrile, “mCPBA” is 4-chloroperbenzoic acid, “MeOH” is methanol, “MHz” is megahertz, “min” is minute or minutes, “MS” is mass spectrometry, “NADH” is nicotinamide adenine dinucleotide, “NaH” is sodium hydride, “$NaHCO_3$” is sodium bicarbonate, “$NaNO_2$” is sodium nitrite, “NaOMe” is sodium methoxide, “$Na_2SO_4$” is sodium sulfate, “NBS” is N-bromosuccinimide, “NCS” is N-chlorosuccinimide, “$NH_4Cl$” is ammonium chloride, “NIS” is N-iodosuccinimide, “NMR” is nuclear magnetic resonance, “PBS” is phosphate buffered saline, “$Pd_2(dba)_3$” is tris(dibenzylideneacetone)dipalladium(O), Pd(dppf)$Cl_2$" is 1,1-bis (diphenylphosphino)ferrocene-palladium(II)dichloride, “$Ph_3P$” is triphenylphosphine, “PMB” is paramethoxybenzyl, “$POCl_3$” is phosphorus oxychloride, “rt” is room temperature which is also known as “ambient temp,” which will be understood to consist of a range of normal laboratory temperatures ranging from 15-25° C., “sat’d.” is saturated, “SDS” is sodium dodecyl sulfate, “$SOCl_2$” is thionyl chloride, “TEA” is triethylamine, “TFA” is trifluoroacetic acid, “THF” is tetrahydrofuran, and “Xantphos” is 4,5-bis(diphenylphosphino)-9,9-dimethylxanthene.

General Chemistry

Exemplary compounds described herein are available by the general synthetic methods illustrated in the Schemes below, intermediate preparations, and the accompanying Examples.

Scheme 1

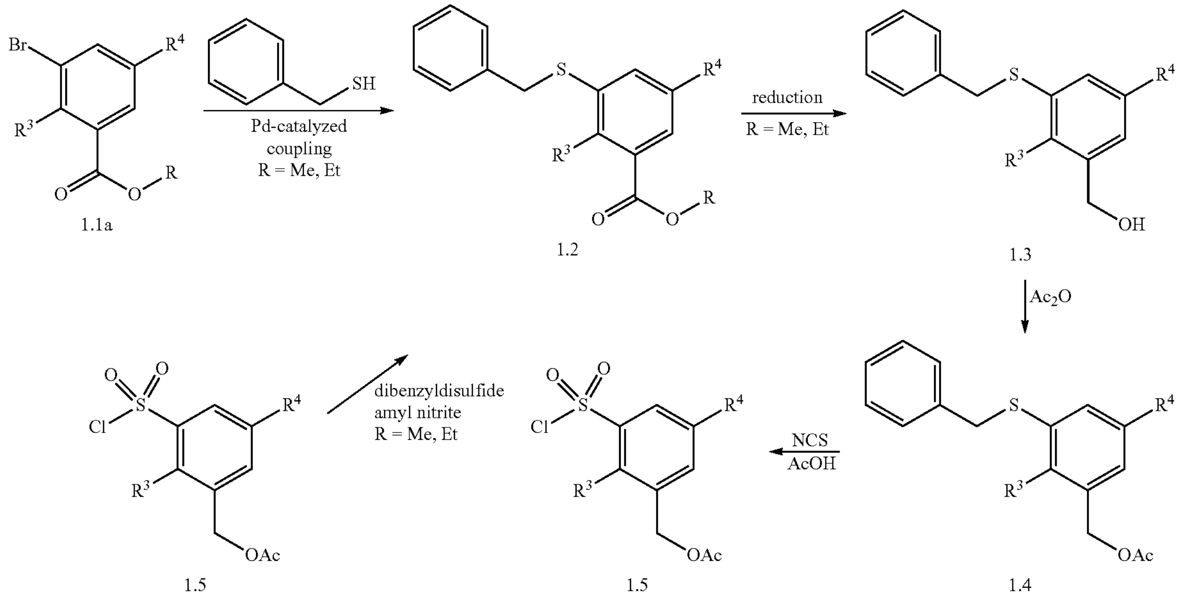

Scheme 1 illustrates an exemplary preparation of sulfonyl chlorides 1.5. Bromides 1.1a (commercially available or synthesized by those skilled in the art) are converted to thio-ethers 1.2 by a Pd catalyzed coupling reaction (for example, using $Pd_2(dba)_3$, XantPhos, phenylmethanthiol in the presence of a base, such as DIEA in a solvent such as toluene, and at elevated temperature). Alternatively, compounds 1.2 can be prepared from anilines 1.1b (commercially available or synthesized by those skilled in the art) by diazotization using dibenzyldisulfide and amyl nitrite in $CH_3CN$ at elevated temperature. Reduction of esters 1.2 (R=Me, Et) with reducing agents (LAH or $NaBH_4$) affords primary alcohols 1.3. Alcohol 1.3 can be converted to 1.4 by reaction with acetic anhydride in a presence of a base such as DIEA. Finally, a smooth oxidation of thio-ethers 1.4 by combination of NCS and AcOH affords the corresponding sulfonyl chlorides 1.5 according to general reaction conditions reported in *Synthesis,* 2006, 24, 4131-4134 and *Bioorg. Med. Chem.,* 2017, 25, 3447-3460.

Scheme 2

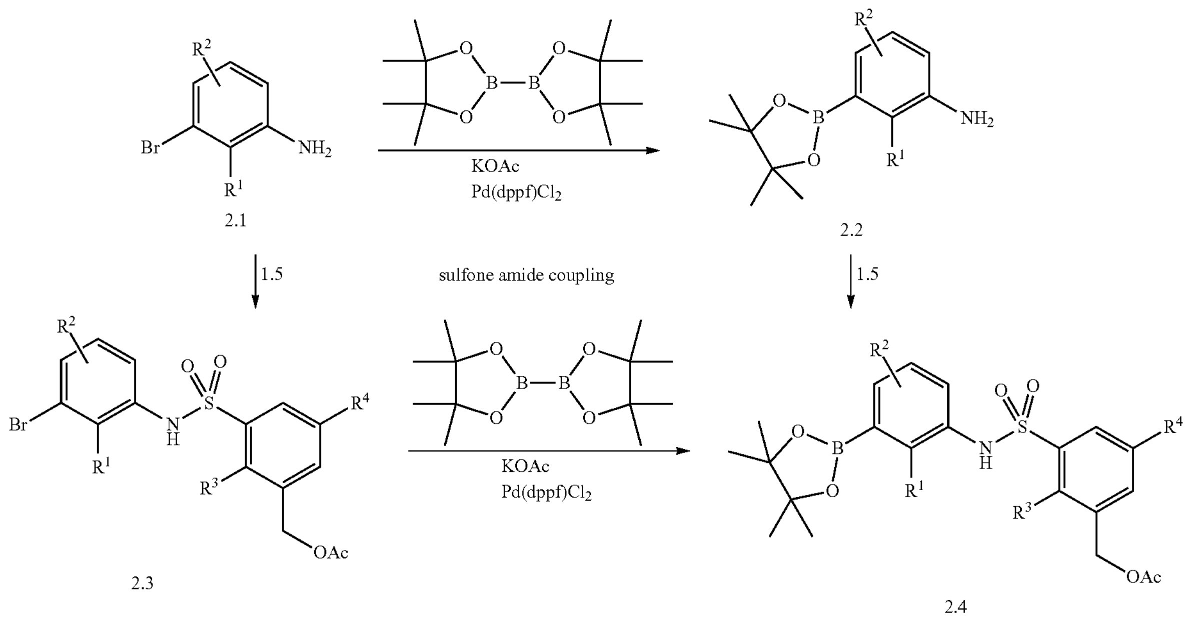

Scheme 2 illustrates an exemplary preparation of boronates 2.4. Compounds 2.1 (commercially available, synthesized as described in WO2013134298 or synthesized by those skilled in the art) react with bis(pinacolato)diboron by borylation reaction known to those skilled in the art (palladium-mediated reaction conducted using palladium catalysts such as Pd(dppf)$Cl_2$, a suitable base such as KOAc in a suitable solvent such as 1,4-dioxane at elevated temperature) to obtain compounds 2.2 which are reacted with sulfonyl chlorides 1.5 (see scheme 1) to give compounds 2.4. Alternatively, compounds 2.1 react with sulfonyl chlorides 1.5 to afford the sulfonamides 2.3 which are converted to the boronates 2.4 under the borylation reaction conditions known to those skilled in the art.

Scheme 3

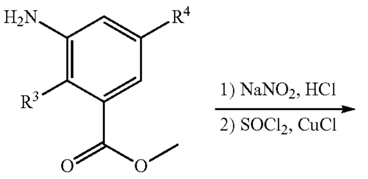

3.1

-continued

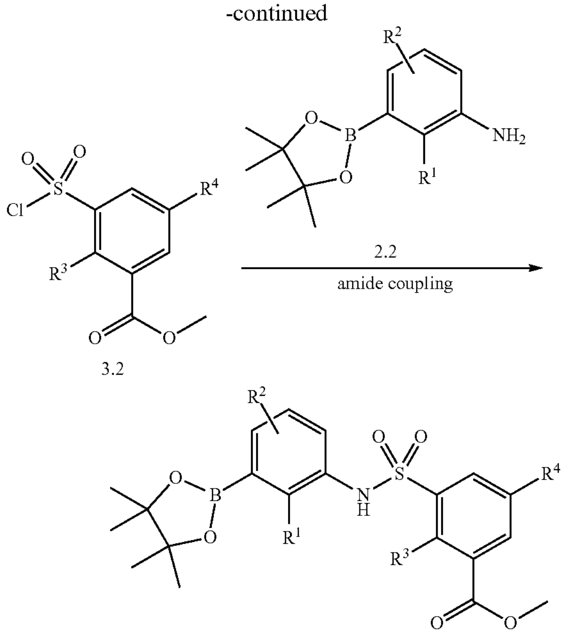

3.3

Scheme 3 illustrates an exemplary preparation of boronates 3.3. Compounds 3.2 can be prepared from anilines 3.1 (commercially available or synthesized by those skilled in the art) by diazotization, followed by Cu-mediated chlorination of the resulting intermediate (according to general reaction conditions reported in *Org. Proc. Res. Dev.*, 2009, 5, 875-879). Sulfonyl chlorides 3.2 react with amines 2.2 under sulfone amide coupling to obtain sulfonamides 3.3.

Scheme 4

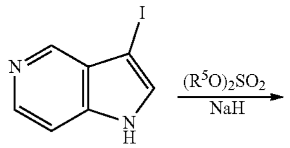

4.1

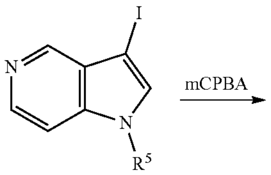

4.2

-continued

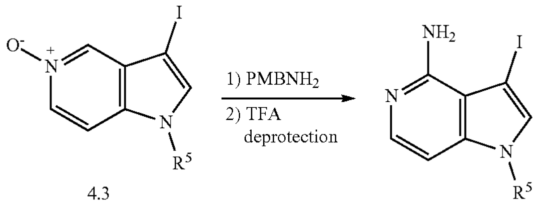

4.3

4.4

Scheme 4 illustrates an exemplary preparation of intermediates 4.4. N-alkylation of the 3-iodo-1H-pyrrolo[3,2-c] pyridine 4.1 with alkylating reagent $(R^5O)_2SO_2$ in the presence of a base such as NaH affords 4.2. Compounds 4.2 can be activated by oxidation known in the art such as mCPBA in DCM to afford N-oxides 4.3. Pyrrolopyridine N-oxides 4.3 convert to aminopyrrolopyridines 4.4 using a mixture of $PMBNH_2$ and p-toluenesulfonyl chloride followed by in situ deprotection with TFA.

Scheme 5

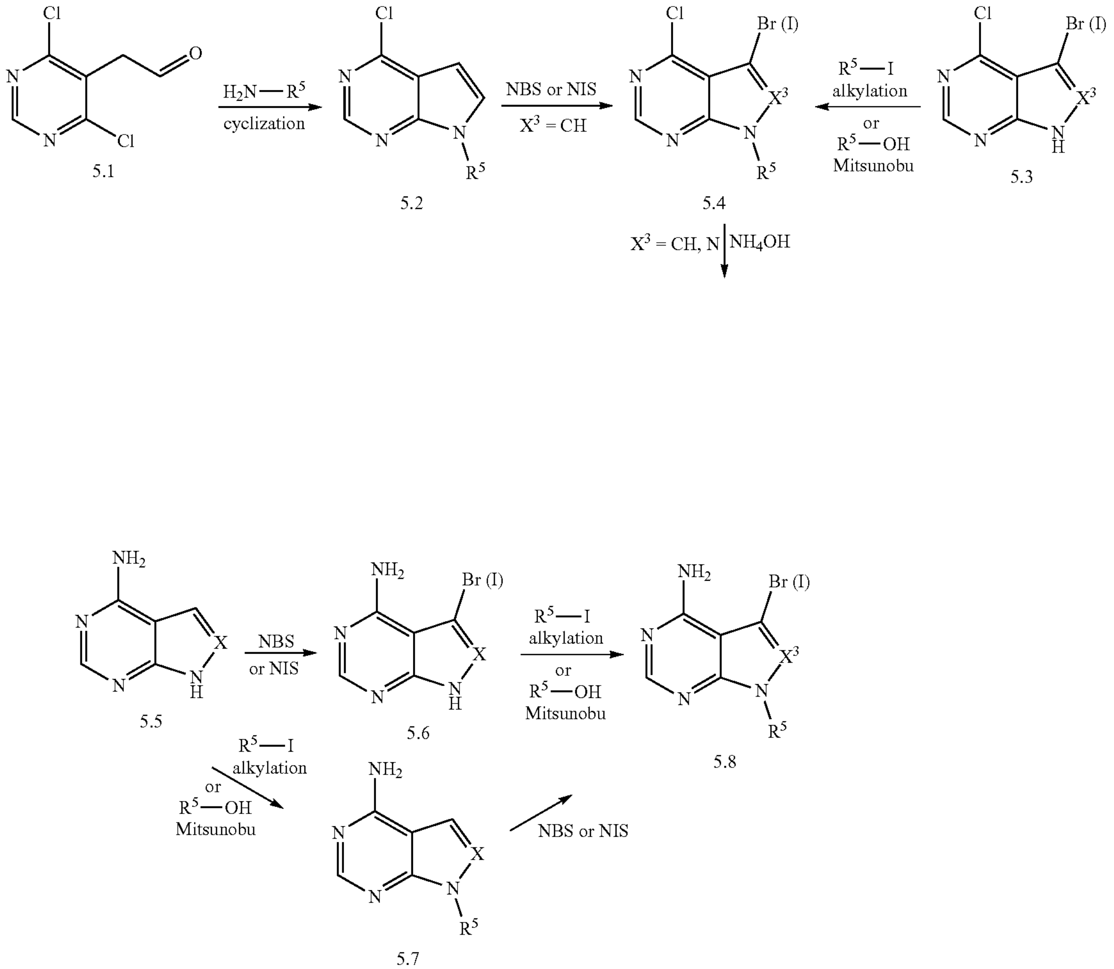

5.1 5.2 5.4 5.3

5.5 5.6 5.8

5.7

Scheme 5 illustrates an exemplary preparation of intermediates 5.8. Cyclization of 2-(4,6-dichloropyrimidin-5-yl) acetaldehyde 5.1 with various amines ($R^5$—$NH_2$) in a presence of base such as TEA in a protic solvent such as EtOH at elevated temperature affords compounds 5.2. Bromination (or Iodination) of 5.2 with NBS (or NIS) affords compounds 5.4 (X=CH). Compounds 5.5 react with NBS (or NIS) to afford 5.6. Alkylation of compounds 5.3, 5.5 and 5.6 with alkylating reagents ($R^5$—I) affords 5.7 and 5.8 respectively. Alternatively, compounds 5.3, 5.5 and 5.6 react with alcohols ($R^5$—OH) under standard Mitsunobu conditions (conducted for example in the presence of $Ph_3P$ and DIAD) produce to 5.4, 5.7 and 5.8 respectively. In another embodiment, intermediates 5.8 can be also prepared from 5.4 by substitution reaction with ammonium hydroxide and from 5.7 by bromination (or iodination) with NBS (or NIS).

Scheme 6

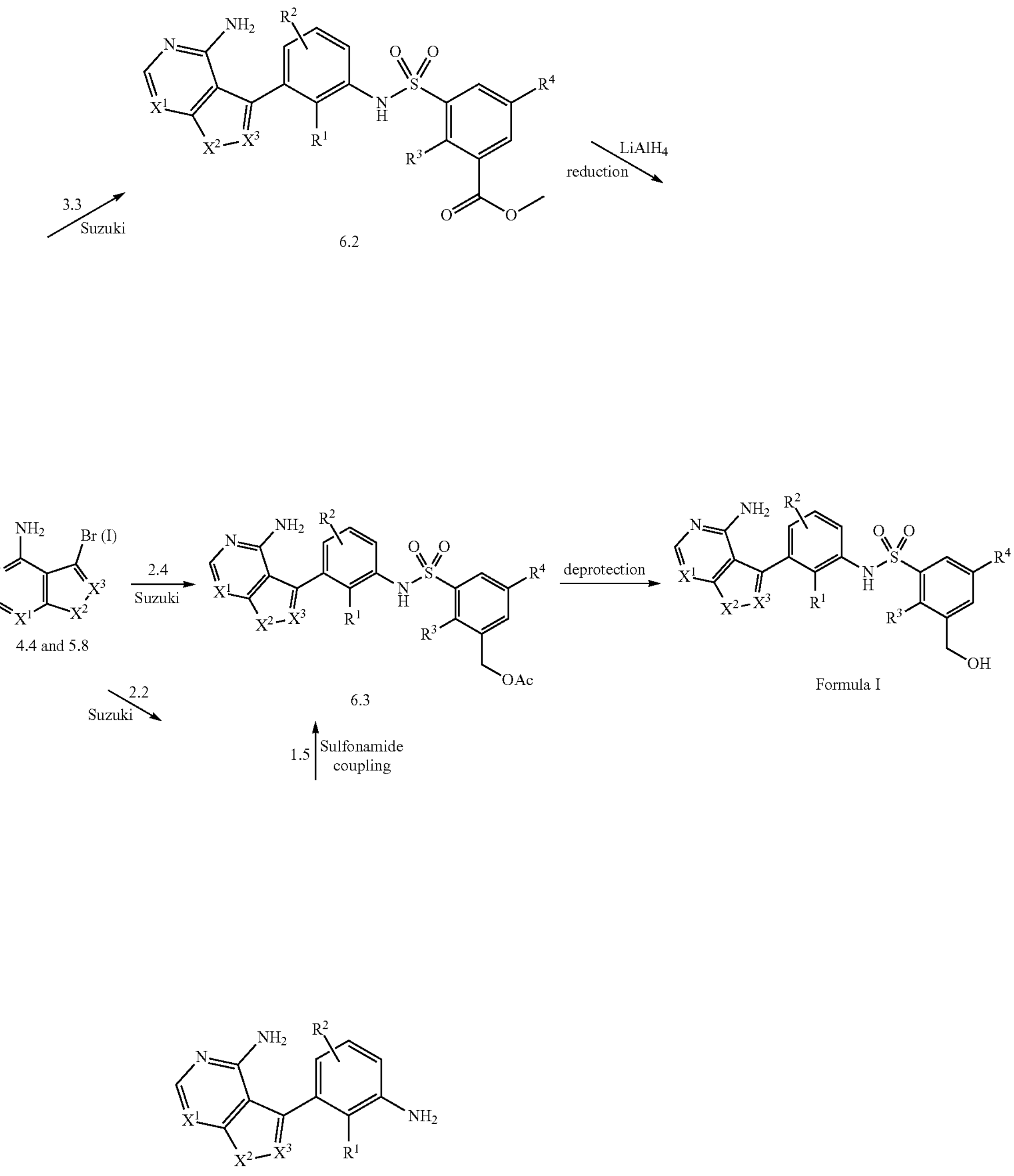

6.2

4.4 and 5.8

6.3

Formula I 6.1

Scheme 6 illustrates an exemplary preparation of Formula I. Bromides (or iodides) 4.4 and 5.8 react with boronates 2.2 in a presence of a palladium catalyst (Suzuki conditions) to afford anilines 6.1. Sulfonamide coupling reaction of anilines 6.1 with sulfonyl chlorides 1.5 afford sulfonamides 6.3. Alternatively, 6.3 can be prepared from bromides (or iodides) 4.4 and 5.8 with boronates 2.4 under Suzuki conditions. Deprotection of sulfonamides 6.3 with $K_2CO_3$ in a protic solvent such as MeOH at rt affords Formula I. In another embodiment, bromides (or iodides) 4.4 and 5.8 react with boronates 3.3 in a presence of a palladium catalyst (Suzuki conditions) to afford 6.2. Reduction of 6.2 under $LiAlH_4$ to afford primary alcohols, Formula I.

Preparation of Intermediates and Final Compounds.

Using the synthetic procedures and methods described herein and methods known to those skilled in the art, the following compounds were made:

General Method A: Borylation

Example A1: 2-fluoro-3-(4,4,5,5-tetramethyl-1,3,2-dioxaborolan-2-yl)aniline

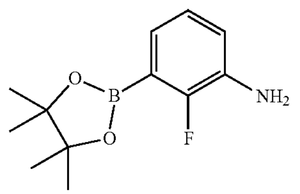 [SMILES: CC1(C)OB(c2cccc(N)c2F)OC1(C)C]

A mixture of KOAc (4.6 g, 47.4 mmol), 3-bromo-2-fluoroaniline (3.0 g, 15.8 mmol), and 4,4,4',4',5,5,5',5'-octamethyl-2,2'-bi(1,3,2-dioxaborolane) (4.8 g, 18.9 mmol) in 1,4-dioxane (30 mL) was degassed with Ar for 10 min. $PdCl_2$ (dppf) DCM adduct (1.3 g, 1.6 mmol) was added and the reaction mixture was heated at 110° C. for 6 h. The reaction was cooled to rt and filtered through a pad of celite. The filtrate was removed under reduced pressure and the residue was purified by silica gel column chromatography (0 to 50% EtOAc/hex) to obtain 2-fluoro-3-(4,4,5,5-tetramethyl-1,3,2-dioxaborolan-2-yl)aniline (2.7 g, 72%) as a tan solid. $^1H$ NMR (500 MHz, DMSO-$d_6$): δ 6.86 (m, 2H), 6.76 (d, J=6.8 Hz, 1H), 5.02 (s, 2H), 1.28 (s, 12H); MS (ESI) m/z: 238.2 (M+$H^+$).

Using the General Method A above, the following Intermediates of Table A were prepared.

TABLE A

| Ex No | Product | Yield (%) | $^1H$ NMR (400 or 500 MHz, DMSO-$d_6$): δ | MS (m/z: M + $H^+$) |
|---|---|---|---|---|
| A2 | 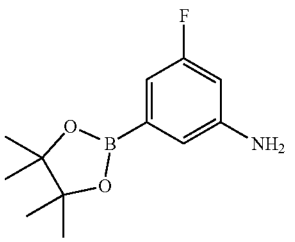 [SMILES: CC1(C)OB(c2cc(N)cc(F)c2)OC1(C)C] | 88 | 6.77 (d, J = 2.0 Hz, 1H), 6.42 (m, 2H), 5.42 (s, 2H), 1.27 (s, 12H). | 238.2 |

TABLE A-continued

| Ex No | Product | Yield (%) | $^1$H NMR (400 or 500 MHz, DMSO-$d_6$): δ | MS (m/z: M + $H^+$) |
|---|---|---|---|---|
| A3 | 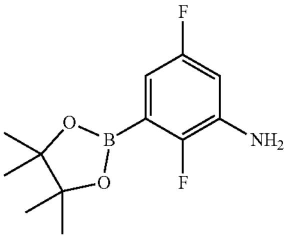 [SMILES: CC1(C)OB(c2cc(F)cc(N)c2F)OC1(C)C] | crude | No Data | 256.2 |
| A4 | 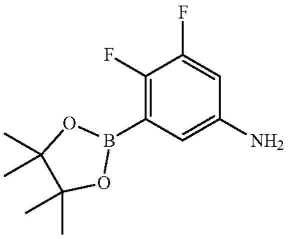 [SMILES: CC1(C)OB(c2cc(N)cc(F)c2F)OC1(C)C] | 36 | 6.59 (m, 2H), 5.20 (br s, 2H), 1.28 (s, 12H). | 256.1 |
| A5 | 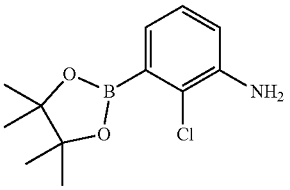 | 43 | 6.99 (t, J = 7.6 Hz, 1H), 6.86 (d, J = 6.4 Hz, 1H), 6.77 (d, J = 6.8 Hz, 1H), 5.25 (br s, 2H), 1.28 (s, 12H). | 254.1 |

General Method B: Alkylation

Example B1: 4-chloro-5-iodo-7-isopropyl-7H-pyrrolo[2,3-d]pyrimidine

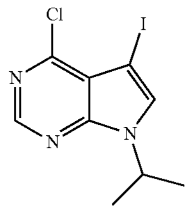

A solution of 4-chloro-5-iodo-7H-pyrrolo[2,3-d]pyrimidine (2.0 g, 7.2 mmol) in DMF (18 mL) was treated with $Cs_2CO_3$ (4.7 g, 14 mmol). 2-Iodopropane (1.2 g, 7.2 mmol) was added and the reaction mixture was stirred at rt for 12 h. The reaction was poured into water (100 mL) and the solids were collected via vacuum filtration to obtain 4-chloro-5-iodo-7-isopropyl-7H-pyrrolo[2,3-d]pyrimidine (1.8 g, 78%) as a yellow fluffy solid. $^1$H NMR (500 MHz, DMSO-$d_6$): δ 8.63 (s, 1H), 8.18 (d, J=1.4 Hz, 1H), 5.04 (m, 1H), 1.47 (d, J=6.8 Hz, 6H); MS (ESI) m/z: 322.0 (M+$H^+$).

Using the General Method B above, the following Intermediates of Table B were prepared.

TABLE B

| Ex No | SM | Product | Yield (%) | $^1H$ NMR (400 or 500 MHz, DMSO-$d_6$): δ | MS (m/z: M + $H^+$) |
|---|---|---|---|---|---|
| B2 | 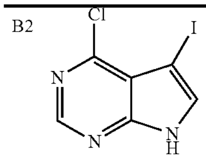 | 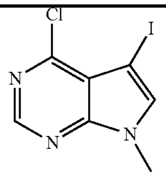 | 68 | 8.64 (s, 1H), 7.96 (s, 1H), 3.82 (s, 3H). | 294.01 |
| B3 | 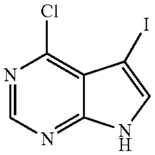 | 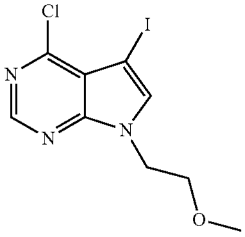 | 74 | 8.64 (d, J = 1.6 Hz, 1H), 7.99 (t, J = 1.5 Hz, 1H), 4.43 (t, J = 5.3 Hz, 2H), 3.71 (t, J = 5.3 Hz, 2H), 3.22 (s, 3H). | 338.0 |
| B4 | 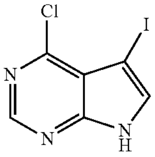 | 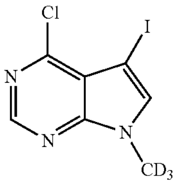 [SMILES: [2H]C([2H])([2H])n1cc(I)c2c(Cl)ncnc21] | crude | 8.65 (s, 1H), 7.98 (s, 1H). | No Data |
| B5 | 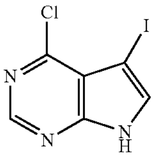 | 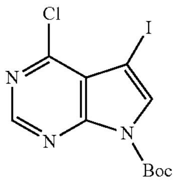 [SMILES: CC(C)(C)OC(=O)n1cc(I)c2c(Cl)ncnc21] | 74 | 8.81 (s, 1H), 8.17 (s, 1H), 1.61 (s, 9H). | 379.8 |

Preparation of B6: (E)-N'-(5-iodo-7-(1-methyl-1H-pyrazol-4-yl)-7H-pyrrolo[2,3-d]pyrimidin-4-yl)-N,N-dimethylformimidamide

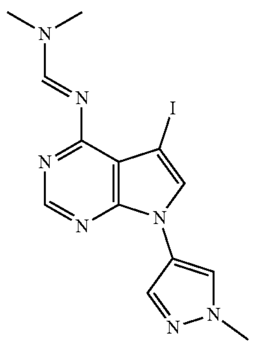

A solution of 5-iodo-7H-pyrrolo[2,3-d]pyrimidin-4-amine (5.0 g, 19 mmol.) in DMF (50 mL) was treated with N,N-dimethylformamide dimethyl acetal (3.43 g, 28 mmol). The reaction mixture was stirred at rt for 16 h. The reaction mixture was concentrated under reduced pressure and the residue was diluted with DCM (150 mL), washed with brine (2×) solution. The organic layer was dried over anhydrous $Na_2SO_4$, filtered, and concentrated. The crude material was triturated with diethyl ether (100 mL) and the solids were filtered to afford desired (E)-N'-(5-iodo-7H-pyrrolo[2,3-d]pyrimidin-4-yl)-N,N-dimethylformimidamide (5.0 g, 85%). $^1H$ NMR (500 MHz, DMSO-$d_6$): δ 11.9 (s, 1H), 8.80 (s, 1H), 8.27 (s, 1H), 7.41 (d, J=2.0, 1H), 3.21 (s, 3H), 3.17 (s, 3H); MS (ESI) m/z: 315.8 (M+$H^+$).

A solution of (E)-N'-(5-iodo-7H-pyrrolo[2,3-d]pyrimidin-4-yl)-N,N-dimethylformimidamide (2.0 g, 6.3 mmol) and 1-methyl-4-(4,4,5,5-tetramethyl-1,3,2-dioxaborolan-2-yl)-1H-pyrazole (1.6 g, 7.6 mol) in DMF (30 mL) under oxygen atmosphere was treated with $NaHCO_3$ (1.3 g, 12.6 mmol), 2,2-bipyridyl (1.1 g, 6.9 mmol) and $Cu(OAc)_2$ (1.3 g, 6.9 mol) at rt. The reaction mixture was stirred at rt for 4 days and concentrated under reduced pressure. The crude material was triturated with diethyl ether (60 mL) and the solids were filtered to afford desired (E)-N'-(5-iodo-7-(1-methyl-1H-pyrazol-4-yl)-7H-pyrrolo[2,3-d]pyrimidin-4-yl)-N,N-dimethylformimidamide (3.0 g, crude) which was used for the next reaction without further purification. MS (ESI) m/z: 395.8 (M+$H^+$).

Example B7: (E)-N'-(5-iodo-7-(1H-pyrazol-4-yl)-7H-pyrrolo[2,3-d]pyrimidin-4-yl)-N,N-dimethyl-formimidamide

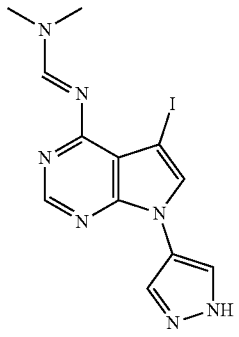 [SMILES: CN(C)/C=N/c1ncnc2c1c(I)cn2-c1cn[nH]c1]

(E)-N'-(5-iodo-7-(1H-pyrazol-4-yl)-7H-pyrrolo[2,3-d]pyrimidin-4-yl)-N,N-dimethylformimidamide was prepared as Example B6 from (E)-N'-(5-iodo-7H-pyrrolo[2,3-d]pyrimidin-4-yl)-N,N-dimethylformimidamide (0.69 g, 2.2 mmol) and 4-(4,4,5,5-tetramethyl-1,3,2-dioxaborolan-2-yl)-1H-pyrazolepyrazole (0.5 g, 2.6 mol). MS (ESI) m/z: 381.8 (M+H$^+$).

General Method C: Cyclization

Example C1: 4-chloro-7-cyclopropyl-7H-pyrrolo[2,3-d]pyrimidine

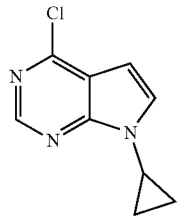 [SMILES: Clc1ncnc2c1ccn2C1CC1]

A solution of 2-(4,6-dichloropyrimidin-5-yl)acetaldehyde (2.0 g, 10.5 mmol) in EtOH (18 mL) was treated with $Et_3N$ (2.9 mL, 21 mmol). The reaction mixture was stirred at rt for 10 min, and then cyclopropanamine (0.6 mL, 9.4 mmol) was added. The reaction mixture was stirred at 140° C. overnight. The reaction mixture was cooled to rt and then concentrated under reduced pressure. The crude was purified by silica gel column chromatography (0 to 100% EtOAc/hex) to obtain 4-chloro-7-cyclopropyl-7H-pyrrolo[2,3-d]pyrimidine (1.6 g, 79%) as a light yellow solid. $^1$H NMR (500 MHz, DMSO-$d_6$): δ 8.59 (s, 1H), 7.65 (d, J=3.7 Hz, 1H), 6.54 (d, J=3.5 Hz, 1H), 3.59 (m, 1H), 1.01-1.03 (m, 4H); MS (ESI) m/z: 194.0 (M+H$^+$).

Using the General Method C above, the following Intermediates of Table C were prepared.

TABLE C

| Ex No | SM | Product | Yield (%) | $^1$H NMR (400 or 500 MHz, DMSO-$d_6$): δ | MS (m/z: M + H$^+$) |
|---|---|---|---|---|---|
| C2 | 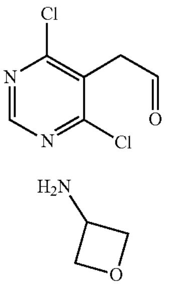 | 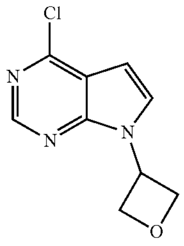 [SMILES: Clc1ncnc2c1ccn2C1COC1] | 73 | 8.67 (s, 1H), 8.18 (d, J = 3.7 Hz, 1H), 6.78 (d, J = 3.7 Hz, 1H), 5.98 (m, 1H), 5.02 (dd, J = 7.2, 1.6 Hz, 4H). | 210.0 |
| C3 | 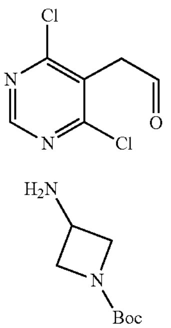 | 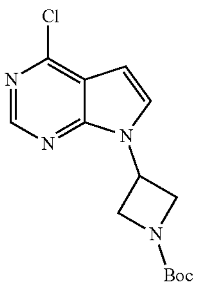 [SMILES: CC(C)(C)OC(=O)N1CC(n2ccc3c(Cl)ncnc32)C1] | 38 | No Data | 309.2 |

TABLE C-continued

| Ex No | SM | Product | Yield (%) | $^{1}$H NMR (400 or 500 MHz, DMSO-$d_6$): δ | MS (m/z: M + $H^+$) |
|---|---|---|---|---|---|
| C4 | 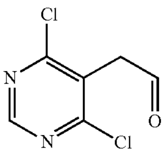 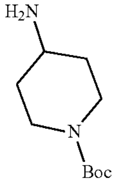 | 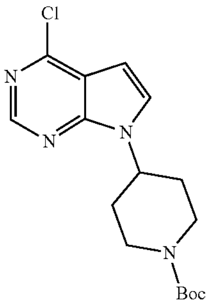 | 74 | No Data | 337.2 |
| C5 | 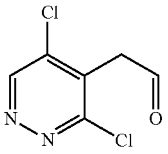 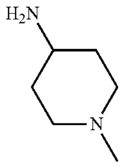 | 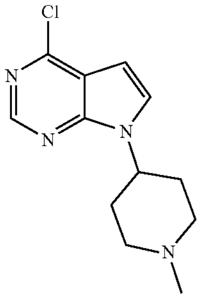 [SMILES: CN1CCC(n2ccc3c(Cl)ncnc32)CC1] | 91 | 8.66 (s, 1H), 7.84 (d, J = 3.7 Hz, 1H), 6.72 (d, J = 3.7 Hz, 1H), 4.88 (m, 1H), 3.34 (m, 2H), 2.94 (br m, 2H), 2.64 (s, 3H), 2.40 (m, 2H), 2.10 (m, 2H). | 251.0 |

General Method D: Bromination or Iodination

Example D1: 5-bromo-4-chloro-7-cyclopropyl-7H-pyrrolo[2,3-d]pyrimidine

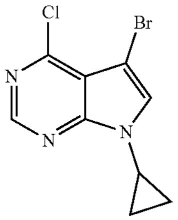 [SMILES: Clc1ncnc2c1c(Br)cn2C1CC1]

A solution of 4-chloro-7-cyclopropyl-7H-pyrrolo[2,3-d]pyrimidine ($C_1$, 0.67 g, 3.5 mmol) in DCM (15 mL) was treated with NBS (0.74 g, 4.2 mmol) and the reaction mixture was stirred for 1 h at rt. The reaction mixture was concentrated under reduced pressure and the residue was suspended in water (5 mL). The solids were filtered and washed with water (2 mL), dried under vacuum to afford 5-bromo-4-chloro-7-cyclopropyl-7H-pyrrolo[2,3-d]pyrimidine (0.6 g, 64%) as white solid. $^{1}$H NMR (500 MHz, DMSO-$d_6$): δ 8.69 (s, 1H), 8.00 (d, J=2.1 Hz, 1H), 3.66 (m, 1H), 1.10 (m, 4H); MS (ESI) m/z: 272.0 (M+$H^+$) and 274.

Using the General Method D above, the following Intermediates of Table D were prepared.

TABLE D

| Ex No | SM | Product | Yield (%) | $^{1}$H NMR (400 or 500 MHz, DMSO-$d_6$): δ | MS (m/z: M + $H^+$) |
|---|---|---|---|---|---|
| D2 | C2 | 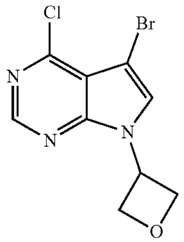 [SMILES: Clc1ncnc2c1c(Br)cn2C1COC1] | 86 | 8.70 (s, 1H), 8.46 (s, 1H), 5.95 (m, 1H), 4.90-5.11 (m, 4H). | 288.0 290.0 |

TABLE D-continued

| Ex No | SM | Product | Yield (%) | $^1H$ NMR (400 or 500 MHz, DMSO-$d_6$): δ | MS (m/z: M + $H^+$) |
|---|---|---|---|---|---|
| D3 | 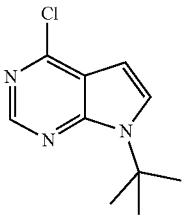 | 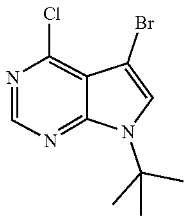 | 65 | No Data | 288.0<br>290.0 |
| D4 | C3 | 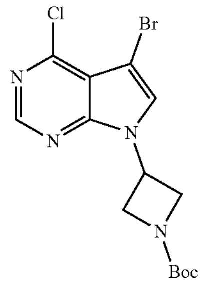 [SMILES: CC(C)(C)OC(=O)N1CC(n2cc(Br)c3c(Cl)ncnc32)C1] | 87 | 8.68 (s, 1H), 8.37 (s, 1H), 5.58 (m, 1H), 4.33 (m, 4H), 1.43 (s, 9H). | 387.0<br>389.0 |
| D5 | C4 | 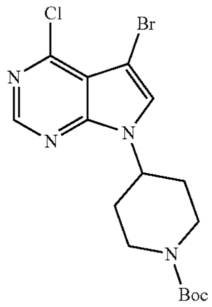 [SMILES: CC(C)(C)OC(=O)N1CCC(n2cc(Br)c3c(Cl)ncnc32)CC1] | 93 | 8.67 (s, 1H), 8.23 (s, 1H), 4.90 (m, 1H), 4.12 (br m, 2H), 2.95 (br m, 2H), 1.85-2.10 (m, 4H), 1.44 (s, 9H). | 415.0<br>417.0 |
| D6 | C5 | 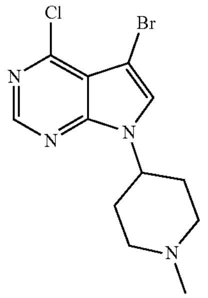 [SMILES: CN1CCC(n2cc(Br)c3c(Cl)ncnc32)CC1] | 76 | No Data | 329.0<br>331.0 |

General Method E: Substitution

Example E1: 5-iodo-7-isopropyl-7H-pyrrolo[2,3-d]pyrimidin-4-amine

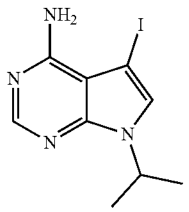

A suspension of 4-chloro-5-iodo-7-isopropyl-7H-pyrrolo[2,3-d]pyrimidine (B1, 1.78 g, mmol) in 1,4-dioxane (5.5 mL) was treated with $NH_4OH$ (30% in water, 1.7 mL, 13 mmol) and the reaction was heated to 95° C. overnight. The mixture was cooled to rt and diluted with cold water. The mixture was stirred at 0° C. for 30 min and then the solids were collected via vacuum filtration to obtain the desired product 5-iodo-7-isopropyl-7H-pyrrolo[2,3-d]pyrimidin-4-amine (0.80 g, 48%) as a white solid. $^1H$ NMR (500 MHz, DMSO-$d_6$): δ 8.09 (s, 1H), 7.59 (s, 1H), 6.59 (s, 2H), 4.89 (m, 1H), 1.40 (d, J=6.8 Hz, 6H); MS (ESI) m/z: 303.0 (M+$H^+$).

Using the General Method E above, the following Intermediates of Table E were prepared.
TABLE E
| Ex No | SM | Product | Yield (%) | $^1$H NMR (400 or 500 MHz, DMSO-$d_6$): δ | MS (m/z: M + $H^+$) |
|---|---|---|---|---|---|
| E2 | B2 | 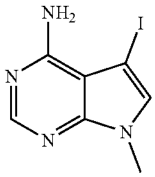 | 56 | 8.09 (s, 1H), 7.41 (s, 1H), 6.57 (br s, 2H), 3.66 (s, 3H). | 274.78 |
| E3 | B3 | 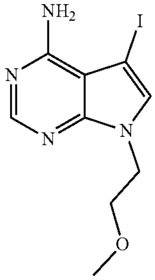 | 71 | 8.10 (s, 1H), 7.44 (s, 1H), 6.61 (s, 2H), 4.26 (t, J = 5.4 Hz, 2H), 3.64 (t, J = 5.4 Hz, 2H), 3.22 (s, 3H). | 319.0 |
| E4 | D1 | 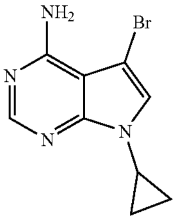 [SMILES: Nc1ncnc2c1c(Br)cn2C1CC1] | 97 | 8.17 (s, 1H), 7.43 (s, 1H), 6.78 (s, 2H), 3.56 (m, 1H), 1.05 (d, J = 6.7 Hz, 4H). | 253.0 255.0 |
| E5 | D2 | 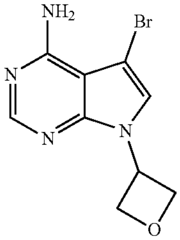 [SMILES: Nc1ncnc2c1c(Br)cn2C1COC1] | 62 | No Data | 269.0 271.0 |
| E6 | D3 | 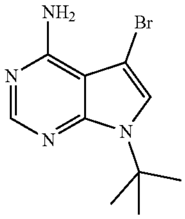 | 71 | No Data | 269.0 271.0 |
| E7 | D4 | 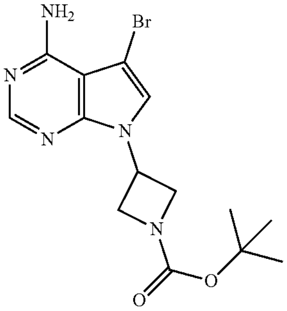 [SMILES: CC(C)(C)OC(=O)N1CC(n2cc(Br)c3c(N)ncnc32)C1] | 80 | 8.10 (s, 1H), 7.77 (s, 1H), 6.70 (br s, 2H), 5.43 (m, 1H), 4.16-4.38 (m, 4H), 1.42 (s, 9H). | 368.2 370.2 |

TABLE E-continued
| Ex No | SM | Product | Yield (%) | $^1$H NMR (400 or 500 MHz, DMSO-$d_6$): δ | MS (m/z: M + H$^+$) |
|---|---|---|---|---|---|
| E8 | D5 | 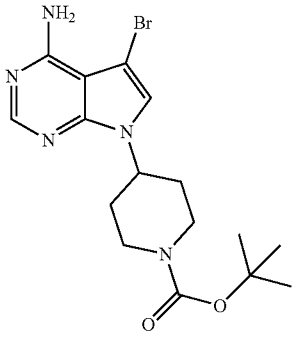 [SMILES: CC(C)(C)OC(=O)N1CCC(n2cc(Br)c3c(N)ncnc32)CC1] | 87 | 8.10 (s, 1H), 7.60 (s, 1H), 6.72 (br s, 2H), 4.68 (m, 1H), 4.10 (br m, 2H), 2.91 (br m, 2H), 1.70-1.99 (m, 4H), 1.43 (s, 9H). | 396.2 398.2 |
| E9 | D6 | 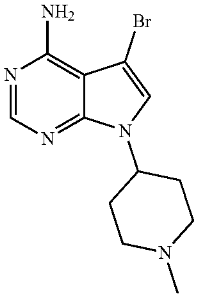 [SMILES: CN1CCC(n2cc(Br)c3c(N)ncnc32)CC1] | 42 | 8.02 (s, 1H), 7.49 (s, 1H), 6.63 (s, 2H), 4.40 (m, 1H), 2.81 (m, 2H), 2.14 (s, 3H), 1.89-2.01 (m, 4H), 1.65-1.82 (m, 2H). | 310.0 312.0 |
| E10 | B4 | 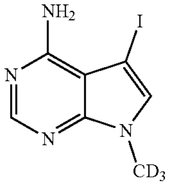 | 90 | 8.10 (s, 1H), 7.40 (s, 1H), 6.62 (br s, 2H). | 278.0 |
| E11 | B5 | 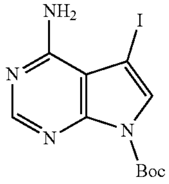 [SMILES: CC(C)(C)OC(=O)n1cc(I)c2c(N)ncnc21] | 58 | 8.23 (s, 1H), 7.69 (s, 1H), 6.86 (br s, 2H), 1.60 (s, 9H). | 360.8 |
| E13 | B6 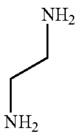 | 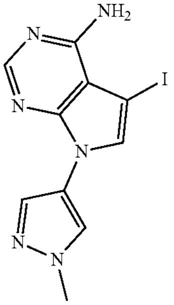 [SMILES: Cn1cc(-n2cc(I)c3c(N)ncnc32)cn1] | 23 | 8.32 (s, 1H), 8.17 (s, 1H), 7.95 (s, 1H), 7.81 (s, 1H), 6.74 (br s, 2H), 3.89 (s, 3H). | 340.8 |

TABLE E-continued

| Ex No | SM | Product | Yield (%) | $^1H$ NMR (400 or 500 MHz, DMSO-$d_6$): δ | MS (m/z: M + $H^+$) |
|---|---|---|---|---|---|
| E14 | B7 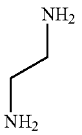 | 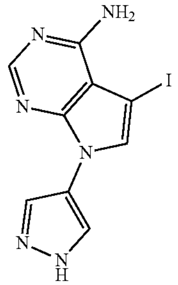 [SMILES: Nc1ncnc2c1c(I)cn2-c1cn[nH]c1] | 10 | 11.41 (br s, 1H), 8.00 (s, 1H), 7.04 (dd, J = 3.2, 2.4 Hz, 1H), 6.84 (br m, 3H), 7.04 (dd, J = 3.6, 2.0 Hz, 1H). | 326.8 |

Preparation of Example E12: 3-iodo-1-methyl-1H-pyrrolo[3,2-c]pyridin-4-amine

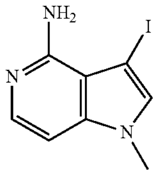

A stirred suspension of 3-iodo-1-methyl-1H-pyrrolo[3,2-c]pyridine (0.90 g, 3.5 mmol) in DCM (20 mL) was treated with 3-chloroperoxybenzoic acid (0.90 g, 5.2 mmol) at rt. The reaction mixture was stirred at rt for 2 h. The reaction mixture was reaction mixture was quenched with sat'd $NaHCO_3$ solution and then extracted with DCM (2×). The combined organic layers were dried over anhydrous $Na_2SO_4$, filtered, and concentrated under reduced pressure to yield the crude 3-iodo-1-methyl-1H-pyrrolo[3,2-c]pyridine 5-oxide (0.6 g, 65%) as an off white solid. $^1H$ NMR (400 MHz, DMSO-$d_6$): δ 8.12 (s, 1H), 8.00 (d, J=7.2 Hz, 1H), 7.34 (s, 1H), 7.59 (d, J=7.2 Hz, 1H), 3.82 (s, 3H); MS (ESI) m/z: 275.0 (M+$H^+$).

A solution of 3-iodo-1-methyl-1H-pyrrolo[3,2-c]pyridine 5-oxide (0.6 g, 2.1 mmol) in chloroform (20 mL) was treated with (4-methoxyphenyl)methanamine (1.3 g, 9.8 mmol) and stirred for about 30 min at rt. The mixture was cooled to 0° C. followed by the portion wise addition of p-toluene sulphonyl chloride (0.92 g, 4.8 mmol) and the reaction mixture was stirred at rt for 2.5 h. The mixture was diluted with DCM (50 mL) and washed with sat'd $NaHCO_3$ solution. The organic layer was separated, dried over anhydrous $Na_2SO_4$, filtered, and concentrated under reduced pressure. The crude was purified by silica gel column chromatography (70% EtOAc/hex) to yield the 3-iodo-N-(4-methoxybenzyl)-1-methyl-1H-pyrrolo[3,2-c]pyridin-4-amine (0.2 g, 23%) as a pale yellow solid. $^1H$ NMR (400 MHz, DMSO-$d_6$): δ 7.68 (d, J=6.4 Hz, 1H), 7.36 (s, 1H), 7.31 (d, J=7.6 Hz, 2H), 6.89 (d, J=7.6 Hz, 2H), 6.81 (d, J=6.0 Hz, 1H), 6.14 (br m, 1H), 4.64 (d, J=5.2 Hz, 2H), 3.73 (s, 3H), 3.69 (s, 3H); MS (ESI) m/z: 394.2 (M+$H^+$).

A suspension of 3-iodo-N-(4-methoxybenzyl)-1-methyl-1H-pyrrolo[3,2-c]pyridin-4-amine (0.2 g, 0.508 mmol) in DCM (10 mL) was stirred under an ice-water bath. TFA (1 mL) was added drop wise and then the reaction mixture was stirred at rt for 4 h. The reaction mixture was concentrated under reduced pressure and the residue was treated with sat'd $NaHCO_3$ solution. The mixture was stirred for 10 min and the aqueous layer was further extracted with 10% MeOH/DCM (2×). The combined organic extracts were dried over anhydrous $Na_2SO_4$, filtered, and concentrated under reduced pressure. The crude was purified by silica gel column chromatography (3 to 5% MeOH/DCM) to afford 3-iodo-1-methyl-1H-pyrrolo[3,2-c]pyridin-4-amine (0.05 g, 36%) as an off white solid. $^1H$ NMR (400 MHz, DMSO-$d_6$): δ 7.63, d, J=6.4 Hz, 1H), 7.48 (s, 1H), 6.94 (d, J=6.4 Hz, 1H), 6.35 (br s, 2H), 3.72 (s, 3H); MS (ESI) m/z: 273.9 (M+$H^+$).

General Method F: Preparation of Thio-Ethers from Amines

Example F1: ethyl 3-(benzylthio)-2,5-dichlorobenzoate

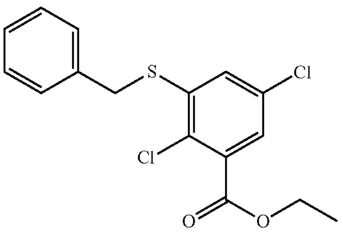 [SMILES: CCOC(=O)c1cc(Cl)cc(SCc2ccccc2)c1Cl]

A solution of ethyl 3-amino-2,5-dichlorobenzoate (12.0 g, 51.0 mmol) in $CH_3CN$ (250 mL) was treated with amyl nitrite (9.64 mL, 81.0 mmol). Dibenzyl disulfide (12.6 g, 51.0 mmol) was added at rt and the reaction mixture was heated at 70° C. for 3 h. The reaction mixture was quenched with ice water (100 mL) and extracted with EtOAc (3×). The combined organics were dried over anhydrous $Na_2SO_4$, filtered, and concentrated under reduced pressure. The crude was purified by silica gel column chromatography (10 to 20% EtOAc/hex) to afford ethyl 3-(benzylthio)-2,5-dichlorobenzoate (10.0 g, 58%) as an off white solid. $^1H$ NMR (500 MHz, DMSO-$d_6$): δ 7.63 (d, J=2.8 Hz, 1H), 7.56 (d, J=2.4 Hz, 1H), 7.44 (d, J=7.2 Hz, 2H), 7.35 (t, J=7.6 Hz, 2H) 7.28 (d, J=7.2 Hz, 1H), 4.42 (s, 2H), 4.33 (q, J=7.2 Hz, 2H), 1.29 (t, J=6.8 Hz, 3H).

General Method G: Preparation of Thio-Ethers from Bromine

Example F2: ethyl 3-(benzylthio)-2-chlorobenzoate

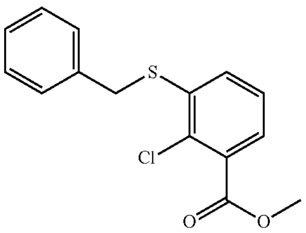 [SMILES: COC(=O)c1cccc(SCc2ccccc2)c1Cl]

A solution of methyl 3-bromo-2-chlorobenzoate (3.0 g, 12 mmol), phenylmethanethiol (1.6 g, 13 mmol) in toluene (30 mL) was treated with DIEA (4.2 mL, 24 mmol). The mixture was purged with Ar for 5 min and then XantPhos (0.67 g, 1.2 mmol) and $Pd_2(dba)_3$ (0.55 g, 0.60 mmol) were added. The mixture was purged with Ar for 5 min and heated to 90° C. overnight. The reaction was cooled to rt, and filtered through silica gel, washed with EtOAc:hex (1:1). The filtrate was concentrated under reduced pressure and the residue was purified by silica gel column chromatography (0 to 100% EtOAc:hex) to obtain methyl 3-(benzylthio)-2-chlorobenzoate (2.8 g, 80%) as an orange oil. $^1H$ NMR (500 MHz, DMSO-$d_6$): δ 7.60 (dd, J=8.0, 1.5 Hz, 1H), 7.50 (dd, J=7.6, 1.5 Hz, 1H), 7.37-7.46 (m, 2H), 7.31-7.37 (m, 2H), 7.23-7.31 (m, 2H), 4.34 (s, 2H), 3.85 (s, 3H).

Using the General Methods F and G above, the following Intermediates of Table F were prepared.

TABLE F

| Ex No | SM | Product | Yield (%) | $^1H$ NMR (400 or 500 MHz, DMSO-$d_6$): δ |
|---|---|---|---|---|
| F3 | 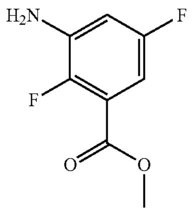 | 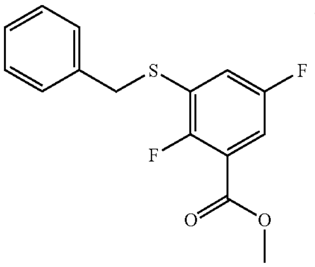 [SMILES: COC(=O)c1cc(F)cc(SCc2ccccc2)c1F] | 41 | 7.59-7.72 (m, 1H), 7.48 (m, 1H), 7.38-7.44 (m, 2H), 7.20-7.26 (m, 2H), 7.15 (m, 1H), 4.03 (s, 2H), 3.77 (s, 3H). |
| F4 | 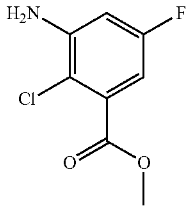 | 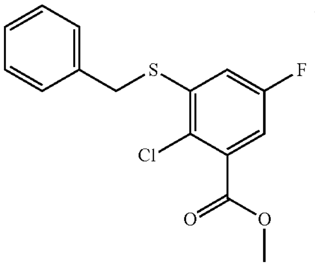 [SMILES: COC(=O)c1cc(F)cc(SCc2ccccc2)c1Cl] | 45 | 7.46-7.52 (m, 3H), 7.29-7.44 (m, 4H), 4.39 (s, 2H), 3.85 (s, 3H). |
| F5 | 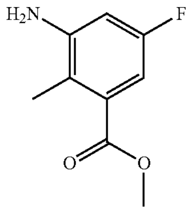 | 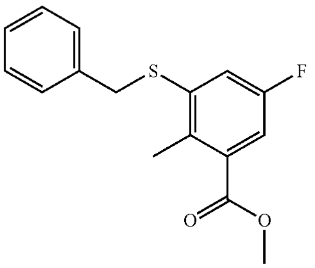 [SMILES: COC(=O)c1cc(F)cc(SCc2ccccc2)c1C] | 24 | 7.39 (m, 3H), 7.24-7.34 (m, 4H), 4.32 (s, 2H), 3.81 (s, 3H), 2.32 (s, 3H). |
| F6 | 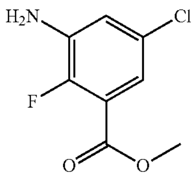 | 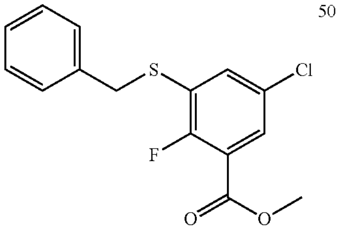 | 50 | 7.72 (m, 1H), 7.63 (m, 1H), 7.36 (d, J = 7.2 Hz, 2H), 7.33 (t, J = 6.8 Hz, 2H), 7.26 (m, 1H), 4.37 (s, 2H), 3.85 (s, 3H). |

TABLE F-continued

| Ex No | SM | Product | Yield (%) | $^1$H NMR (400 or 500 MHz, DMSO-$d_6$): δ |
|---|---|---|---|---|
| F7 | 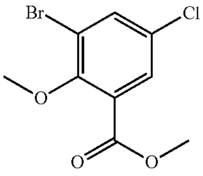 | 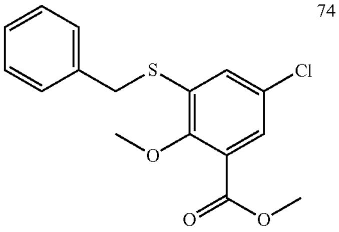 | 74 | 7.55 (d, J = 2.8 Hz, 1H), 7.47 (d, J = 2.4 Hz, 1H), 7.41 (m, 2H), 7.33 (t, J = 7.1 Hz, 2H), 7.24 (m, 1H), 4.14 (s, 2H), 3.90 (s, 3H), 3.70 (s, 3H). |
| F8 | 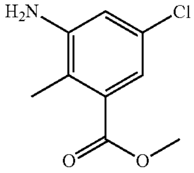 | 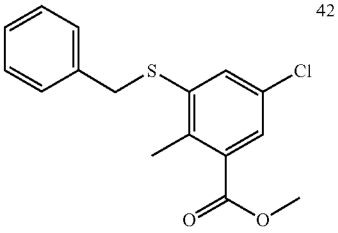 | 42 | 7.54 (m, 1H), 7.50 (m, 1H), 7.39 (m, 2H), 7.32 (t, J = 8.0 Hz, 2H), 7.26 (m, 1H), 4.32 (s, 2H), 3.82 (s, 3H), 2.35 (s, 3H). |
| F9 | 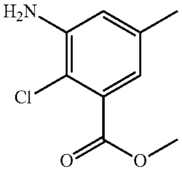 | 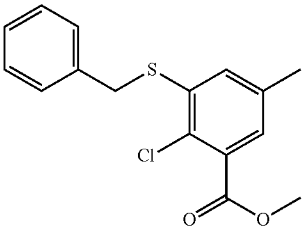 [SMILES: COC(=O)c1cc(C)cc(SCc2ccccc2)c1Cl] | 71 | 7.43 (m, 3H), 7.35 (m, 3H), 7.21 (m, 1H), 4.32 (s, 2H), 3.83 (s, 3H), 2.30 (s, 3H). |
| F10 | 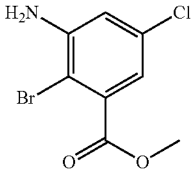 | 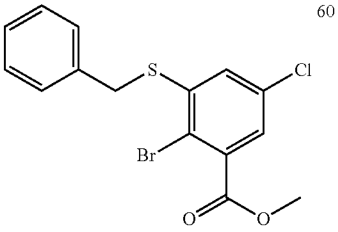 | 60 | 7.53 (d, J = 2.4 Hz, 1H), 7.51 (d, J = 2.4 Hz, 1H), 7.26-7.45 (m, 5H), 4.41 (s, 2H), 3.89 (s, 3H). |

General Method H: Reduction

Example G1: (3-(benzylthio)-2,5-dichlorophenyl)methanol

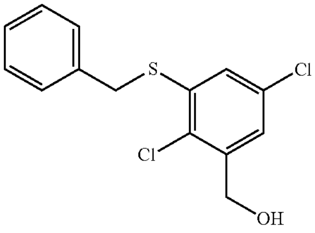 [SMILES: OCc1cc(Cl)cc(SCc2ccccc2)c1Cl]

A mixture of $CaCl_2$ (0.45 g, 0.92 mmol) and $NaBH_4$ (6.20 g, 37 mmol) in EtOH (200 mL) was stirred at 0° C. A cold solution of ethyl 3-(benzylthio)-2,5-dichlorobenzoate (F1, 14.0 g, 9.2 mmol) in THF (200 mL) was added in drop-wise manner at 0° C. The reaction mixture was stirred 0° C., slowly warmed to rt, and then heated at 60° C. for 5 h. The reaction mixture was cooled to rt, quenched with sat'd $NH_4C_1$ solution (50 ml), and then extracted with EtOAc (3×). The combined organic extracts were dried over anhydrous $Na_2SO_4$, filtered, and concentrated under reduced pressure. The crude was purified by silica gel column chromatography (1 to 10% EtOAc/hex) to afford (3-(benzylthio)-2,5-dichlorophenyl)methanol (8.0 g, 66%) as a brown solid. $^1$H NMR (400 MHz, DMSO-$d_6$): δ 7.44 (m, 2H), 7.35 (m, 3H), 7.25-7.32 (m, 2H), 5.57 (t, J=5.6 Hz, 1H), 4.51 (d, J=6.0 Hz, 2H), 4.36 (s, 2H).

Using the General Method H above, the following Intermediates of Table G were prepared.
TABLE G
| Ex No | SM | Product | Yield (%) | 1H NMR (400 or 500 MHz, DMSO-d6): δ |
|---|---|---|---|---|
| G2 | F3 | 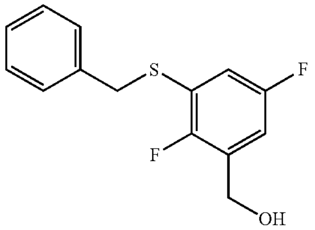 [SMILES: OCc1cc(F)cc(SCc2ccccc2)c1F] | 61 | 7.37 (m, 2H), 7.31 (m, 2H), 7.23 (m, 1H), 7.12 (m, 1H), 7.03 (m, 1H), 5.41 (t, J = 6.0 Hz, 1H), 4.50 (d, J = 5.6 Hz, 2H), 4.29 (s, 2H) |
| G3 | F4 | 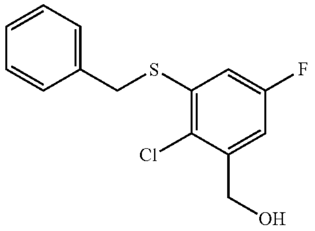 [SMILES: OCc1cc(F)cc(SCc2ccccc2)c1Cl] | 69 | 7.44 (m, 2H), 7.34-7.39 (m, 2H), 7.27 (m, 1H), 7.20 (m, 1H), 7.09 (m, 1H), 5.57 (t, J = 5.6 Hz, 1H), 4.50 (d, J = 5.6 Hz, 2H), 4.34 (s, 2H) |
| G4 | F5 | 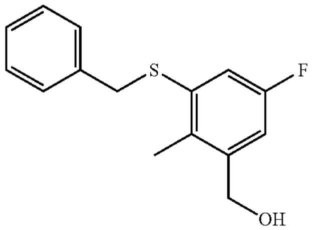 [SMILES: Cc1c(CO)cc(F)cc1SCc1ccccc1] | 69 | 7.40 (m, 2H), 7.32 (t, J = 7.2 Hz, 2H), 7.27 (m, 1H), 7.20 (m, 1H), 7.00 (m, 1H), 5.06 (s, 2H), 4.27 (s, 2H), 2.15 (s, 3H), 2.07 (s, 3H). |
| G5 | F6 | 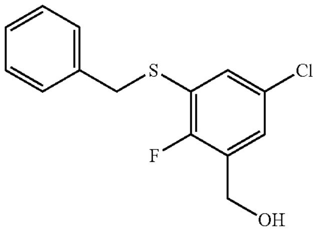 [SMILES: OCc1cc(Cl)cc(SCc2ccccc2)c1F] | 76 | 7.36 (m, 2H), 7.33 (m, 2H), 7.23-7.29 (m, 3H), 5.15 (t, J = 6.0 Hz, 1H), 4.50 (d, J = 5.6 Hz, 2H), 4.30 (s, 2H). |
| G6 | F7 | 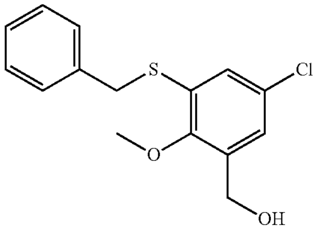 [SMILES: COc1c(CO)cc(Cl)cc1SCc1ccccc1] | 98 | 7.36 (m, 2H), 7.32 (m, 2H), 7.26 (m, 3H), 5.28 (t, J = 5.2 Hz, 1H), 4.46 (d, J = 5.2 Hz, 2H), 4.23 (s, 2H), 2.12 (s, 3H). |
| G7 | F8 | 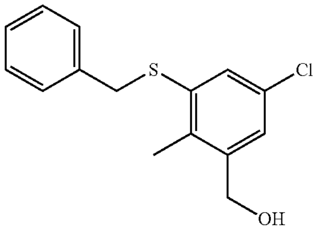 [SMILES: Cc1c(CO)cc(Cl)cc1SCc1ccccc1] | 87 | 7.36 (m, 2H), 7.32 (m, 2H), 7.26 (m, 3H), 5.28 (t, J = 5.2 Hz, 1H), 4.46 (d, J = 5.2 Hz, 2H), 4.23 (s, 2H), 2.12 (s, 3H) |

TABLE G-continued

| Ex No | SM | Product | Yield (%) | 1H NMR (400 or 500 MHz, DMSO-d6): δ |
|---|---|---|---|---|
| G8 | F9 | 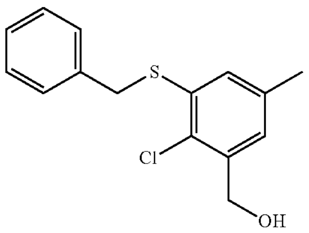 [SMILES: Cc1cc(CO)c(Cl)c(SCc2ccccc2)c1] | 97 | 7.40 (d, J = 7.2 Hz, 2H), 7.32 (t, J = 7.2 Hz, 2H), 7.25 (m, 1H), 7.16 (s, 2H), 5.36 (t, J = 5.6 Hz, 1H), 4.49 (d, J = 5.6 Hz, 2H), 4.26 (s, 3H), 2.28 (s, 3H). |
| G9 | F2 | 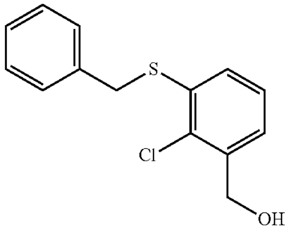 [SMILES: OCc1cccc(SCc2ccccc2)c1Cl] | crude | No Data |
| G10 | F10 | 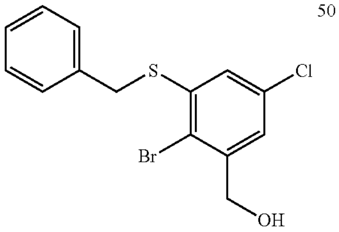 | 50 | 7.34-7.38 (m, 5H), 7.21 (br s, 1H), 7.14 (br s, 1H), 5.33 (t, J = 6.0 Hz, 1H), 4.44 (d, J = 6.0 Hz, 2H), 4.29 (s, 2H). |

General Method I: Acetylation

Example H1: 3-(benzylthio)-2,5-dichlorobenzyl acetate

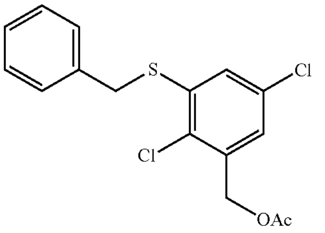 [SMILES: CC(=O)OCc1cc(Cl)cc(SCc2ccccc2)c1Cl]

A solution of (3-(benzylthio)-2,5-dichlorophenyl)methanol (G1, 0.82 g, 2.7 mmol) in THF (10 mL) was treated with acetic anhydride (0.31 mL, 3.3 mmol) at rt. The mixture was stirred at 50° C. under Ar for 2 h and then diluted with water. The solution was extracted with EtOAc (3×) and the combined organic layers were dried over anhydrous $Na_2SO_4$, filtered, and concentrated under reduced pressure to obtain 3-(benzylthio)-2,5-dichlorobenzyl acetate (0.92 g, 98%) as a white solid. $^1$H NMR (400 MHz, DMSO-$d_6$): δ 7.51 (m, 3H), 7.41 (m, 3H), 7.35 (m, 1H), 5.16 (s, 2H), 4.45 (s, 2H), 2.16 (s, 3H).

Using the General Method I above, the following Intermediates of Table H were prepared.

TABLE H

| Ex No | SM | Product | Yield (%) | 1H NMR (400 or 500 MHz, DMSO-d6): δ |
|---|---|---|---|---|
| H2 | G2 | 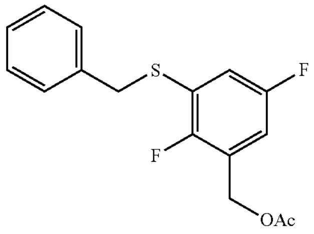 | 46 | 7.39 (m, 2H), 7.31 (m, 3H), 7.26 (m, 1H), 7.12 (m, 1H), 5.06 (s, 2H), 4.32 (s, 2H), 2.06 (s, 3H). |

TABLE H-continued
| Ex No | SM | Product | Yield (%) | 1H NMR (400 or 500 MHz, DMSO-d6): δ |
|---|---|---|---|---|
| H3 | G3 | 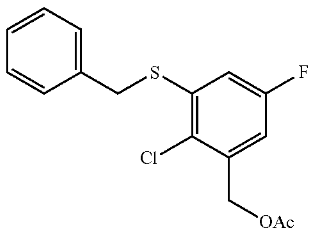 [SMILES: CC(=O)OCc1cc(F)cc(SCc2ccccc2)c1Cl] | 55 | 7.42 (m, 2H), 7.27-7.35 (m, 4H), 7.13 (m, 1H), 5.10 (s, 2H), 4.36 (s, 2H), 2.10 (s, 3H). |
| H4 | G4 | 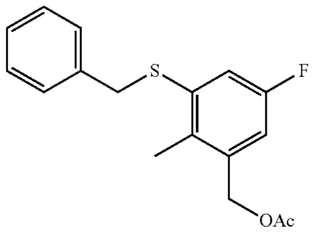 [SMILES: CC(=O)OCc1cc(F)cc(SCc2ccccc2)c1C] | 63 | 7.33-7.39 (m, 2H), 7.25-7.32 (m, 2H), 7.17-7.22 (m, 1H), 7.15 (m, 1H), 7.00 (m, 1H), 5.06 (s, 2H), 4.27 (s, 2H), 2.15 (s, 3H), 2.07 (s, 3H). |
| H5 | G5 | 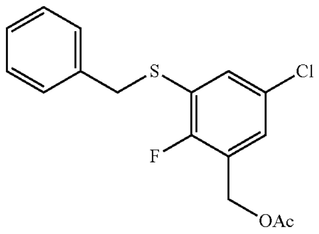 [SMILES: CC(=O)OCc1cc(Cl)cc(SCc2ccccc2)c1F] | 70 | 7.48 (dd, J = 2.4 & 5.6 Hz, 1H), 7.38-7.29 (m, 5H), 7.27 (m, 1H), 5.05 (s, 2H), 4.33 (s, 2H), 2.06 (s, 3H). |
| H6 | G6 | 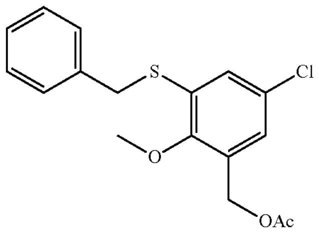 [SMILES: COc1c(COC(C)=O)cc(Cl)cc1SCc1ccccc1] | 99 | 7.40 (d, J = 7.2 Hz, 2H), 7.36 (d, J = 2.4 Hz, 1H), 7.32 (t, J = 7.2 Hz, 2H), 7.25 (m, 1H), 7.21 (d, J = 2.4 Hz, 1H), 5.03 (s, 2H), 4.29 (s, 2H), 3.71 (s, 3H), 2.00 (s, 3H). |
| H7 | G7 | 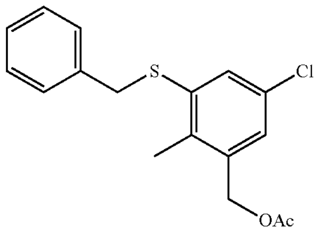 [SMILES: CC(=O)OCc1cc(Cl)cc(SCc2ccccc2)c1C] | 94 | 7.38 (m, 3H), 7.31 (t, J = 6.8 Hz, 2H), 7.27 (m, 1H), 7.21 (m, 1H), 5.06 (d, J = 4.4 Hz, 2H), 4.27 (s, 2H), 2.17 (s, 3H), 2.06 (s, 3H). |
| H8 | G8 | 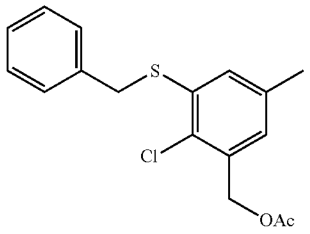 [SMILES: CC(=O)OCc1cc(C)cc(SCc2ccccc2)c1Cl] | 98 | 7.42 (d, J = 7.2 Hz, 2H), 7.35 (t, J = 7.2 Hz, 2H), 7.27 (m, 2H), 7.22 (m, 1H), 5.08 (s, 2H), 4.29 (s, 2H), 2.28 (s, 3H), 2.05 (s, 3H). |

TABLE H-continued

| Ex No | SM | Product | Yield (%) | 1H NMR (400 or 500 MHz, DMSO-d6): δ |
|---|---|---|---|---|
| H9 | G9 | 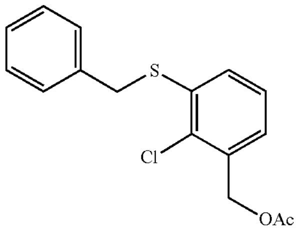 [SMILES: CC(=O)OCc1cccc(SCc2ccccc2)c1Cl] | 94 | No Data |
| H10 | G1 | 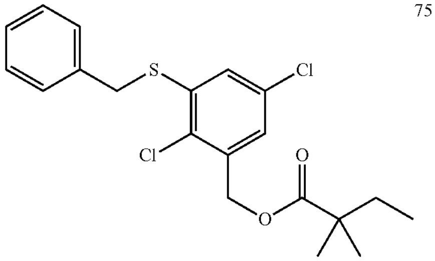 | 75 | 7.30-7.46 (m, 7H), 5.10 (s, 2H), 4.38 (s, 2H), 1.49 (m, 2H), 1.08 (s, 6H), 0.77 (t, J = 5.2 Hz, 3H). |
| H11 | G10 | 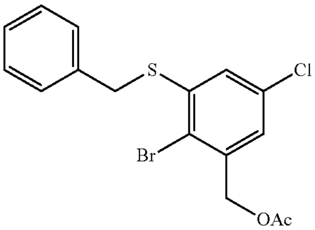 | 90 | 7.33-7.41 (m, 5H), 7.16-7.30 (m, 2H), 5.08 (s, 2H), 4.38 (s, 2H), 2.10 (s, 3H). |

General Method J: Preparation of Sulfonyl Chlorides

Example I1: 2,5-dichloro-3-(chlorosulfonyl)benzyl acetate

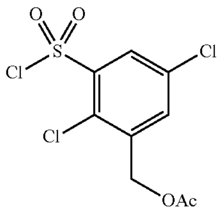 [SMILES: CC(=O)OCc1cc(Cl)cc(S(=O)(=O)Cl)c1Cl]

A solution of 3-(benzylthio)-2,5-dichlorobenzyl acetate (H1, 0.92 g, 2.7 mmol) and 1-chloropyrrolidine-2,5-dione (1.8 g, 13 mmol) in THF/$H_2O$ (1:1, 3 mL) at 0° C. was treated with acetic acid (7 mL). The reaction mixture was slowly warmed to rt and then stirred at rt for 6 h. The reaction mixture was quenched with sat'd $NaHCO_3$ solution (100 mL) and extracted with EtOAc (3×). The combined organics were dried over anhydrous $Na_2SO_4$, filtered, and concentrated under reduced pressure. The crude was purified by silica gel column chromatography (0 to 100% EtOAc/hex) to afford 2,5-dichloro-3-(chlorosulfonyl)benzyl acetate (0.45 g, 53%) as a white solid. $^1$H NMR (400 MHz, DMSO-$d_6$): δ 7.84 (d, J=2.8 Hz, 1H), 7.52 (d, J=2.8 Hz, 1H), 5.13 (s, 2H), 2.11 (s, 3H).

Using the General Method J above, the following Intermediates of Table I were prepared.

TABLE I

| Ex No | SM | Product | Yield (%) | 1H NMR (400 or 500 MHz, DMSO-d6): δ |
|---|---|---|---|---|
| I2 | 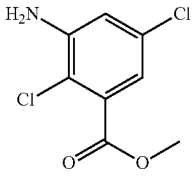 | 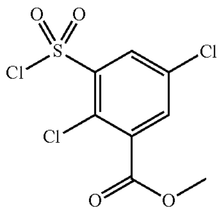 [SMILES: COC(=O)c1cc(Cl)cc(S(=O)(=O)Cl)c1Cl] | 53 | 7.99 (d, J = 2.7 Hz, 1H), 7.74 (d, J = 2.7 Hz, 1H), 3.87 (s, 4H). |

TABLE I-continued
| Ex No | SM | Product | Yield (%) | 1H NMR (400 or 500 MHz, DMSO-d6): δ |
|---|---|---|---|---|
| I3 | H2 | 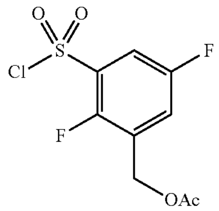 [SMILES: CC(=O)OCc1cc(F)cc(S(=O)(=O)Cl)c1F] | 59 | 7.35 (m, 1H), 7.27 (m, 1H), 5.08 (s, 2H), 2.08 (s, 3H). |
| I4 | H3 | 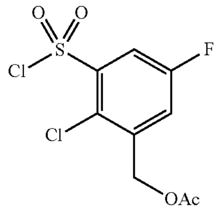 [SMILES: CC(=O)OCc1cc(F)cc(S(=O)(=O)Cl)c1Cl] | 57 | 7.61 (dd, J = 8.4, 3.2 Hz, 1H), 7.32 (dd, J = 8.8, 3.2 Hz, 1H), 5.13 (s, 2H), 2.12 (s, 3H). |
| I5 | H4 | 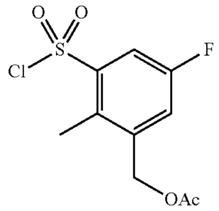 [SMILES: CC(=O)OCc1cc(F)cc(S(=O)(=O)Cl)c1C] | 72 | 7.49 (dd, J = 9.2, 2.8 Hz, 1H), 7.14 (dd, J = 9.2, 2.8 Hz, 1H), 5.07 (s, 2H), 2.44 (s, 3H), 2.08 (s, 3H). |
| I6 | H5 | 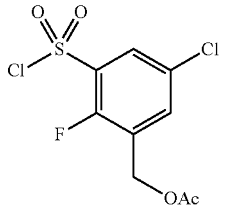 [SMILES: CC(=O)OCc1cc(Cl)cc(S(=O)(=O)Cl)c1F] | 84 | 7.60 (dd, J = 5.6, 2.8 Hz, 1H), 7.50 (dd, J = 5.6, 2.8 Hz, 1H), 5.08 (s, 2H), 2.07 (s, 3H). |
| I7 | H6 | 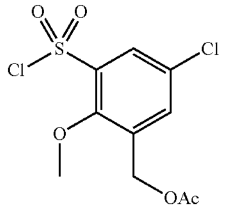 [SMILES: COc1c(COC(C)=O)cc(Cl)cc1S(=O)(=O)Cl] | 47 | No Data |
| I8 | H7 | 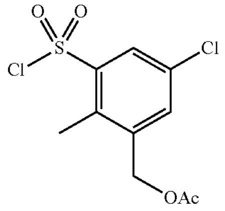 | 41 | 7.74 (d, J = 2.0 Hz, 1H), 7.35 (d, J = 2.0 Hz, 1H), 5.07 (s, 2H), 2.46 (s, 3H), 2.07 (s, 3H). |
| I9 | H8 | 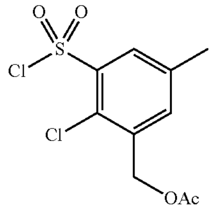 [SMILES: CC(=O)OCc1cc(C)cc(S(=O)(=O)Cl)c1Cl] | 37 | 7.70 (d, J = 1.2 Hz, 1H), 7.23 (s, 1H ), 5.10 (s, 2H), 2.28 (s, 3H), 2.08 (s, 3H). |

TABLE I-continued

| Ex No | SM | Product | Yield (%) | 1H NMR (400 or 500 MHz, DMSO-d6): δ |
|---|---|---|---|---|
| I10 | H9 | 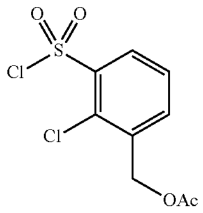 [SMILES: CC(=O)OCc1cccc(S(=O)(=O)Cl)c1Cl] | 92 | 7.88 (d, J = 7.2 Hz, 1H), 7.29 (m, 1H ), 7.43 (d, J = 7.2 Hz, 1H), 5.15 (s, 2H), 2.09 (s, 3H). |
| I11 | H10 | 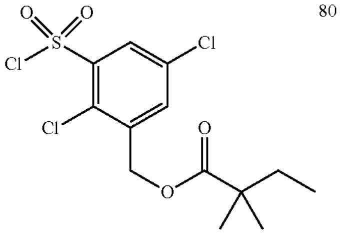 | 80 | 7.85 (d, J = 2.8 Hz, 1H), 7.48 (d, J = 2.8 Hz, 1H), 5.11 (s, 2H), 1.46 (m, 2H), 1.05 (s, 6H), 0.83 (t, J = 5.2 Hz, 3H). |
| I12 | H11 | 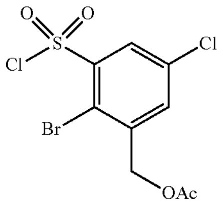 [SMILES: CC(=O)OCc1cc(Cl)cc(S(=O)(=O)Cl)c1Br] | 32 | 7.88 (d, J = 2.8 Hz, 1H), 7.47 (d, J = 2.8 Hz, 1H), 5.12 (s, 2H), 2.14 (s, 3H). |

General Method K: Sulfonamide Coupling

Example J1: methyl 2,5-dichloro-3-(N-(2-fluoro-3-(4,4,5,5-tetramethyl-1,3,2-dioxaborolan-2-yl)phenyl) sulfamoyl)benzoate

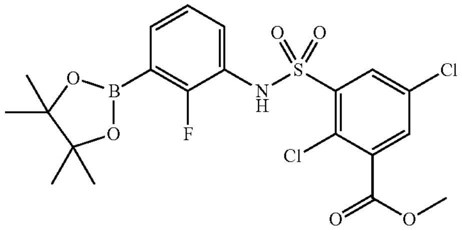

A solution of 2-fluoro-3-(4,4,5,5-tetramethyl-1,3,2-dioxaborolan-2-yl)aniline (A1 2.2 g, 9.3 mmol) in DCM (30 mL) was treated with pyridine (2.2 mL, 28 mmol). The reaction mixture was cooled to 0° C. and a solution of methyl 2,5-dichloro-3-(chlorosulfonyl)benzoate (122.8 g, 9.3 mmol) in DCM (10 mL) was added dropwise. The reaction mixture was slowly warmed to rt for 2 h. The reaction mixture was concentrated under reduced pressure and the crude was dissolved in DCM (50 mL). The solution was washed with 1.0 M HCl (2×), aqueous $NaHCO_3$ (3×) and brine (1×). The organic layer was dried over anhydrous $Na_2SO_4$, filtered, and concentrated under reduced pressure. The residue was suspended in hex and the solids were collected via vacuum filtration to obtain methyl 2,5-dichloro-3-(N-(2-fluoro-3-(4,4,5,5-tetramethyl-1,3,2-dioxaborolan-2-yl)phenyl)sulfamoyl)benzoate (4.2 g, 90%) as a brown solid. $^1H$ NMR (500 MHz, DMSO-$d_6$): δ 10.71 (s, 1H), 8.13 (d, J=2.6 Hz, 1H), 8.02 (d, J=2.6 Hz, 1H), 7.46 (m, 1H), 7.38 (td, J=7.9, 1.8 Hz, 1H), 7.16 (t, J=7.7 Hz, 1H), 3.91 (s, 3H), 1.28 (s, 12H); MS (ESI) m/z 526.0 (M+Na+$H^+$).

General Method L: Reduction

Preparation of Example J2: 2,5-dichloro-N-(2-fluoro-3-(4,4,5,5-tetramethyl-1,3,2-dioxaborolan-2-yl)phenyl)-3-(hydroxymethyl)benzenesulfonamide

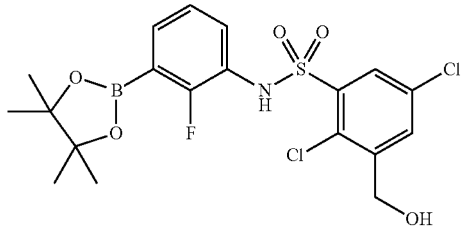 [SMILES: CC1(C)OB(c2cccc(NS(=O)(=O)c3cc(Cl)cc(CO)c3Cl)c2F)OC1(C)C]

A solution of methyl 2,5-dichloro-3-(N-(2-fluoro-3-(4,4,5,5-tetramethyl-1,3,2-dioxaborolan-2-yl)phenyl)sulfamoyl) benzoate (J1, 0.5 g, 0.99 mmol) in THF (5 mL) was treated with LAH (0.11 g, 30 mmol) portion-wise at 0° C. and then stirred at 0° C. for 1 h. The reaction mixture was diluted with diethyl ether and then quenched with water (0.2 mL), 15% aqueous NaOH (0.2 mL) and water (0.4 mL). The mixture was stirred for 4 h and then filtered through a pad of celite. The filtrate was dried over anhydrous $Na_2SO_4$, filtered and concentrated under reduced pressure to obtain 2,5-dichloro-N-(2-fluoro-3-(4,4,5,5-tetramethyl-1,3,2-dioxaborolan-2-yl)phenyl)-3-(hydroxymethyl)benzenesulfonamide (0.26 g, 55%) as colorless solid which was used for the next reaction without further purification. MS (ESI) m/z 498.0 (M+Na+$H^+$).

Using the General Methods K and L above, the following Intermediates of Table J were prepared.

TABLE J

| Ex. No. | SM | Product | Yield (%) | $^1$H NMR (400 or 500 MHz, DMSO-$d_6$): δ | MS (m/z: M + H$^+$) |
|---|---|---|---|---|---|
| J3 | A1 I1 | 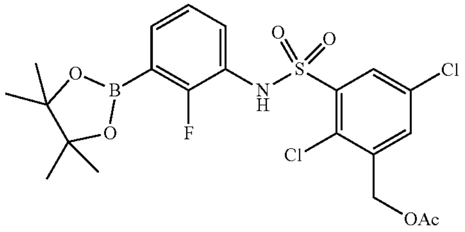 [SMILES: CC(=O)OCc1cc(Cl)cc(S(=O)(=O)Nc2cccc(B3OC(C)(C)C(C)(C)O3)c2F)c1Cl] | 77 | 10.64 (br s, 1H), 7.85 (m, 2H), 7.41 (m, 1H), 7.35 (m, 1H), 7.12 (t, J = 7.6 Hz, 1H), 5.13 (s, 2H), 2.12 (s, 3H), 1.26 (s, 12H). | 516.0 (negative) |
| J4 | A3 I1 | 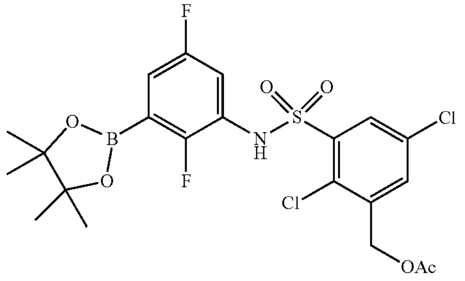 [SMILES: CC(=O)OCc1cc(Cl)cc(S(=O)(=O)Nc2cc(F)cc(B3OC(C)(C)C(C)(C)O3)c2F)c1Cl] | crude | No Data | 452 (negative) boronic acid mass |
| J5 | A5 I1 | 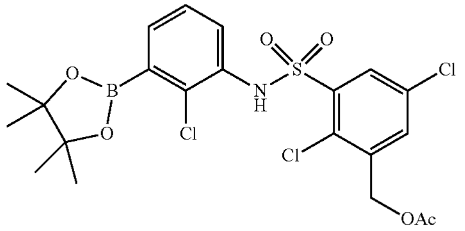 [SMILES: CC(=O)OCc1cc(Cl)cc(S(=O)(=O)Nc2cccc(B3OC(C)(C)C(C)(C)O3)c2Cl)c1Cl] | crude | 10.50 (br s, 1H), 7.87 (d, J = 2.4 Hz, 1H), 7.85 (d, J = 2.8 Hz, 1H), 7.79 (d, J = 2.4 Hz, 1H), 7.52 (d, J = 2.8 Hz, 1H), 7.47 (dd, J = 6.4, 2.8 Hz, 1H), 5.22 (s, 2H), 2.12 (s, 3H). | No Data |
| J6 | A1 I4 | 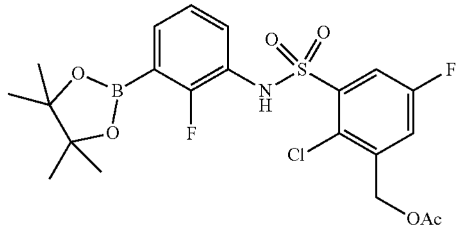 [SMILES: CC(=O)OCc1cc(F)cc(S(=O)(=O)Nc2cccc(B3OC(C)(C)C(C)(C)O3)c2F)c1Cl] | 86 | 10.61 (br s, 1H), 7.70 (m, 1H), 7.55 (t, J = 7.2 Hz, 1H), 7.43 (t, J = 5.6 Hz, 1H), 7.35 (t, J = 7.6 Hz, 1H), 7.13 (t, J = 7.6 Hz, 1H), 5.21 (s, 2H), 2.13 (s, 3H), 1.22 (s, 12H) | |
| J7 | A1 I5 | 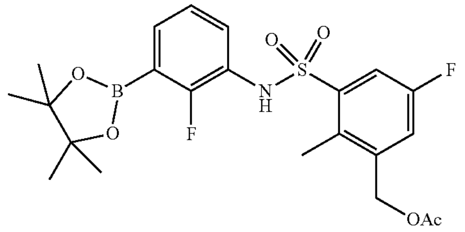 [SMILES: CC(=O)OCc1cc(F)cc(S(=O)(=O)Nc2cccc(B3OC(C)(C)C(C)(C)O3)c2F)c1C] | crude | No Data | No Data |
| J8 | A1 I7 | 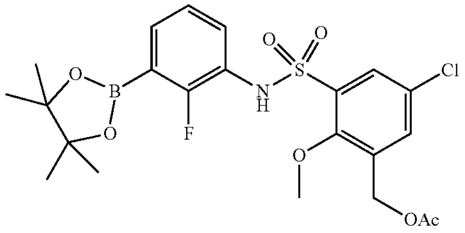 [SMILES: COc1c(COC(C)=O)cc(Cl)cc1S(=O)(=O)Nc1cccc(B2OC(C)(C)C(C)(C)O2)c1F] | 98 | 10.15 (br s, 1H), 7.74 (m, 1H), 7.64 (d, J = 2.8 Hz, 1H), 7.41 (t, J = 5.6 Hz, 1H), 7.33 (t, J = 7.6 Hz, 1H), 7.11 (t, J = 8.0 Hz, 1H), 5.14 (s, 2H), 3.84 (s, 3H), 2.10 (s, 3H), 1.27 (s, 12H) | 512.2 |

TABLE J-continued
| Ex. No. | SM | Product | Yield (%) | $^1$H NMR (400 or 500 MHz, DMSO-$d_6$): δ | MS (m/z: M + $H^+$) |
|---|---|---|---|---|---|
| J9 | A1 I6 | 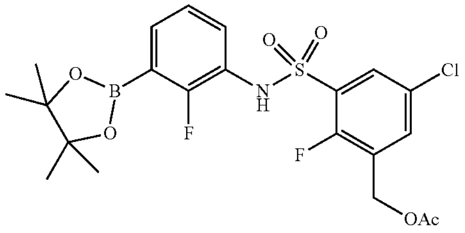 [SMILES: CC(=O)OCc1cc(Cl)cc(S(=O)(=O)Nc2cccc(B3OC(C)(C)C(C)(C)O3)c2F)c1F] | 60 | 7.88 (m, 1H), 7.66 (m, 1H), 7.45-7.51 (m, 1H), 7.38 (m, 1H), 7.15 (m, 1H), 5.14 (s, 2H), 2.07 (s, 3H), 1.26 (s, 12H). NH is missing | No Data |
| J10 | A1 I8 | 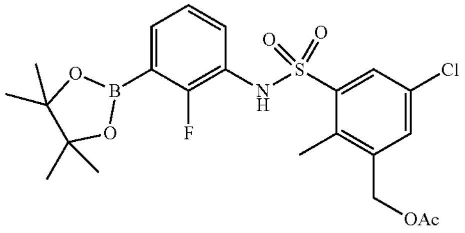 [SMILES: CC(=O)OCc1cc(Cl)cc(S(=O)(=O)Nc2cccc(B3OC(C)(C)C(C)(C)O3)c2F)c1C] | crude | 10.49 (br s, 1H), 7.71 (m, 2H), 7.33-7.42 (m, 2H), 7.13 (t, J = 7.6 Hz, 1H), 5.16 (s, 2H), 2.53 (s, 3H), 2.09 (s, 3H), 1.26 (s, 12H). | |
| J11 | A2 I1 | 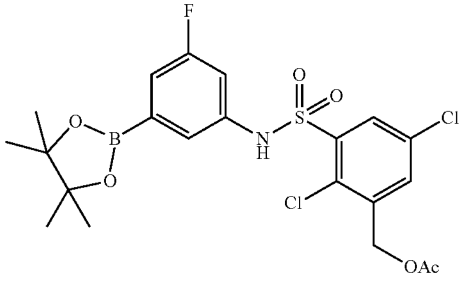 [SMILES: CC(=O)OCc1cc(Cl)cc(S(=O)(=O)Nc2cc(F)cc(B3OC(C)(C)C(C)(C)O3)c2)c1Cl] | crude | No Data | 434.2 boronic acid |
| J12 | A4 I1 | 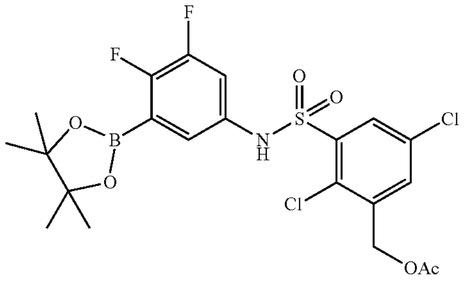 [SMILES: CC(=O)OCc1cc(Cl)cc(S(=O)(=O)Nc2cc(F)c(F)c(B3OC(C)(C)C(C)(C)O3)c2)c1Cl] | crude | No Data | 452.2 boronic acid |
| J13 | A1 I9 | 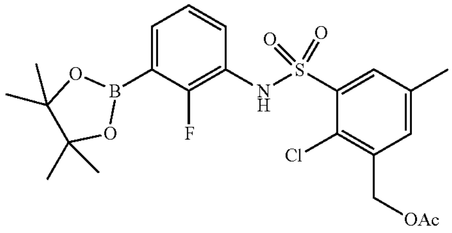 | crude | No Data | 414.0 boronic acid |
| J14 | A1 I10 | 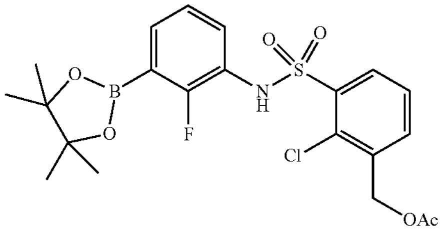 [SMILES: CC(=O)OCc1cccc(S(=O)(=O)Nc2cccc(B3OC(C)(C)C(C)(C)O3)c2F)c1Cl] | crude | No Data | 424.0 boronic acid + Na |

TABLE J-continued

| Ex. No. | SM | Product | Yield (%) | $^1$H NMR (400 or 500 MHz, DMSO-$d_6$): δ | MS (m/z: M + $H^+$) |
|---|---|---|---|---|---|
| J15 | A1 I11 | 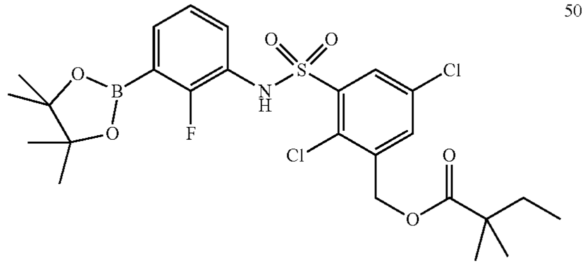 | 50 | 10.15 (br s, 1H), 7.88 (d, J = 2.4 Hz, 1H), 7.82 (d, J = 2.0 Hz, 1H), 7.78 (m, 1H), 7.07-7.11 (br m, 1H), 6.73-6.76 (br m, 1H), 5.19 (s, 2H), 1.53 (m, 2H), 1.27 (s, 12H), 1.13 (s, 6H), 0.76 (t, J = 4.4 Hz, 3H). | 572.0 (negative) |
| J16 | A1 I12 | 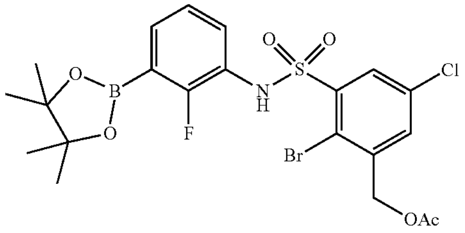 [SMILES: CC(=O)OCc1cc(Cl)cc(S(=O)(=O)Nc2cccc(B3OC(C)(C)C(C)(C)O3)c2F)c1Br] | 60 | 10.59 (br s, 1H), 8.82 (m, 2H), 8.32 (t, J = 7.6 Hz, 1H), 7.82-8.03 (m, 2H), 5.12 (s, 2H), 2.13 (s, 3H), 1.27 (s, 12H). | 561.9 |

General Method M: Suzuki Reaction

Example 1: 3-(N-(3-(4-amino-7-methyl-7H-pyrrolo[2,3-d]pyrimidin-5-yl)-2-fluorophenyl)sulfamoyl)-2,5-dichlorobenzyl acetate

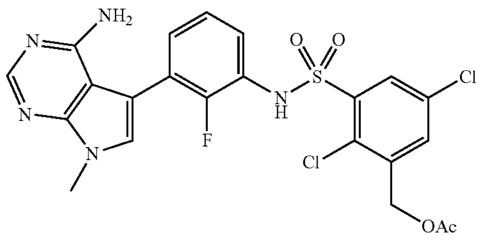 [SMILES: CC(=O)OCc1cc(Cl)cc(S(=O)(=O)Nc2cccc(-c3cn(C)c4ncnc(N)c34)c2F)c1Cl]

A solution of 5-iodo-7-methyl-7H-pyrrolo[2,3-d]pyrimidin-4-amine (1.7 g, 6.3 mmol) in a mixture of 1,4-dioxane and water (4:1, 100 mL) was stirred under Ar. 2,5-Dichloro-3-(N-(2-fluoro-3-(4,4,5,5-tetramethyl-1,3,2-dioxaborolan-2-yl)phenyl)sulfamoyl)benzyl acetate (3.6 g, 6.9 mmol) and $Cs_2CO_3$ (5.1 g, 15.7 mmol) was added at rt and the reaction mixture was degassed with Ar for 5 min. Pd(dppf)$Cl_2$.DCM (0.25 g, 0.31 mmol) was added and the resulting mixture was heated at 90° C. for 1.5 h. The reaction mixture was cooled to rt and filtered through a pad of celite, washed with EtOAc. The filtrate was washed with sat'd $NaHCO_3$ (2×), followed by water (2×). The organic layer was dried over anhydrous $Na_2SO_4$, filtered, and concentrated under reduced pressure to obtain crude material. The crude material was further stirred in $CH_3CN$ (300 mL) at rt for 2 h. The solids were filtered and dried under vacuum to afford 3-(N-(3-(4-amino-7-methyl-7H-pyrrolo[2,3-d]pyrimidin-5-yl)-2-fluorophenyl)sulfamoyl)-2,5-dichlorobenzyl acetate (2.5 g, 91%) as a light brown solid. $^1$H NMR (400 MHz, DMSO-$d_6$): δ 10.76 (br s, 1H), 8.14 (s, 1H), 7.93 (d, J=2.4 Hz, 1H), 7.84 (m, 1H), 7.26 (s, 1H), 7.19 (m, 3H), 6.02 (br s, 2H), 5.20 (s, 2H), 3.73 (s, 3H), 3.56 (s, 3H); MS (ESI) m/z 538.0 (M+$H^{\pm}$).

General Method N: Deprotection

Example 2: N-(3-(4-amino-7-methyl-7H-pyrrolo[2,3-d]pyrimidin-5-yl)-2-fluorophenyl)-2,5-dichloro-3-(hydroxymethyl)benzenesulfonamide

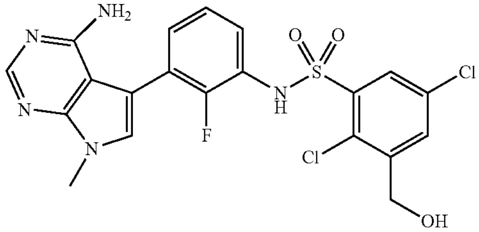 [SMILES: Cn1cc(-c2cccc(NS(=O)(=O)c3cc(Cl)cc(CO)c3Cl)c2F)c2c(N)ncnc21]

A solution of 3-(N-(3-(4-amino-7-methyl-7H-pyrrolo[2,3-d]pyrimidin-5-yl)-2-fluorophenyl)sulfamoyl)-2,5-dichlorobenzyl acetate (1, 2.3 g, 4.2 mmol) in MeOH (40 mL) was treated with $K_2CO_3$ (2.3 g, 17 mmol) at rt. The mixture was stirred at rt for 3 h and then solvent was evaporated under reduced pressure. The crude material was acidified with 10% citric acid solution (pH-5) and then the solid was filtered and washed thoroughly with water. The solid was treated with a mixture of $CH_3CN$ (5 mL) and DCM (5 mL) at rt for 2 h. The precipitates were filtered and dried to obtained N-(3-(4-amino-7-methyl-7H-pyrrolo[2,3-d]pyrimidin-5-yl)-2-fluorophenyl)-2,5-dichloro-3-(hydroxymethyl) benzenesulfonamide (1.6 g, 76%) as an off-white solid. $^1$H NMR (400 MHz, DMSO-$d_6$) δ 10.69 (br s, 1H), 8.14 (s, 1H), 7.84 (d, J=2.4 Hz, 1H), 7.78 (br m, 1H), 7.27 (s, 1H), 7.15-7.25 (br m, 3H), 5.99 (br s, 2H), 5.72 (t, J=5.6 Hz, 1H), 4.60 (d, J=5.6 Hz, 2H), 3.73 (s, 3H). MS (ESI) m/z 496.27 (M+$H^+$).

Using the General Methods L, M and N above, the following Intermediates of Table K were prepared.

TABLE K

| Ex. No | SM | Product | Method | Yield (%) | $^1$H NMR (400 or 500 MHz, DMSO-$d_6$): δ | MS (m/z: M + H$^+$) |
|---|---|---|---|---|---|---|
| 3 | E1 J2 | 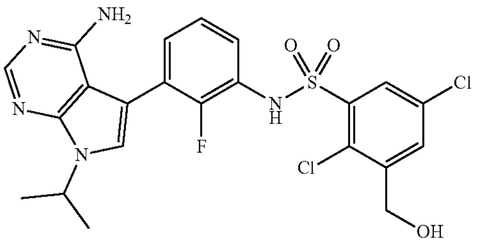 [SMILES: CC(C)n1cc(-c2cccc(NS(=O)(=O)c3cc(Cl)cc(CO)c3Cl)c2F)c2c(N)ncnc21] | M | 13 | 10.73 (s, 1H), 8.13 (d, J = 1.1 Hz, 1H), 7.86 (d, J = 2.6 Hz, 1H), 7.78 (d, J = 2.6 Hz, 1H), 7.39 (s, 1H), 7.14-7.27 (m, 3H), 6.00 (s, 2H), 5.75 (t, J = 6.3 Hz, 1H), 4.95 (m, 1H), 4.61 (d, J = 5.7 Hz, 2H), 1.44 (d, J = 6.7 Hz, 6H). | 524.0 |
| 4 | E3 J1 | 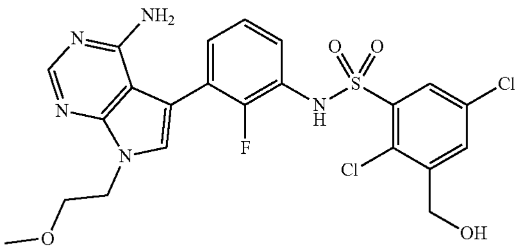 [SMILES: COCCn1cc(-c2cccc(NS(=O)(=O)c3cc(Cl)cc(CO)c3Cl)c2F)c2c(N)ncnc21] | M & L | 15 | 10.75 (s, 1H), 8.15 (s, 1H), 7.87 (d, J = 2.6 Hz, 1H), 7.79 (d, J = 2.6 Hz, 1H), 7.30 (s, 1H), 7.21 (m, 3H), 6.06 (s, 2H), 5.76 (t, J = 6.3 Hz, 1H), 4.62 (d, J = 5.6 Hz, 2H), 4.33 (t, J = 5.4 Hz, 2H), 3.69 (t, J = 5.4 Hz, 2H), 3.24 (s, 3H). | 540.0 |
| 5 | E2 J14 | 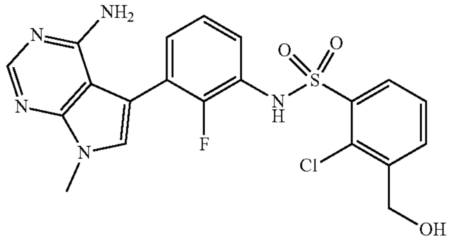 [SMILES: Cn1cc(-c2cccc(NS(=O)(=O)c3cccc(CO)c3Cl)c2F)c2c(N)ncnc21] | M & N | 6 | 1H NMR (500 MHz, DMSO) ? 10.60 (s, 1H), 8.13 (s, 1H), 7.88 (dd, J = 7.8, 1.7 Hz, 1H), 7.74-7.62 (m, 1H), 7.49-7.39 (m, 1H), 7.24 (s, 1H), 7.13-7.09 (m, 1H), 7.05-6.92 (m, 2H), 5.99 (br s, 2H), 5.52 (s, 1H), 4.59 (d, J = 5.5 Hz, 2H), 3.72 (s, 3H). | 462.0 |
| 6 | E2 J11 | 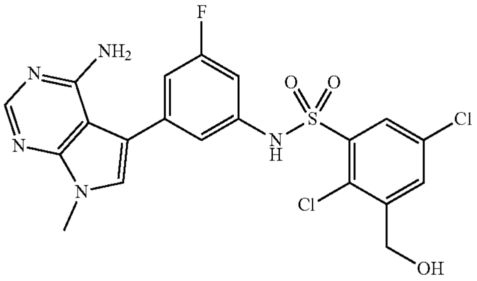 [SMILES: Cn1cc(-c2cc(F)cc(NS(=O)(=O)c3cc(Cl)cc(CO)c3Cl)c2)c2c(N)ncnc21] | M & N | 10 | 11.26 (s, 1H), 8.36 (s, 1H), 8.05 (d, J = 2.4 Hz, 1H), 7.81 (d, J = 2.4 Hz, 1H), 7.48 (s, 1H), 7.20-7.43 (br s, 2H), 6.98 (s, 1H), 6.94 (br d, J = 9.6, 1H), 6.88 (br d, J = 10.9 Hz, 1H), 5.72 (br s, 1H), 4.58 (s, 2H), 3.79 (s, 3H). | 496.2 |
| 7 | E2 J12 | 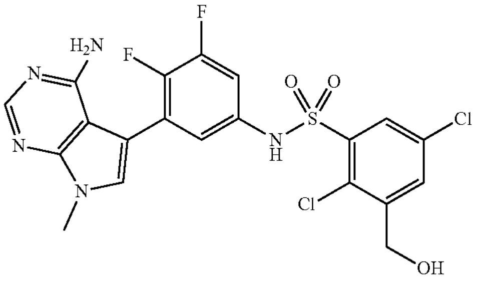 [SMILES: Cn1cc(-c2cc(NS(=O)(=O)c3cc(Cl)cc(CO)c3Cl)cc(F)c2F)c2c(N)ncnc21] | M & N | 10 | 10.77 (br s, 1H), 8.17 (s, 1H), 7.95 (d, J = 2.4 Hz, 1H), 7.79 (d, J = 2.4 Hz, 1H), 7.24 (s, 1H), 7.05 (m, 1H), 6.92 (br m, 1H), 5.90 (br s, 2H), 5.48 (t, J = 5.5 Hz, 1H), 4.61 (d, J = 4.8 Hz, 2H), 3.75 (s, 3H). at high Temp. | 514.1 |

TABLE K-continued

| Ex. No | SM | Product | Method | Yield (%) | $^1$H NMR (400 or 500 MHz, DMSO-$d_6$): δ | MS (m/z: M + $H^+$) |
|---|---|---|---|---|---|---|
| 8 | E4<br>J1 | 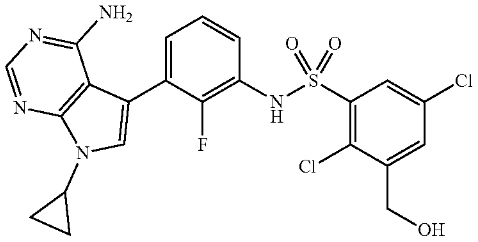 [SMILES: Nc1ncnc2c1c(-c1cccc(NS(=O)(=O)c3cc(Cl)cc(CO)c3Cl)c1F)cn2C1CC1] | M & L | 14 | 10.64 (s, 1H), 8.08 (s, 1H), 7.78 (d, J = 2.7 Hz, 1H), 7.76 (m, 1H), 7.13 (d, J = 2.8 Hz, 4H), 5.92 (s, 2H), 5.67 (t, J = 5.7 Hz, 1H), 4.54 (d, J = 5.7 Hz, 2H), 3.50 (m, 1H), 1.0 (m, 4H). | 522.0 |
| 9 | E5<br>J3 | 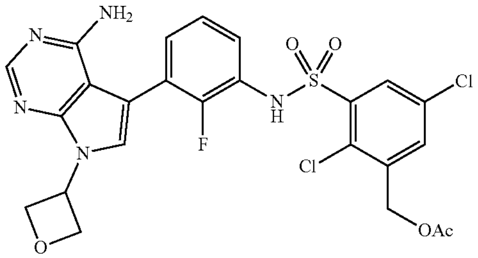 [SMILES: CC(=O)OCc1cc(Cl)cc(S(=O)(=O)Nc2cccc(-c3cn(C4COC4)c4ncnc(N)c34)c2F)c1Cl] | M | 21 | 10.80 (s, 1H), 8.15 (s, 1H), 7.96 (d, J = 2.5 Hz, 1H), 7.87 (d, J = 2.6 Hz, 1H), 7.67 (s, 1H), 7.30 (td, J = 6.3, 3.5 Hz, 1H), 7.23 (m, 2H), 6.10 (s, 2H), 5.86 (p, J = 7.2 Hz, 1H), 5.21 (s, 2H), 4.99 (m, 4H), 2.09 (s, 3H). | 580.0 |
| 10 | 9 | 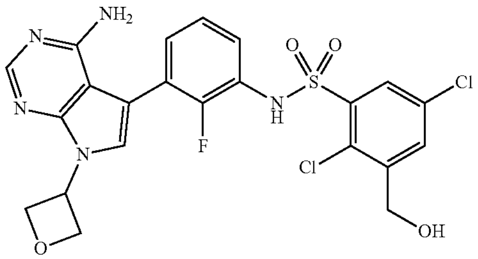 [SMILES: Nc1ncnc2c1c(-c1cccc(NS(=O)(=O)c3cc(Cl)cc(CO)c3Cl)c1F)cn2C1COC1] | N | 20 | 10.75 (s, 1H), 8.15 (s, 1H), 7.87 (d, J = 2.7 Hz, 1H), 7.80 (d, J = 2.5 Hz, 1H), 7.68 (s, 1H), 7.30 (m, 1H), 7.23 (m, 2H), 6.11 (s, 2H), 5.86 (tt, J = 7.7, 6.7 Hz, 1H), 5.75 (m, 1H), 4.99 (p, J = 6.9 Hz, 4H), 4.62 (d, J = 5.5 Hz, 2H). | 538.0 |
| 11 | 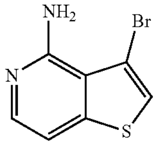<br>J1 | 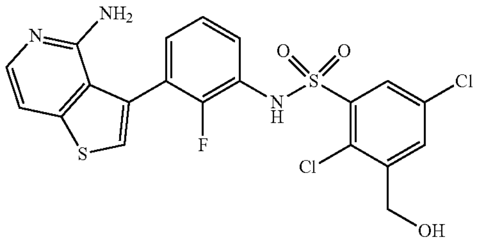 [SMILES: Nc1nccc2scc(-c3cccc(NS(=O)(=O)c4cc(Cl)cc(CO)c4Cl)c3F)c12] | M & L | 22 | 10.86 (s, 1H), 7.86 (d, J = 2.6 Hz, 1H), 7.83 (d, J = 5.6 Hz, 1H), 7.78 (d, J = 2.6 Hz, 1H), 7.53 (s, 1H), 7.38-7.33 (m, 1H), 7.29 (d, J = 5.7 Hz, 1H), 7.27-7.24 (m, 2H), 5.72 (t, J = 5.8 Hz, 1H), 5.24 (s, 2H), 4.60 (d, J = 4.8 Hz, 2H). | 499.0 |
| 12 | 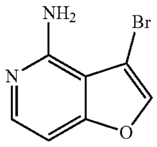<br>J1 | 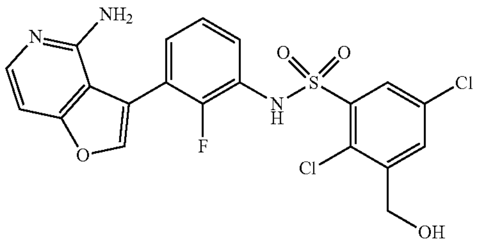 [SMILES: Nc1nccc2occ(-c3cccc(NS(=O)(=O)c4cc(Cl)cc(CO)c4Cl)c3F)c12] | M & L | 32 | 10.84 (s, 1H), 7.96 (s, 1H), 7.91-7.83 (m, 2H), 7.78 (d, J = 2.6 Hz, 1H), 7.36-7.21 (m, 3H), 6.96 (d, J = 5.9 Hz, 1H), 5.72 (t, J = 5.7 Hz, 1H), 5.45 (s, 2H), 4.61 (d, J = 5.4 Hz, 2H). | 483.0 |
| 13 | E6<br>J1 | 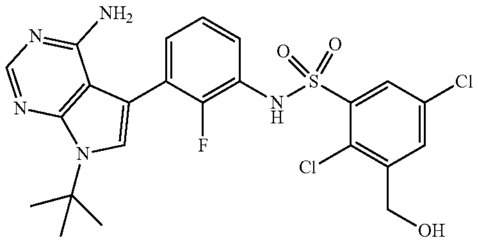 [SMILES: CC(C)(C)n1cc(-c2cccc(NS(=O)(=O)c3cc(Cl)cc(CO)c3Cl)c2F)c2c(N)ncnc21] | M & L | 15 | 10.62 (s, 1H), 8.07 (s, 1H), 7.78 (d, J = 2.6 Hz, 1H), 7.72 (d, J = 2.6 Hz, 1H), 7.13 (m, 4H), 5.85 (s, 2H), 5.66 (t, J = 5.7 Hz, 1H), 4.54 (d, J = 5.6 Hz, 2H), 1.65 (s, 9H). | 538.0 |

TABLE K-continued

| Ex. No | SM | Product | Method | Yield (%) | $^1$H NMR (400 or 500 MHz, DMSO-$d_6$): δ | MS (m/z: M + H$^+$) |
|---|---|---|---|---|---|---|
| 14 | E2<br>J4 | 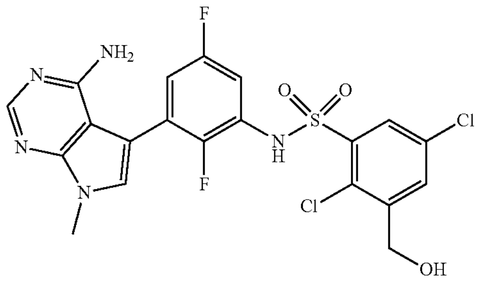 [SMILES: Cn1cc(-c2cc(F)cc(NS(=O)(=O)c3cc(Cl)cc(CO)c3Cl)c2F)c2c(N)ncnc21] | M & N | 10 | 11.03 (br s, 1H), 8.16 (s, 1H), 7.91 (d, J = 2.4 Hz, 1H), 7.79 (d, J = 2.4 Hz, 1H), 7.33 (s, 1H), 6.98-7.07 (m, 2H), 6.21 (br s, 2H), 5.72 (t, J = 5.6 Hz, 1H), 4.60 (d, J = 5.6 Hz, 2H), 3.73 (s, 3H). | 514.2 |
| 15 | E8<br>J3 | 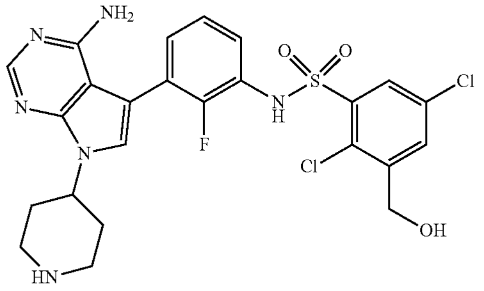 [SMILES: Nc1ncnc2c1c(-c1cccc(NS(=O)(=O)c3cc(Cl)cc(CO)c3Cl)c1F)cn2C1CCNCC1] | M & N | 23 | 8.62 (s, 2H), 8.06 (s, 1H), 7.78 (d, J = 2.7 Hz, 1H), 7.50 (d, J = 2.7 Hz, 1H), 6.99 (m, 2H), 6.85 (t, J = 7.8 Hz, 1H), 6.57 (t, J = 7.0 Hz, 1H), 5.94 (s, 2H), 5.53 (s, 1H), 4.80 (tt, J = 11.9, 4.2 Hz, 1H), 4.50 (s, 2H), 3.36 (m, 2H), 3.05 (td, J = 12.9, 3.1 Hz, 2H), 2.11 (tt, J = 12.8, 6.6 Hz, 2H), 2.03 (dd, J = 13.5, 3.6 Hz, 2H) | 565.0 |
| 16 | E7<br>J3 | 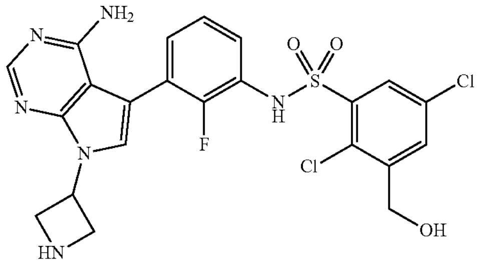 [SMILES: Nc1ncnc2c1c(-c1cccc(NS(=O)(=O)c3cc(Cl)cc(CO)c3Cl)c1F)cn2C1CNC1] | M & N | 9 | 8.10 (s, 1H), 8.08 (s, 1H), 7.80 (d, J = 2.7 Hz, 1H), 7.53 (d, J = 2.7 Hz, 1H), 7.49 (s, 1H), 7.03 (td, J = 8.1, 1.7 Hz, 1H), 6.88 (t, J = 7.8 Hz, 1H), 6.66 (s, 1H), 5.54 (p, J = 7.9 Hz, 1H), 4.46-4.53 (m, 5H), 4.32 (m, 2H). 3Hs are missing | 537.0 |
| 17 | E9<br>J3 | 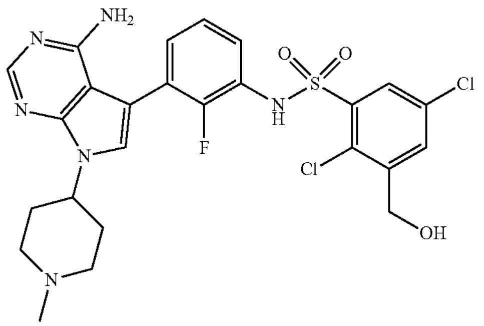 [SMILES: CN1CCC(n2cc(-c3cccc(NS(=O)(=O)c4cc(Cl)cc(CO)c4Cl)c3F)c3c(N)ncnc32)CC1] | M & N | 25 | 8.14 (s, 1H), 7.87 (d, J = 2.6 Hz, 1H), 7.71 (d, J = 2.6 Hz, 1H), 7.34 (s, 1H), 7.15 (td, J = 7.8, 1.8 Hz, 1H), 7.08 (t, J = 7.8 Hz, 1H), 7.00 (t, J = 7.2 Hz, 1H), 6.01 (s, 2H), 5.69 (s, 1H), 4.64 (m, 1H), 4.61 (s, 2H), 3.11 (m, 2H), 2.43 (s, 3H), 2.43-2.50 (m, 3H), 2.15 (m, 2H), 1.94-2.04 (m, 2H). | 580.0 |
| 18 | E12<br>J3 | 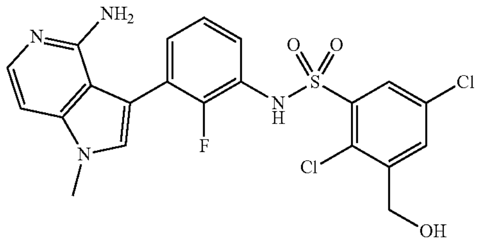 [SMILES: Cn1cc(-c2cccc(NS(=O)(=O)c3cc(Cl)cc(CO)c3Cl)c2F)c2c(N)nccc21] | M & N | 14 | 10.5 (br s, 1H), 7.86 (d, J = 2.5 Hz, 1H), 7.67 (m, 2H), 7.33 (s, 1H), 7.16 (t, J = 7.5 Hz, 1H), 7.04 (t, J = 7.7 Hz, 1H), 6.99 (d, J = 6.4 Hz, 1H), 6.91 (br m, 1H), 5.81 (br s, 2H), 5.65 (t, J = 5.9 Hz, 1H), 4.58 (d, J = 5.2 Hz, 2H), 3.79 (s, 3H) | 495.3 |

TABLE K-continued

| Ex. No | SM | Product | Method | Yield (%) | $^1$H NMR (400 or 500 MHz, DMSO-d$_6$): δ | MS (m/z: M + H$^+$) |
|---|---|---|---|---|---|---|
| 19 | E2<br>J6 | 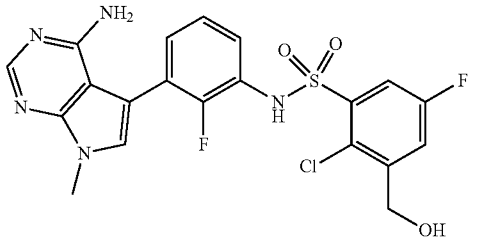 [SMILES: Cn1cc(-c2cccc(NS(=O)(=O)c3cc(F)cc(CO)c3Cl)c2F)c2c(N)ncnc21] | M & N | 35 | 10.7 (br s, 1H), 8.15 (s, 1H), 7.68 (dd, J = 8.0, 3.2 Hz, 1H), 7.60 (dd, J = 8.8, 2.8 Hz, 1H), 7.28 (s, 1H), 7.18-7.20 (m, 3H), 6.00 (br s, 2H), 5.73 (t, J = 5.6 Hz, 1H), 4.61 (d, J = 5.6 Hz, 2H), 3.73 (s, 3H). | 480.3 |
| 20 | E2<br>J5 | 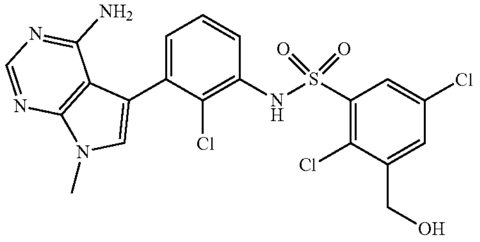 | M & N | 8 | 10.5 (br s, 1H), 8.14 (s, 1H), 7.79 (br m, 2H), 7.35 (t, J = 8.4 Hz, 1H), 7.28 (m, 1H), 7.25 (s, 1H), 7.22 (dd, J = 8.0, 1.6 Hz, 1H), 5.84 (br s, 2H), 5.72 (t, J = 5.6 Hz, 1H), 4.61 (d, J = 5.6 Hz, 2H), 3.73 (s, 3H). | 512.3 |
| 21 | 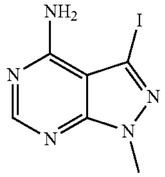<br>J3 | 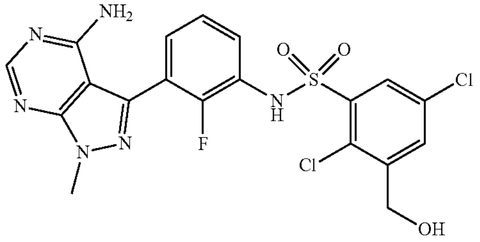 [SMILES: Cn1nc(-c2cccc(NS(=O)(=O)c3cc(Cl)cc(CO)c3Cl)c2F)c2c(N)ncnc21] | M & N | 25 | 10.74 (m, 1H), 8.25 (s, 1H), 7.87 (d, J = 2.6 Hz, 1H), 7.73 (s, 1H), 7.29 (m, 1H), 7.19 (s, 2H), 5.68 (t, J = 5.8 Hz, 1H), 4.60 (d, J = 5.7 Hz, 2H), 3.94 (s, 3H). 2Hs are missing | 497.0 |
| 22 | E2<br>J9 | 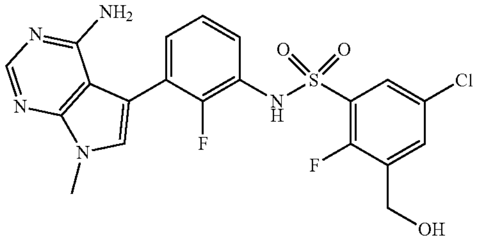 [SMILES: Cn1cc(-c2cccc(NS(=O)(=O)c3cc(Cl)cc(CO)c3F)c2F)c2c(N)ncnc21] | M & N | 25 | 10.72 (br s, 1H), 8.14 (s, 1H), 7.75 (br m, 1H), 7.61-7.67 (m, 1H), 7.26 (s, 1H), 7.18-7.25 (br m, 3H), 5.98 (br s, 2H), 5.93 (t, J = 5.6 Hz, 1H), 4.57 (d, J = 5.6 Hz, 2H), 3.73 (s, 3H). | 480.0 |
| 23 | E2<br>J7 | 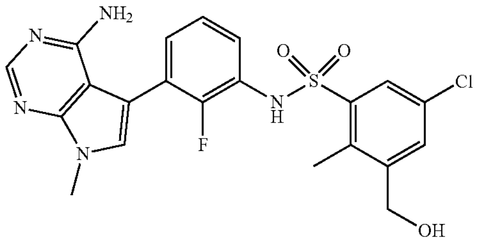 [SMILES: Cc1c(CO)cc(Cl)cc1S(=O)(=O)Nc1cccc(-c2cn(C)c3ncnc(N)c23)c1F] | M & N | 9 | 10.51 (br s, 1H), 8.14 (s, 1H), 7.44-7.52 (br m, 2H), 7.25 (s, 1H), 7.16 (br m, 3H), 5.97 (br s, 2H), 5.48 (t, J = 5.2 Hz, 1H), 4.55 (d, J = 5.2 Hz, 2H), 3.72 (s, 3H), 2.45 (s, 3H). | 460.0 |
| 24 | E2<br>J8 | 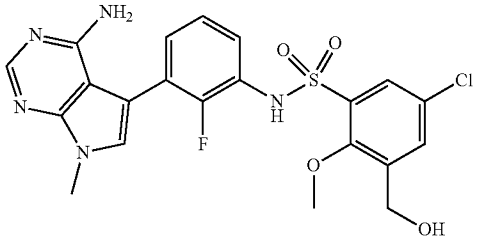 [SMILES: COc1c(CO)cc(Cl)cc1S(=O)(=O)Nc1cccc(-c2cn(C)c3ncnc(N)c23)c1F] | M & N | 54 | 10.24 (s, 1H), 8.14 (s, 1H), 7.69 (br s, 1H), 7.63 (d, J = 2.4 Hz, 1H), 7.26 (s, 1H), 7.10-7.24 (m, 3H), 5.99 (br s, 2H), 5.51 (t, J = 5.6 Hz, 1H), 4.57 (d, J = 5.6 Hz, 2H), 3.79 (s, 3H), 3.73 (s, 3H). | 492.1 |

TABLE K-continued

| Ex. No | SM | Product | Method | Yield (%) | $^1$H NMR (400 or 500 MHz, DMSO-$d_6$): δ | MS (m/z: M + H$^+$) |
|---|---|---|---|---|---|---|
| 25 | E2<br>J13 | 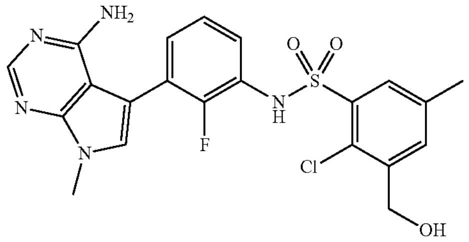 [SMILES: Cc1cc(CO)c(Cl)c(S(=O)(=O)Nc2cccc(-c3cn(C)c4ncnc(N)c34)c2F)c1] | M & N | 78 | 10.40 (s, 1H), 8.14 (s, 1H), 7.71 (br s, 1H), 7.60 ( br s, 1H), 7.26 (s, 1H), 7.18 (br m, 3H), 5.96 (br s, 2H), 5.54 (t, J = 5.6 Hz, 1H), 4.58 (d, J = 5.6 Hz, 2H), 3.72 (s, 3H), 2.34 (s, 3H) | 476.2 |
| 26 | E2<br>J10 | 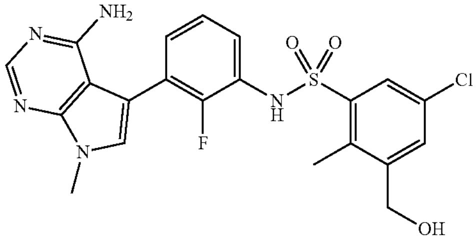 [SMILES: Cc1c(CO)cc(Cl)cc1S(=O)(=O)Nc1cccc(-c2cn(C)c3ncnc(N)c23)c1F] | M & N | 36 | 10.52 (br s, 1H), 8.14 (s, 1H), 7.72 (d, J = 2.4 Hz, 1H), 7.68 (br d, J = 2.0 Hz, 1H), 7.25 (s, 1H), 7.19 (br m, 3H), 5.97 (br s, 2H), 5.48 (t, J = 4.8 Hz, 1H), 4.56 (d, J = 5.2 Hz, 2H), 3.72 (s, 3H). 3Hs are under solvents | 476.3 |
| 27 | E10<br>J3 | 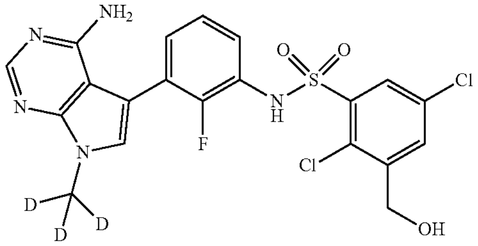 [SMILES: [2H]C([2H])([2H])n1cc(-c2cccc(NS(=O)(=O)c3cc(Cl)cc(CO)c3Cl)c2F)c2c(N)ncnc21] | M & N | 19 | 10.68 (s, 1H), 8.15 (s, 1H), 7.86 (d, J = 2.6 Hz, 1H), 7.75 (d, J = 2.8 Hz, 1H), 7.27 (s, 1H), 7.12-7.21 (m, 3H), 5.99 (s, 2H), 5.71 (t, J = 5.8 Hz, 1H), 4.61 (d, J = 5.5 Hz, 2H). | 499.0 |
| 28 | A1E11 and then I1 | 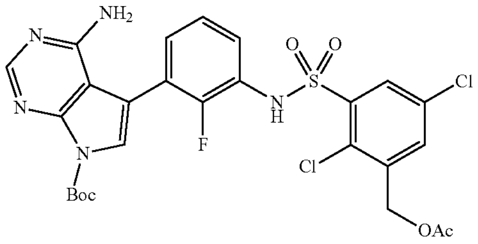 [SMILES: CC(=O)OCc1cc(Cl)cc(S(=O)(=O)Nc2cccc(-c3cn(C(=O)OC(C)(C)C)c4ncnc(N)c34)c2F)c1Cl] | M & K | crude | No Data | 623.9 |
| 29 | 2 | 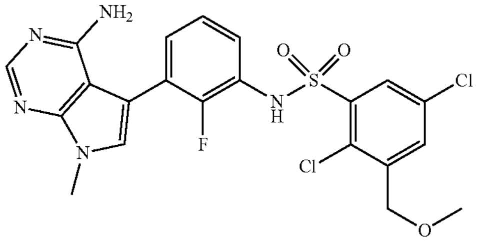 [SMILES: COCc1cc(Cl)cc(S(=O)(=O)Nc2cccc(-c3cn(C)c4ncnc(N)c34)c2F)c1Cl] | $POCl_3$<br>NaOMe | 45 | 10.72 (br s, 1H), 8.15 (s, 1H), 7.88 (d, J = 2.8 Hz, 1H), 7.75 (d, J = 2.4 Hz, 1H), 7.27 (s, 1H), 7.20 (m, 3H), 6.00 (br s, 2H), 4.55 (s, 2H), 3.73 (s, 3H), 3.38 (s, 3H). | 510.0 |
| 30 | E2<br>J15 | 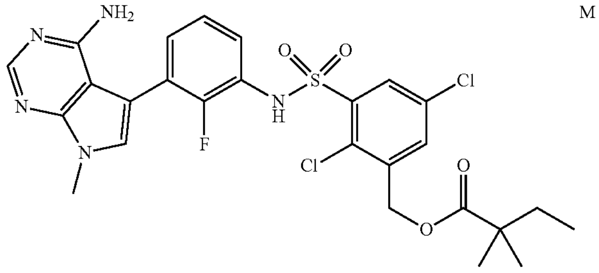 | M | 26 | 10.74 (br s, 1H), 8.14 (s, 1H), 7.93 (d, J = 2.4 Hz, 1H), 7.82 (s, 1H), 7.25 (s, 1H), 7.19 (m, 3H), 5.99 (br s, 2H), 5.19 (s, 2H), 3.72 (s, 3H), 1.45 (q, J = 7.6 Hz, 2H), 1.06 (s, 6H), 0.70 (t, J = 7.6 Hz, 3H). | 594.1 |

TABLE K-continued

| Ex. No | SM | Product | Method | Yield (%) | $^1$H NMR (400 or 500 MHz, DMSO-$d_6$): δ | MS (m/z: M + $H^+$) |
|---|---|---|---|---|---|---|
| 31 | E13 J3 | 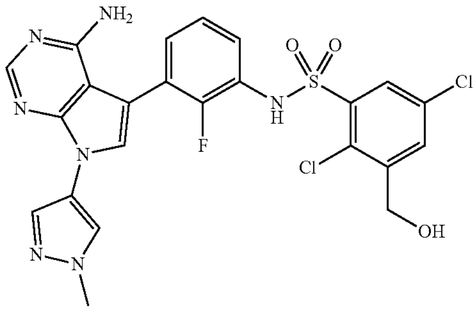 [SMILES: Cn1cc(-n2cc(-c3cccc(NS(=O)(=O)c4cc(Cl)cc(CO)c4Cl)c3F)c3c(N)ncnc32)cn1] | M & N | 26 | 10.74 (s, 1H), 8.38 (s, 1H), 8.22 (s, 1H), 7.99 (s, 1H), 7.87 (d, J = 2.4 Hz, 1H), 7.77 (br s, 1H), 7.64 (s, 1H), 7.22 (br m, 3H), 6.12 (br s, 2H), 5.72 (t, J = 5.2 Hz, 1H), 4.60 (d, J = 5.6 Hz, 2H), 3.91 (s, 3H). | 562.2 |
| 32 | E14 J3 | 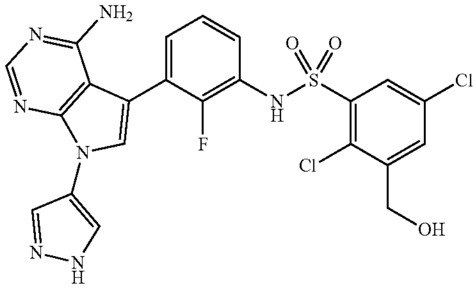 [SMILES: Nc1ncnc2c1c(-c1cccc(NS(=O)(=O)c3cc(Cl)cc(CO)c3Cl)c1F)cn2-c1cn[nH]c1] | M & N | 8 | 13.06 (br s, 1H), 10.74 (br s, 1H), 8.35 (br m, 1H), 8.22 (s, 1H), 8.09 (br m, 1H), 7.87 (d, J = 2.4 Hz, 1H), 7.76 (br s, 1H), 7.65 (s, 1H), 7.22 (br m, 3H), 6.11 (br s, 2H), 5.71 (t, J = 5.6 Hz, 1H), 4.60 (d, J = 5.6 Hz, 2H). | 548.1 |
| 33 | E2 J16 | 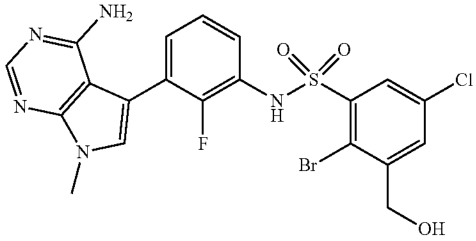 | M & N | 12 | 10.65 (br s, 1H), 8.15 (s, 1H), 7.88 (d, J = 2.4 Hz, 1H), 7.74 (d, J = 2.4 Hz, 1H), 7.28 (s, 1H), 7.17-7.22 (m, 3H), 6.01 (br s, 2H), 5.77 (t, J = 5.6 Hz, 1H), 4.56 (d, J = 5.6 Hz, 2H), 3.73 (s, 3H). | 540.2 |

Example 30. Biochemical Assay for GCN2

Activity of GCN2 kinase was determined using a TR-FRET kinase activity assay (e.g. Riddle et al. Analytical Biochemistry (2006) 356(1) 108-116). Assays were conducted in 384-well plates (13 µL assay volume) using 2 nM GCN2 (Carna Biosciences), 130 nM GFP-EIf2α (Invitrogen), 0.2 mg/mL *E. coli* tRNA (sigma) and 1 mM ATP in kinase buffer (Invitrogen). Inhibition of GCN2 was measured by adding serial diluted test compound (final assay concentration of 0.5% DMSO) followed by a 3-hour incubation. Tb-peIF2α (pSer52) antibody (Invitrogen) (2 nM final assay concentration) in kinase buffer containing EDTA (final assay concentration of 20 mM) was added. After a 60 min incubation at room temperature, TR-FRET was monitored using an excitation wavelength of 340 nm and emission wavelengths of 490 nm and 520 nm. The emission ratio (520/490) at each compound concentration of was converted to percent inhibition using controls (i.e., reaction with no test compound and reaction with a known inhibitor) and $IC_{50}$ values were calculated by fitting a four-parameter sigmoidal curve to the data using Prism (GraphPad software).

GCN2 protein sequence (residues 1-1649; G556E with a N-terminal GST tag)

SEQ ID NO: 1

MAPILGYWKIKGLVQPTRLLLEYLEEKYEEHLYERDEGDKWRNKKFELGL

EFPNLPYYIDGDVKLTQSMAIIRYIADKHNMLGGCPKERAEISMLEGAVL

DIRYGVSRIAYSKDFETLKVDFLSKLPEMLKMFEDRLCHKTYLNGDHVTH

PDFMLYDALDVVLYMDPMCLDAFPKLVCFKKRIEAIPQIDKYLKSSKYIA

WPLQGWQATFGGGDHPPKSDLEVLFQGPLGAMGSGIQRPTSTSSLVMAGG

RGAPGRGRDEPPESYPQRQDHELQALEAIYGADFQDLRPDACGPVKEPPE

INLVLYPQGLTGEEVYVKVDLRVKCPPTYPDVVPEIELKNAKGLSNESVN

LLKSRLEELAKKHCGEVMIFELAYHVQSFLSEHNKPPPKSFHEEMLERRA

QEEQQRLLEAKRKEEQEQREILHEIQRRKEEIKEEKKRKEMAKQERLEIA

SLSNQDHTSKKDPGGHRTAAILHGGSPDFVGNGKHRANSSGRSRRERQYS

VCNSEDSPGSCEILYFNMGSPDQLMVHKGKCIGDEQLGKLVYNALETATG

GFVLLYEWVLQWQKKMGPFLTSQEKEKIDKCKKQIQGTETEFNSLVKLSH

PNVVRYLAMNLKEQDDSIVVDILVEHISGVSLAAHLSHSGPIPVHQLRRY

TAQLLSGLDYLHSNSVVHKVLSASNVLVDAEGTVKITDYSISKRLADICK

-continued

EDVFEQTRVRFSDNALPYKTGKKGDVWRLGLLLLSLSQGQECGEYPVTIP

SDLPADFQDFLKKCVCLDDKERWSPQQLLKHSFINPQPKMPLVEQSPEDS

GGQDYVETVIPSNRLPSAAFFSETQRQFSRYFIEFEELQLLGKGAFGAVI

KVQNKLDGCCYAVKRIPINPASRQFRRIKGEVTLLSRLHHENIVRYYNAW

IERHERPAGPGTPPPDSGPLAKDDRAARGQPASDTDGLDSVEAAAPPPIL

SSSVEWSTSGERSASARFPATGPGSSDDEDDDEDEHGGVFSQSFLPASDS

ESDIIFDNEDENSKSQNQDEDCNEKNGCHESEPSVTTEAVHYLYIQMEYC

EKSTLRDTIDQGLYRDTVRLWRLFREILDGLAYIHEKGMIHRDLKPVNIF

LDSDDHVKIGDFGLATDHLAFSADSKQDDQTGDLIKSDPSGHLTGMVGTA

LYVSPEVQGSTKSAYNQKVDLFSLGIIFFEMSYHPMVTASERIFVLNQLR

DPTSPKFPEDFDDGEHAKQKSVISWLLNHDPAKRPTATELLKSELLPPPQ

MEESELHEVLHHTLTNVDGKAYRTMMAQIFSQRISPAIDYTYDSDILKGN

FSIRTAKMQQHVCETIIRIFKRHGAVQLCTPLLLPRNRQIYEHNEAALFM

DHSGMLVMLPFDLRIPFARYVARNNILNLKRYCIERVFRPRKLDRFHPKE

LLECAFDIVTSTTNSFLPTAEIIYTIYEIIQEFPALQERNYSIYLNHTML

LKAILLHCGIPEDKLSQVYIILYDAVTEKLTRREVEAKFCNLSLSSNSLC

RLYKFIEQKGDLQDLMPTINSLIKQKTGIAQLVKYGLKDLEEVVGLLKKL

GIKLQVLINLGLVYKVQQHNGIIFQFVAFIKRRQRAVPEILAAGGRYDLL

IPQFRGPQALGPVPTAIGVSIAIDKISAAVLNMEESVTISSCDLLVVSVG

QMSMSRAINLTQKLWTAGITAEIMYDWSQSQEELQEYCRHHEITYVALVS

DKEGSHVKVKSFEKERQTEKRVLETELVDHVLQKLRTKVTDERNGREASD

NLAVQNLKGSFSNASGLFEIHGATVVPIVSVLAPEKLSASTRRRYETQVQ

TRLQTSLANLHQKSSEIEILAVDLPKETILQFLSLEWDADEQAFNTTVKQ

LLSRLPKQRYLKLVCDEIYNIKVEKKVSVLFLYSYRDDYYRILF

Example 31. Biochemical Assay for PERK

Activity of PERK kinase was determined spectroscopically using a coupled pyruvate kinase/lactate dehydrogenase assay that continuously monitors the ATP hydrolysis-dependent oxidation of NADH (e.g., Schindler et al. Science (2000) 289: 1938-1942). Assays were conducted in 384-well plates (100 μt final volume) using 10 nM PERK (from Beryllium), 0.25 mg/mL Myelin Basic Protein substrate, 1.5 units pyruvate kinase, 2.1 units lactate dehydrogenase, 1 mM phosphoenol pyruvate, 0.28 mM NADH and 1 mM ATP in assay buffer (100 mM Tris, pH 7.5, 15 mM $MgCl_2$, 0.5 mM DTT, 0.004% (w/v) BSA, and 0.004% Triton X-100). Inhibition of PERK was measured by adding serial diluted test compound (final assay concentration of 1% DMSO). A decrease in absorption at 340 nm was monitored continuously for 6 hours at 30° C. on a multi-mode microplate reader (BioTek). The reaction rate was calculated using the 2-3 h time frame. The reaction rate at each concentration of compound was converted to percent inhibition using controls (i.e., reaction with no test compound and reaction with a known inhibitor) and $IC_{50}$ values were calculated using software routines in Prism (GraphPad software).

PERK protein sequence (residues 563-1115;
Sequence ID: NM 004836)

SEQ ID NO: 2

MSPILGYWKIKGLVQPTRLLLEYLEEKYEEHLYERDEGDKWRNKKFELGL

EFPNLPYYIDGDVKLTQSMAIIRYIADKHNMLGGCPKERAEISMLEGAVL

DIRYGVSRIAYSKDFETLKVDFLSKLPEMLKMFEDRLCHKTYLNGDHVTH

PDFMLYDALDVVLYMDPMCLDAFPKLVCFKKRIEAIPQIDKYLKSSKYIA

WPLQGWQATFGGGDHPPKSDLVPRGSKYDSVSGEANDSSWNDIKNSGYIS

RYLTDFEPIQCLGRGGFGVVFEAKNKVDDCNYAIKRIRLPNRELAREKVM

REVKALAKLEHPGIVRYFNAWLEAPPEKWQEKMDEIWLKDESTDWPLSSP

SPMDAPSVKIRRMDPFSTKEHIEIIAPSPQRSRSFSVGISCDQTSSSESQ

FSPLEFSGMDHEDISESVDAAYNLQDSCLTDCDVEDGTMDGNDEGHSFEL

CPSEASPYVRSRERTSSSIVFEDSGCDNASSKEEPKTNRLHIGNHCANKL

TAFKPTSSKSSSEATLSISPPRPTTLSLDLTKNTTEKLQPSSPKVYLYIQ

MQLCRKENLKDWMNGRCTIEERERSVCLHIFLQIAEAVEFLHSKGLMHRD

LKPSNIFFTMDDVVKVGDFGLVTAMDQDEEEQTVLTPMPAYARHTGQVGT

KLYMSPEQIHGNSYSHKVDIFSLGLILFELLYPFSTQMERVRTLTDVRNL

KFPPLFTQKYPCEYVMVQDMLSPSPMERPEAINIIENAVFEDLDFPGKTV

LRQRSRSLSSSGTKHSRQSNNSHSPLPSN

TABLE 1

Inhibition of biochemical activity of GCN2 and PERK kinases by exemplary compounds.

| Example No | GCN2 $IC_{50}$ (nM) | PERK $IC_{50}$ (nM) |
|---|---|---|
| 1 | ++++ | + |
| 2 | + | + |
| 3 | + | + |
| 4 | + | + |
| 5 | ++++ | + |
| 6 | ++ | + |
| 7 | ++ | + |
| 8 | + | + |
| 9 | ++++ | + |
| 10 | + | + |
| 11 | ++ | + |
| 12 | ++ | + |
| 13 | ++ | + |
| 14 | + | + |
| 15 | + | + |
| 16 | + | + |
| 17 | + | + |
| 18 | ++++ | + |
| 19 | ++ | + |
| 20 | ++ | + |
| 21 | + | + |
| 22 | ++ | + |
| 23 | ++ | + |
| 24 | ++++ | + |
| 25 | ++ | + |
| 26 | + | + |
| 27 | + | + |
| 29 | ++ | + |
| 30 | ++++ | ++++ |
| 31 | + | + |
| 32 | + | + |
| 33 | + | + |

For Table 1, "+" refers to an $IC_{50}$ less than or equal to 100 nM; "++" refers to an $IC_{50}$ greater than 100 nM and less than or equal to 500 nM; "+++" refers to an $IC_{50}$ greater than 500 nM and less than or equal to 1000 nM; and "++++" refers to an $IC_{50}$ greater than 1000 nM and less than or equal to 10000 nM.

In the below examples and figures. provided herein, "Compound 2" refers to the compound of Example 2 as described above.

Example 32. CCRF-CEM ASNase Cell Proliferation Assay, a Phenotypic Assay for Cellular Inhibition of GCN2

CCRF-CEM leukemia cells (catalog #CCL-116) were obtained from the American Type Culture Collect (ATTC, Manassas, VA). Cells were grown in RPMI-1640 medium supplemented with 10% heat-inactivated fetal bovine serum (Invitrogen, Carlsbad, CA) and 1% Penicillin/Streptomycin/L-Glutamine at 37° C., 5% $CO_2$, and 95% humidity. Cells were expanded until reaching one million cells per mL at which time they are subcultured or harvested for assay use. Ten thousand cells per well in 200 µL RPMI-1640 supplemented with 10% heat-inactivated fetal bovine serum and 1% Penicillin/Streptomycin were dispensed into a 96-well black clear bottom plate. A serial dilution of test compound and 1 mU/mL ASNase was added in triplicate and plates were incubated for 72 h at 37° C., 5% $CO_2$, and 95% humidity. At the end of the incubation, 40 µL of a 440 mM solution of resazurin (Sigma, St. Louis, MO) in PBS was added to each well of the plate and plates were incubated for an additional 6 h at 37° C., 5% $CO_2$, and 95% humidity. Plates were read on a Synergy2 or equivalent reader (Biotek, Winooski VT) using an excitation of 540 nm and an emission of 600 nm. Data was analyzed using GraphPad Prism software (GraphPad, San Diego, CA) to calculate $IC_{50}$ values.

Example 33. HCT116 Amino Acid Starved (-AA) Phospho-GCN2 and ATF4 Assay

HCT116 colorectal cancer cells (catalog #CCL-247) were obtained from the American Type Culture Collect (ATTC, Manassas, VA). Briefly, cells were grown in RPMI 1640 supplemented with 10% heat inactivated fetal bovine serum (Invitrogen, Carlsbad, CA) and 1% Penicillin/Streptomycin/L-Glutamine at 37° C., 5% $CO_2$, and 95% humidity. Cells were expanded until reaching 70-95% confluency at which point they were subcultured or harvested for assay use. Cells were seeded in 12-well culture plate at five hundred thousand cells per well in 1 mL complete growth medium and incubated overnight at 37° C., 5% $CO_2$, and 95% humidity. The next day each well was replaced with 1 mL Earle's Balanced Salt Solution (EBSS, Invitrogen, Carlsbad, CA) supplemented with 10% Dialyzed Fetal Bovine Serum, 5.5 mM Glucose, 1% Penicillin/Streptomycin and 1% Vitamin solution (thermo #11120052). A serial dilution of test compound was dispensed into well. Plates were incubated for 4 h at 37° C., 5% $CO_2$, and 95% humidity. At the end of the incubation, cells were washed with PBS supplemented with 1× Halt protease inhibitor, 1× Halt phosphatase inhibitor, 1× Sigma phosphatase inhibitor cocktail 2 and 1×EDTA and then lysed with M-PER Mammalian Protein Extraction Reagent supplemented with 3× of the inhibitor mix as described above. Cell lysates were sonicated with water bath sonicator (Qsonica, Newtown, CT) and supernatants were boiled with SDS buffer and reducing agent. Western blot was performed on each lysate to quantify phospho-GCN2 (Thr899), total GCN2, ATF4 and beta-Actin. Membranes were imaged with LI-COR Odyssey CLx Imaging System (LI-COR, Lincoln, NE). Data were analyzed using GraphPad Prism software (GraphPad, San Diego, CA) to calculate $IC_{50}$ values.

Example 34. CCRF-CEM TG ATF4 ELISA, a Phenotypic Assay for Cellular Inhibition of PERK Preactivated by Thapsigargin (TG)

CCRF-CEM leukemia cells (catalog #CCL-116) were obtained from the American Type Culture Collection (ATTC, Manassas, VA). Briefly, cells were grown in RPMI-1640 medium supplemented with 10% heat-inactivated fetal bovine serum (Invitrogen, Carlsbad, CA) and 1% Penicillin/Streptomycin/L-Glutamine at 37° C., 5% $CO_2$, and 95% humidity. Cells were expanded until reaching one million cells per mL at which time they were subcultured or harvested for assay use. One million five hundred thousand cells per well in 1 mL complete growth medium were dispensed into 12-well plates and incubated overnight. A serial dilution of test compound was added and cells were incubated at 37° C., 5% $CO_2$, and 95% for three hours, then 1 µM thapsigargin was added and cells were incubated for an additional hour at 37° C., 5% $CO_2$, and 95%. Cells were lysed then ATF4 levels were measured using an ELISA assay (Proteintech, Rosemont, IL). Absorbance was measured at 450 nM and 544 nM using a Synergy2 or equivalent reader (Biotek, Winooski VT). Data was analyzed using PRISM software (Graphpad, San Diego, CA) to calculate $IC_{50}$ values.

TABLE 2

Inhibition of proliferation of ASNase treated CCRF-CEM cells, Phospho-GCN2 and ATF4 in amino acid starved HCT116, and ATF4 in Thapsigargin stimulated CCRF-CEM cells by exemplary compounds.

| Example No | CCRF-CEM ASNase Cell Proliferation | HCT116 -AA pGCN2 Western Blot | HCT116 -AA ATF4 Western Blot | CCRF-CEM Thapsigargin ATF4 ELISA |
|---|---|---|---|---|
| 1 | ++ | | | ++ |
| 2 | + | + | + | + |
| 3 | + | + | + | + |
| 4 | + | | | + |
| 5 | ++++ | | | ++ |
| 6 | +++ | | | ++ |
| 7 | +++ | | | ++ |
| 8 | + | | | + |
| 9 | ++ | | | + |
| 10 | + | | | + |
| 11 | +++ | | | ++++ |
| 12 | ++++ | | | ++++ |
| 13 | ++ | | | ++ |
| 14 | ++ | | | ++ |
| 15 | ++ | | | +++ |
| 16 | +++ | | | ++ |
| 17 | + | | | + |
| 18 | ++++ | | | ++++ |
| 19 | ++ | | | + |
| 20 | ++ | | | ++ |
| 21 | ++ | | | ++ |
| 22 | ++++ | | | ++ |
| 23 | +++ | | | ++ |
| 24 | ++++ | | | ++ |
| 25 | ++ | | | + |
| 26 | ++ | | | + |
| 27 | + | | | + |
| 29 | ++++ | | | ++ |
| 30 | ++++ | | | +++ |
| 31 | + | | | + |
| 32 | + | | | ++ |
| 33 | + | | | + |

For Table 2, "+" refers to an $IC_{50}$ less than or equal to 100 nM; "++" refers to an $IC_{50}$ greater than 100 nM and less than or equal to 500 nM; "+++" refers to an $IC_{50}$ greater than 500 nM and less than or equal to 1000 nM; and "++++" refers to an $IC_{50}$ greater than 1000 nM and less than or equal to 10000 nM.

Example 35. H929 ATF4 ELISA ASSAY

H929 multiple myeloma cells (catalog #CRL-9068) were obtained from the American Type Culture Collection (ATTC, Manassas, VA). Briefly, cells were grown in RPMI-1640 medium supplemented with 20% heat-inactivated fetal bovine serum (catalog #A3840002, ThermoFisher Scientific, Waltham, MA), 1% Penicillin/Streptomycin/L-Glutamine (catalog #10378016, ThermoFisher Scientific, Waltham, MA), and 0.05 mM 2-mercaptoethanol (catalog #21985-023, ThermoFisher Scientific, Waltham, MA) at 37° C., 5% $CO_2$, and 95% humidity. Cells were expanded until reaching one million five hundred thousand cells per mL at which time they were sub-cultured or harvested for assay use. One million five hundred thousand cells per well in 1 mL complete growth medium were dispensed into 12-well plates and incubated overnight. A serial dilution of test compound was added, and cells were incubated at 37° C., 5% $CO_2$, and 95% for four hours. Cells were lysed then ATF4 levels were measured using an ELISA assay (Proteintech, Rosemont, IL). Absorbance is measured at 450 nM and 544 nM using a Synergy2 or equivalent reader (Biotek, Winooski VT). Data were analyzed using PRISM software (Graphpad, San Diego, CA) to calculate fold stimulation of cellular ATF4 relative to vehicle treated control.

TABLE 3

Stimulation of ATF4 in H929 Multiple Myeloma cells by exemplary compounds.

| Example No | H929 NS ATF4 ELISA |
|---|---|
| 1 | ++++ |
| 2 | +++ |
| 3 | ++++ |
| 4 | +++ |
| 5 | ++ |
| 8 | +++ |
| 9 | ++++ |
| 10 | +++ |
| 14 | ++ |
| 17 | +++ |
| 21 | ++ |
| 24 | ++ |
| 25 | +++ |
| 26 | +++ |

For Table 3, "+" refers to an ATF4 stim less than or equal to 5-fold; "++" refers to an ATF4 stim greater than 5-fold and less than or equal to 10 fold; "+++" refers to an ATF4 stim greater than 10 fold and less than or equal to 20 fold.

FIG. 1 is a graphical representation demonstrating the unexpected stimulation of the UPR/ISR marker ATF4 (black bars) in response to increasing concentrations of Compound 2. Stimulation occurred in a bell-shaped manner where ATF4 levels were found to peak at concentrations ranging from 4 to 123 nM, the concentration range where 50% or less of PERK molecules were occupied by Compound 2, followed by an inhibitory phase where ATF4 expression reverted to basal levels at concentrations more than or equivalent to 370 nM of Compound 2. The maximum stimulation in ATF4 signal was 13-fold and occurred around 41 nM of Compound 2.

Example 36. Detection of PERK Oligomerization Using NanoBRET

Constructs for BRET were built using the NanoBRET™ Flexi® PPI Starter System (Promega, Madison, WI). The full-length PERK ORF was obtained from Genscript (Piscataway, NJ). HEK-293 cells (catalog #CRL-1573) were obtained from the American Type Culture Collection (ATTC, Manassas, VA). Cells were grown in MEM medium supplemented with 10% heat-inactivated fetal bovine serum (Invitrogen, Carlsbad, CA) and 1% Penicillin/Streptomycin/L-Glutamine at 37° C., 5% $CO_2$, and 95% humidity. For BRET assays, cells were seeded at a density of 40,000 cells/mL in culture medium in 6-well plates and allowed to attach and recover. Cells were transfected with C-terminally tagged PERK-NLuc and C-terminally tagged PERK-Halo using Lipofectamine LTX (Thermo, Waltham, MA) and allowed to express proteins overnight at 37° C., 5% $CO_2$, and 95% humidity. Cells were then detached from culture dishes using 0.05% trypsin-EDTA, collected, and diluted in assay medium consisting of Opti-MEM® I Reduced Serum Medium supplemented with 4% FBS (Thermo) to 22,000 cells/mL. Cells were dispensed into 96-well cell culture plates and HaloTag® NanoBRET™ 618 Ligand (Promega) was added to a final concentration of 100 nM. Compound or DMSO was added to the cells, and plates were incubated for 4 h at 37° C., 5% $CO_2$, and 95% humidity. NanoBRET™ Nano-Glo® Substrate was added to the cells, and cells were shaken for 30 sec. Donor (460 nM) and acceptor (618) emissions were measured on a Synergy Neo2 Multi-Mode Reader (BioTek, Winooski, VT) within 10 min of substrate addition. Data was reported as BRET ratio (Acceptor/Donor).

Figure 2:
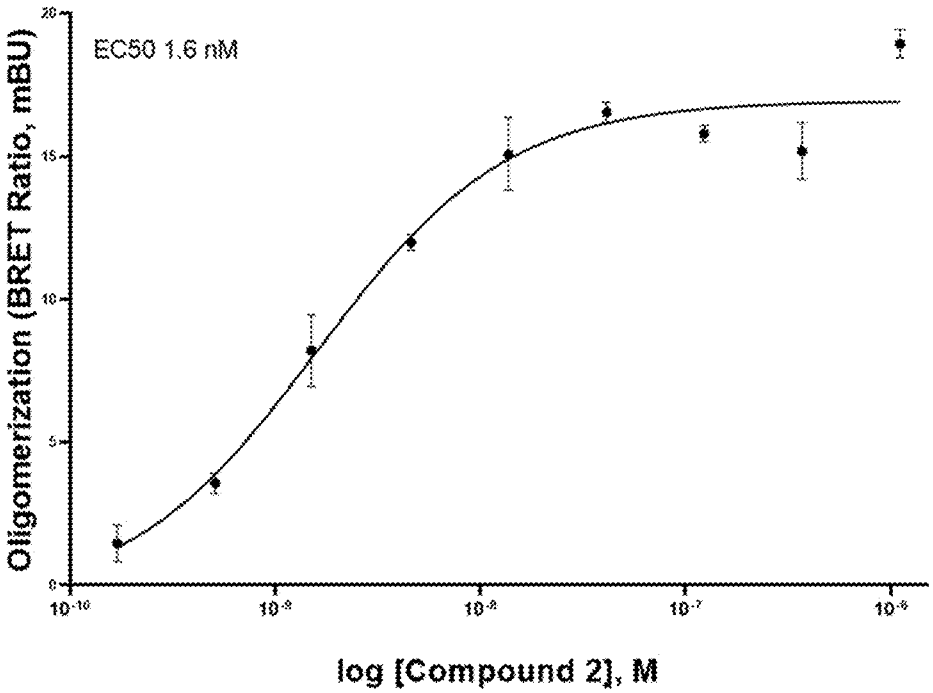
FIG. 2 shows a graph of the stimulation of PERK oligomers induced by Compound 2 in a NanoBRET assay.

Compound 2 unexpectedly exhibited stimulation of the formation of PERK oligomers, with an $EC_{50}$ of 1.6 nM. A graph of the stimulation PERK oligomers induced by Compound 2 is shown in FIG. 2.

Example 37. Stimulation of Multiple Myeloma UPR/ISR Signaling Pathway Proteins ATF4 and CHOP H929 multiple myeloma cells (catalog #CRL-9068) were obtained from the American Type Culture Collection (ATTC, Manassas, VA), grown in RPMI 1640 supplemented with 20% heat inactivated fetal bovine serum (Invitrogen, Carlsbad, CA), 1% Penicillin/Streptomycin/L-Glutamine and mM 2-mercaptoethanol at 37° C., 5% $CO_2$, and 95% humidity and maintained at 1-2 million cells per mL. Cells were seeded in 6 well plates at 4 million cells per well in 2 mL complete growth medium and treated with a serial dilution of test compounds for 4 h at 37° C., 5% $CO_2$, and 95% humidity. At the end of the incubation, cells are washed with PBS supplemented with 1× Halt protease inhibitor, 1× Halt phosphatase inhibitor, 1× Sigma phosphatase inhibitor cocktail 2 and 1×EDTA and then lysed with M-PER Mammalian Protein Extraction Reagent supplemented with 3× of the inhibitor mix as described above. Cell lysates were sonicated with water bath sonicator (Qsonica, Newtown, CT) and supernatants were boiled with SDS buffer and reducing agent. Western blot was performed to quantify ATF4, CHOP and beta-Actin (Cell Signaling Technology, Danvers, MA). Membranes were imaged with LI-COR Odyssey CLx Imaging System (LI-COR, Lincoln, NE).

Figure 3:
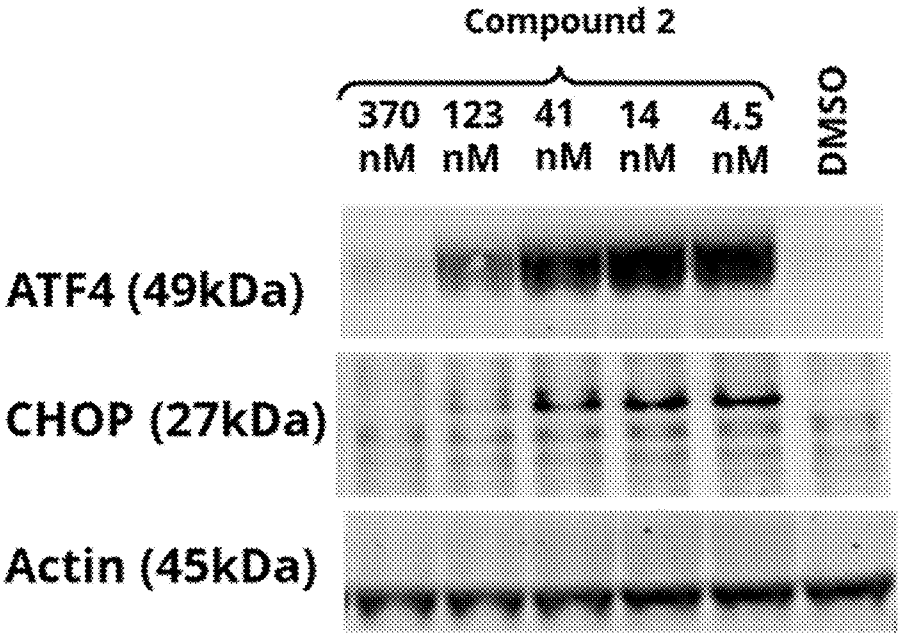
FIG. 3 shows stimulation of PERK downstream signaling proteins ATF4 and CHOP (Actin as a loading control) in H929 multiple myeloma cells.

Compound 2 unexpectedly exhibited stimulation of the UPR/ISR pathway in H929 multiple myeloma cells. A figure of the stimulation PERK downstream signaling proteins ATF4 and CHOP (Actin as a loading control) is shown in FIG. 3. ATF4 is stimulated across a concentration range of 4.5 nM to 123 nM. CHOP is stimulated across a concentration range of 4.5 nM to 41 nM.

Example 38. Stimulation of Multiple Myeloma UPR/ISR Target Genes Using Quantitative RT-PCR H929 multiple myeloma cells (catalog #CRL-9068) multiple myeloma cells were obtained from the American Type Culture Collection (ATTC, Manassas, VA). Cells were grown in RPMI-1640 medium supplemented with 20% heat-inactivated fetal bovine serum (catalog #A3840002, ThermoFisher Scientific, Waltham, MA), 1% Penicillin/Streptomycin/L-Glutamine (catalog #10378016, ThermoFisher Scientific, Waltham, MA), and 0.05 mM 2-mercaptoethanol (catalog #21985-023, ThermoFisher Scientific, Waltham, MA) at 37° C., 5% $CO_2$, and 95% humidity. Cells were expanded until reaching 70-95% confluency at which point they were subcultured or harvested for assay use. Cells were seeded in 6-well culture plate at $3.0\times10^6$ cells per well in 2 mL complete growth medium and incubated with indicated concentrations of Compound 2 at 37° C., 5% $CO_2$, and 95% humidity for 4 h. At the end of the incubation, cells were washed with PBS (Sigma) and RNA was extracted using RNeasy® Plus Kits (Qiagen, Germantown, MD). cDNA was synthesized using the High-Capacity cDNA Reverse Transcription Kit (Applied Biosciences, Beverly Hills, CA), and quantitative PCR was performed on a QuantStudio 3 (Applied Biosciences) using TaqMan Assays (Table 1, Thermo) and TaqMan Fast Advanced Master Mix (Thermo) according to manufacturer's specifications.

TABLE

TaqMan Probes

| Gene of Interest | Assay ID |
|---|---|
| ATF4 | Hs00909569_g1 |
| DDIT3 (CHOP) | Hs00358796_g1 |
| GPT2 | Hs00370287_m1 |
| GUSB (Endogenous Control) | Hs00939627_m1 |
| PPP1R15A (GADD34) | Hs00169585_m1 |
| VEGFA | Hs00900055_m1 |

Figure 4:
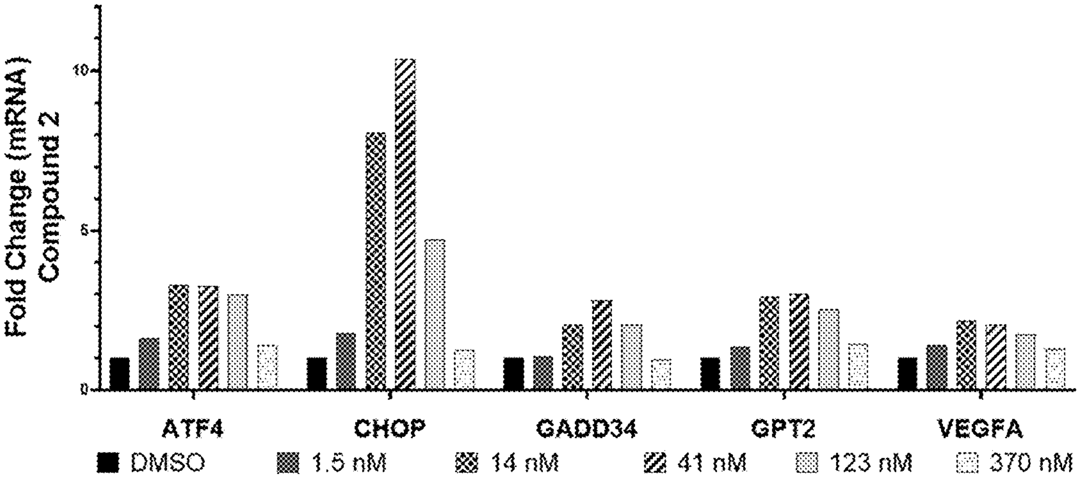
FIG. 4 is a graphical representation demonstrating the stimulation of ATF4 target genes in response to increasing concentrations of Compound 2 in H929 multiple myeloma cells.
Figure 5:
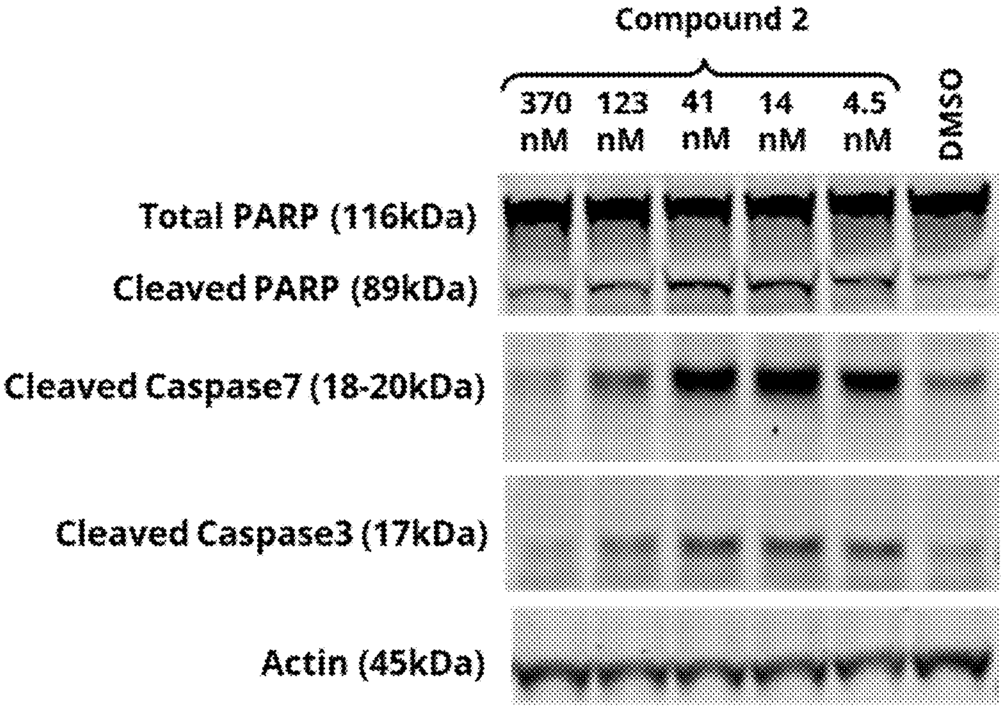
FIG. 5 illustrates effects of Compound 2 on apoptotic pathway readouts in H929 multiple myeloma cells.

Compound 2 unexpectedly induced the expression of UPR/ISR target genes in H929 multiple myeloma cells. Data reported as fold change over vehicle control (DMSO) treated sample. FIG. 4 is a graphical representation demonstrating the stimulation of ATF4 target genes in response to increasing concentrations of Compound 2 (DMSO black bars, 1.5 nM dark grey bars, 14 nM checkered bars, 41 nM striped bars, 123 nM light grey bars and 370 nM dotted bars). Transcriptional activation of ATF4 target genes occurred in a bell-shaped manner. The maximum stimulation for ATF4 at 4 h time points was ~3 folds; the maximum stimulation for CHOP at 4 h was ~10 folds; the maximum stimulation for GADD34 at 4 h was ~3 folds; the maximum stimulation for GPT2 at 4 h was ~3; the maximum stimulation for VEGFA at 4 h was ~2 folds. Stimulation of ATF4 target genes occurred in a bell-shaped manner where levels were found to peak at concentrations ranging from 14 to 123 nM, the concentration range where 50% or less of PERK molecules were occupied by Compound 2, followed an inhibitory phase where the expression reverted to basal levels at concentrations more than or equivalent to 370 nM of Compound 2.

Example 39. Stimulation of Multiple Myeloma Apoptosis Signaling Pathway

H929 multiple myeloma cells (catalog #CRL-9068) were obtained from the American Type Culture Collection (ATTC, Manassas, VA), grown in RPMI 1640 supplemented with 20% heat inactivated fetal bovine serum (Invitrogen, Carlsbad, CA), 1% Penicillin/Streptomycin/L-Glutamine and 0.05 mM 2-mercaptoethanol at 37° C., 5% $CO_2$, and 95% humidity and maintained at 1-2 million cells per mL. Cells were seeded in 6 well plates at 4 million cells per well in 2 mL complete growth medium and treated with a serial dilution of test compounds for 24 h at 37° C., 5% $CO_2$, and 95% humidity. At the end of the incubation, cells are washed with PBS supplemented with 1× Halt protease inhibitor, 1× Halt phosphatase inhibitor, 1× Sigma phosphatase inhibitor cocktail 2 and 1×EDTA and then lysed with M-PER Mammalian Protein Extraction Reagent supplemented with 3× of the inhibitor mix as described above. Cell lysates were sonicated with water bath sonicator (Qsonica, Newtown, CT) and supernatants were boiled with SDS buffer and reducing agent. Western blot was performed to quantify cleaved-Caspase 3, cleaved-Caspase 7, PARP, and beta-Actin (Cell Signaling Technology, Danvers, MA). Membranes were imaged with LI-COR Odyssey CLx Imaging System (LI-COR, Lincoln, NE).

Compound 2 unexpectedly induced the expression of proapoptotic proteins in H929 multiple myeloma cells. Treating the cells with Compound 2 resulted in an increase in the levels of cleaved PARP, cleaved Caspase-7 and cleaved Caspase-3. The stimulation of these apoptotic read-outs occurred in a bell-shaped manner and peaked at concentrations ranges from 4.5 nM to 41 nM.

Example 40. Inhibition of Multiple Myeloma and B-Cell Lymphoma Cell Proliferation H929, RPMI8226, GA-10 and DoHH-2 cells (catalog #CRL-9068) were obtained from the American Type Culture Collection (ATTC, Manassas, VA). H929 Cells were maintained in RPMI-1640 medium supplemented with 20% heat-inactivated fetal bovine serum (catalog #A3840002, ThermoFisher Scientific, Waltham, MA), 1% Penicillin/Streptomycin/L-Glutamine (catalog #10378016, ThermoFisher Scientific, Waltham, MA), and 0.05 mM 2-mercaptoethanol (catalog #21985-023, ThermoFisher Scientific, Waltham, MA). RPMI8226, GA-10, DoHH-2 were maintained in RPMI-1640 medium supplemented with 10% heat-inactivated fetal bovine serum (catalog #A3840002, ThermoFisher Scientific, Waltham, MA) and 1% Penicillin/Streptomycin/L-Glutamine (catalog #10378016, ThermoFisher Scientific, Waltham, MA). All cells were grown at 37° C., 5% $CO_2$, and 95% humidity. Cells were expanded until reaching one million five hundred thousand cells per mL at which time they were subcultured or harvested for assay use.

For cell proliferation assay appropriate number of cells (Forty thousand cells for H929. Twenty thousand cells for RPMI8226 and GA-10. Eight thousand cells for DoHH-2) were seeded per well in 200 μL in respective medium were dispensed into a 96-well black clear bottom plate. A serial dilution of test compound is added in triplicate and plates were incubated for 72 or 120 h at 37° C., 5% $CO_2$, and 95% humidity. Several standard of care agents were used for combination studies (Lenalidomide (catalog #S1029, Selleckchem, Houston, TX), Bortezomib (catalog #S1013, Selleckchem, Houston, TX), Dexamethasone (catalog #S1322, Selleckchem, Houston, TX), Ibrutinib (Pharmacyclics, Sunnyvale, CA)). At the end of the incubation for H929, RPMI8226 and GA-10, 40 μL of a 440 mM solution of resazurin (Sigma, St. Louis, MO) in PBS was added to each well of the plate and plates were incubated for an additional 7 h at 37° C., 5% $CO_2$, and 95% humidity. Plates were read on a Synergy2 or equivalent reader (Biotek, Winooski VT) using an excitation of 540 nm and an emission of 600 nm. At the end of the incubation of DoHH-2, cell viability was determined using CellTiter-Glo® assay (Promega, Madison, WI). Luminescence was measured using EnVision MultiLabel Reader (PerkinElmer, Waltham, MA). Data was analyzed using GraphPad Prism software (GraphPad, San Diego, CA) to calculate $IC_{50}$ values.

Figure 6A:
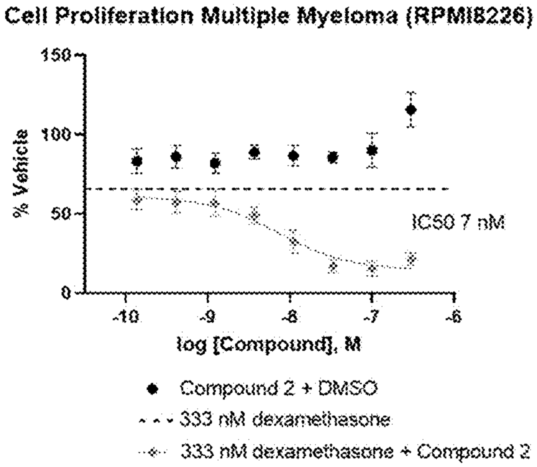
FIGS. 6A, 6B, 6C, and 6D depict cell proliferation studies of Compound 2 in combination with standard of care treatment in RPMI8226 Multiple Myeloma cells (FIG. 6A), H929 Multiple Myeloma cells (FIG. 6B), GA-10 Burkitt lymphoma cells (FIG. 6C), and Follicular lymphoma cells (FIG. 6D).
Figure 6B:
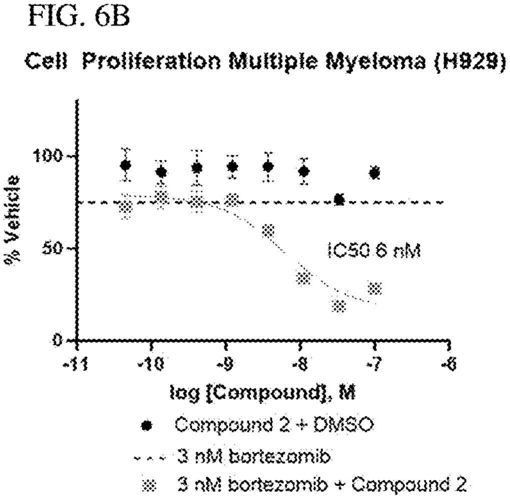
Figure 6C:
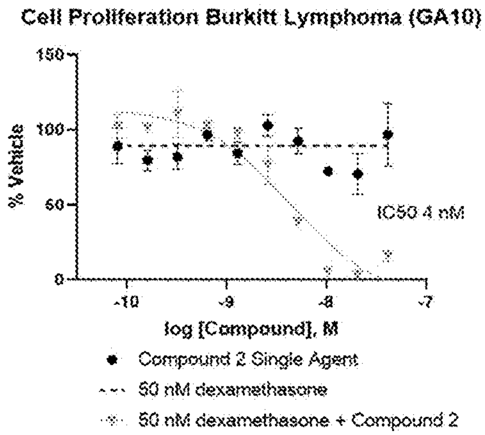
Figure 6D:
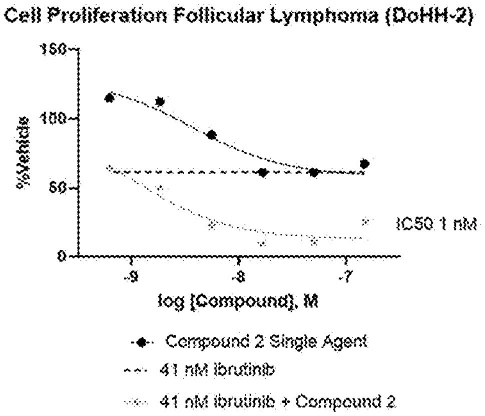

Compound 2, in combination with standard of care (SOC) agents that treat multiple myeloma or B cell lymphomas, exhibits additivity or synergy for inhibition of cell proliferation. Representative graphs are shown in FIGS. 6A, 6B, 6C, and 6D. FIG. 6A represents a cell proliferation experiment of RPMI8226 Multiple Myeloma cells treated with Compound 2 titer with (grey diamond) or without (black circles) 333 nM dexamethasone for 96 h. The combination treatment resulted in inhibition of cell proliferation with an IC50 of 7 nM. FIG. 6B represents a cell proliferation experiment of H929 Multiple Myeloma cells treated with Compound 2 titer with (grey squares) or without (black circles) 3 nM bortezomib for 96 h. The combination treatment resulted in inhibition of cell proliferation with an IC50 of 6 nM. FIG. 6C represents a cell proliferation experiment of GA-10 Burkitt lymphoma cells treated with Compound 2 titer with (grey triangle) or without (black circles) 50 nM dexamethasone for 96 h. The combination treatment resulted in inhibition of cell proliferation with an IC50 of 4 nM. FIG. 6D represents a cell proliferation experiment of Follicular lymphoma cells treated with Compound 2 titer with (grey stars) or without (black circles) 41 nM ibrutinib for 96 h. The combination treatment resulted in inhibition of cell proliferation with an $IC_{50}$ of 4 nM.

Example 41. CCRF-CEM Xenograft Pharmacokinetic/Pharmacodynamic (PK/PD) Model

The CCRF-CEM xenograft model was performed in compliance with all the laws, regulations and guidelines of the National Institutes of Health (NIH) and with the approval of the Animal Care and Use Committee of Labcorp (Ann Arbor, MI), an AAALAC accredited facility. Food and water was provided ad libitum. All mice were observed for clinical signs at least once daily. Female Envigo C.B-17 SCID (6-7 weeks old) were inoculated subcutaneously just below the right high axilla with ten million cells in Dulbecco's Phosphate Buffered Saline, using a 27-gauge needle and syringe. When tumor burdens reached 200 mm 3 on average on day 22, mice were randomly assigned into groups such that the mean tumor burden for all groups was within 10% of the overall mean tumor burden for the study population. Groups were treated on days 23-24 as follows: on day 23 vehicle control (dosed orally and IP to mimic combination groups) (n=9); ASNase (Abcam, Cambridge, UK) dosed IP at 1000 U/kg/day (n=9). On day 24 vehicle control (dosed orally and IP to mimic combination groups) (n=9); Compound 2 dosed orally at 50 mg/kg/day of Compound 2 (n=9) and ASNase (Abcam, Cambridge, UK) dosed IP at 1000 U/kg/day (n=9) 2 h prior to sample harvest; Compound 2 dosed orally at 25 mg/kg/day of Compound 2 (n=9) and ASNase (Abcam, Cambridge, UK) dosed IP at 1000 U/kg/day (n=9) 2 h prior to sample harvest at 2, 6 and 10 h post Compound 2 dose. Blood samples were collected in $K_2EDTA$ tubes and processed into plasma, snap frozen in liquid nitrogen then stored at −80° C. Plasma samples were subjected to pharmacokinetic analysis using liquid chromatography coupled with tandem mass spectrometry analysis (Cayman Chemical, Ann Arbor, MI). Tumors and pancreatic tissues were harvested and powdered over liquid nitrogen in covaris bags and stored at −80° C. Fr tissue sample processing roughly mg of tumor or pancreatic tissue was lysed in mPER lysis buffer (Thermo Fisher Scientific, Waltham, MA) supplemented with 3× Halt protease inhibitor, 3× Halt phosphatase inhibitor, 3× Sigma phosphatase inhibitor cocktail 2 and 3×EDTA on ice then homogenized using Bead Ruptor 96 (Omni, Kennesaw, GA). Samples were then centrifuged at 21,000 g for 10 min at 4° C. Cleared lysates were then transferred to ice-chilled conical bottom 96-well plates, sealed then stored at −80° C. Next day, samples were thawed on ice followed by centrifugation at 3739 g for 10 min at 4° C. Cleared lysates were then transferred to ice-chilled round bottom 96-well plates. Protein concentrations were determined using BCA protein assay kit (Thermo Fisher Scientific, Waltham, MA). Lysates were normalized to 10 μg/μL prior to boiling in 4×SDS-sample buffer and reducing agent. Samples were resolved using SDS-PAGE then analyzed using Western blot to quantify phospho-GCN2 (Thr899) (Abcam, Cambridge, UK), total GCN2, ATF4 and beta-Actin (Cell Signaling Technology, Danvers, MA). Membranes are imaged with LI-COR Odyssey CLx Imaging System (LI-COR, Lincoln, NE). Data is analyzed using GraphPad Prism software (GraphPad, San Diego, CA) to calculate % inhibition.

Figures 7A, 7B:
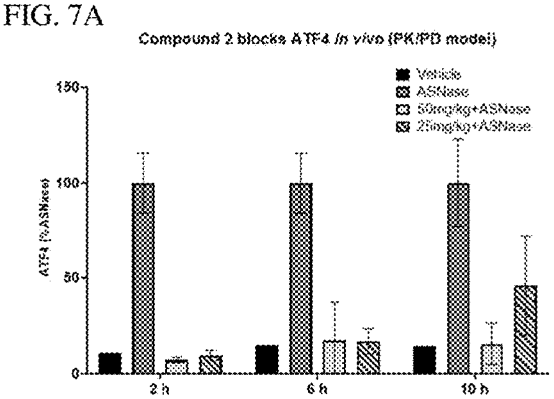
FIGS. 7A and 7B show effects of Compound 2 in combination with asparaginase on ATF4 levels, measuring GCN2 activity, in an in vivo PK/PD model.

Compound 2, in combination with ASNase, inhibits GCN2-mediated ATF4 levels in a CCRF-CEM leukemia xenograft model. As shown in FIG. 7, Compound 2 inhibited ATF4 levels by 87 to 91% compared to vehicle control when dosed at 50 mg/kg orally, and inhibited ATF4 levels by 57% to 93% compared to vehicle control when dosed at 25 mg/kg orally. Corresponding plasma levels of Compound 2 were determined at the PD time points of 2, 6, and 10 hours post dose.

Example 42. MV-4-11 Xenograft Efficacy Model

The MV-4-11 xenograft model was performed in compliance with all the laws, regulations and guidelines of the National Institutes of Health (NIH) and with the approval of the Animal Care and Use Committee of Crown Bioscience (Taicang, China), an AAALAC accredited facility. Food and water was provided ad libitum. All mice were observed for clinical signs at least once daily. Female NOD/SCID (6-9 weeks old; Vital River Laboratories Research Models and Services (Beijing, China)) were inoculated subcutaneously right front flank region with five million cells in Dulbecco's Phosphate Buffered Saline:Matrigel (1:1), using a 27-gauge needle and syringe. When tumor burdens reached 150 mm 3 on average on day 7, mice were randomly assigned into groups such that the mean tumor burden for all groups was within 10% of the overall mean tumor burden for the study population. Groups were treated on days 7-21 as follows: vehicle control (dosed orally and IP to mimic combination groups) (n=10); Compound 2 dosed orally at 50 mg/kg/day of Compound 2 (n=10); Leunase (Kyowa Kirin, Japan) dosed IP at 1000 U/kg/day (n=10); Leunase (Kyowa Kirin, Japan) dosed IP at 1000 U/kg/day (n=10) and Compound 2 dosed orally at 50 mg/kg/day of Compound 2 (n=10). Tumor volume and body weight were measured three time per week. Tumor burden (mg) was estimated from caliper measurements by the formula: tumor burden (mg=mm 3)=(length×width 2)/2.

Figure 8:
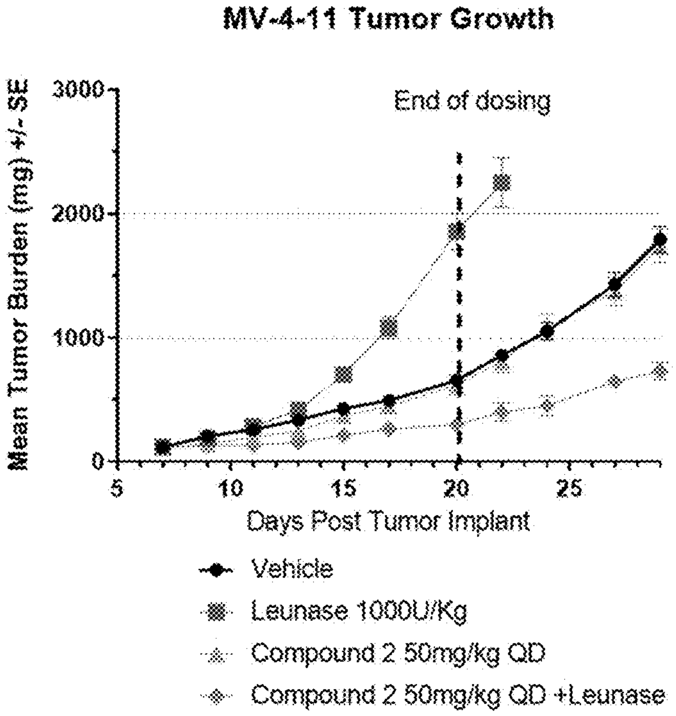
FIG. 8 depicts a plot showing the effect of Compound 2 in combination with asparaginase on tumor growth in an MV-4-11 xenograft model.

Compound 2, in combination with ASNase, inhibits MV-4-11 tumor growth when dosed orally. As shown in FIG. 8, no significant effect on tumor growth was observed after 14 days of dosing with 50 mg/kg/day of Compound 2 as a single agent. At 50 mg/kg/day of Compound 2 combined with Leunase the mean tumor growth inhibition was 54% after 14 days of dosing.

Example 43. Recombinant GCN2 Activation Assay

Recombinant GCN2 (EIF2AK4) (Carna Biosciences, Japan) was dephosphorylated by incubating with 16,000 units of lambda phosphatase (New England Biolabs, Ipswich, MA) for 3 h at 30° C. in 1× phosphatase reaction buffer. To measure Compound 2-mediated GCN2 modulation, 12.5 nM dephosphorylated GCN2 diluted in Kinase buffer (Invitrogen, Carlsbad, CA) was incubated with Compound 2 titer for 30 min at RT. Following incubation, 130 nM substrate (GFP-eIF2α) (ThermoFisher Scientific, Waltham, MA) and 0.05 mM ATP was added to the mixture and incubated for 60 min at RT. Reaction was stopped by the addition of 10 mM EDTA and phosphorylated eiF2a substrate was detected using 2 nM LanthaScreen Tb-anti-peIF2α (pSer52) antibody (ThermoFisher Scientific, Waltham, MA) then incubated in the dark. After a 60 min incubation at room temperature, TR-FRET was monitored using an excitation wavelength of 340 nm and emission wavelengths of 490 nm and 520 nm.

Figure 9A:
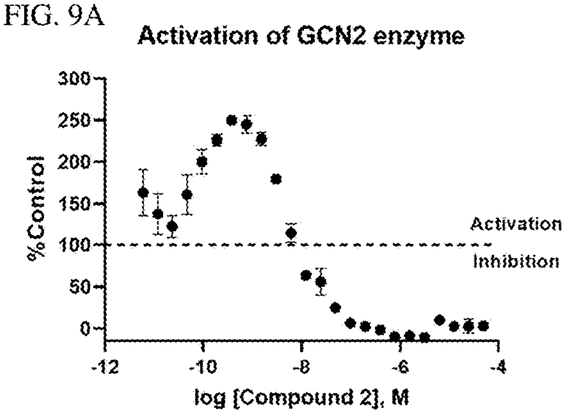
FIG. 9A shows effects of Compound 2 in a recombinant GCN2 activation assay, measuring the activity of recombinant GCN2 enzyme in vitro.

In FIG. 9A, at concentrations ranging from 0.05-3 nM Compound 2 unexpectedly activated GCN2 enzyme up to 250% of control. At concentrations above 10 nM, Compound 2 inhibited the activity of recombinant GCN2 enzyme in vitro.

Example 44. Recombinant PERK Activation Assay

To measure Compound 2-mediated PERK modulation, 200 nM PERK enzyme (Enzo, Farmingdale, NY) was incubated with Compound 2 titer for 30 min at RT. Following incubation, 200 nM substrate (GFP-eIF2α) (ThermoFisher Scientific, Waltham, MA) and 1 mM ATP was added to the mixture and incubated for 60 min at RT. Reaction was stopped by the addition of 10 mM EDTA and phosphorylated eiF2a substrate was detected using 2 nM LanthaScreen Tb-anti-peIF2α (pSer52) antibody (ThermoFisher Scientific, Waltham, MA) then incubated in the dark. After a 60 min incubation at room temperature, TR-FRET was monitored using an excitation wavelength of 340 nm and emission wavelengths of 490 nm and 520 nm.

Figure 9B:
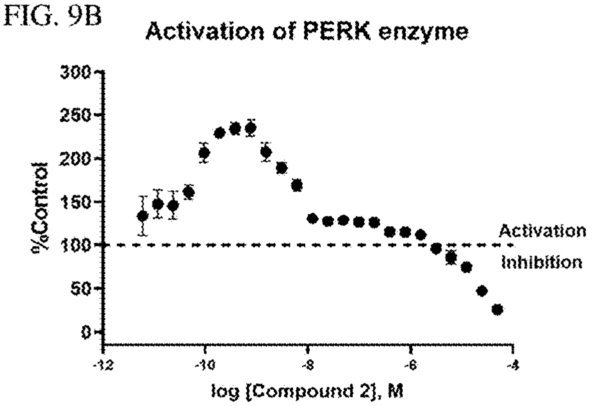
FIG. 9B illustrates effects of Compound 2 in recombinant PERK activation assay, measuring the activity of recombinant PERK enzyme in vitro.

In FIG. 9B, at concentrations ranging from 0.05-6 nM Compound 2 unexpectedly activated PERK enzyme up to 250% of control. At concentrations above 3 μM, Compound 2 inhibited the activity of recombinant PERK enzyme in vitro.

Example 45. Spheroid Western Blot Assay

NSCLC cell lines H358 (catalog #CRL-5807) and H2030 (catalog #CRL-5914), and fibrosarcoma cell line HT-1080 (catalog #CRL-5807) were obtained from the American Type Culture Collect (ATTC, Manassas, VA). Cells were grown in RPMI-1640 medium supplemented with 10% heat-inactivated fetal bovine serum and 1% Penicillin/Streptomycin/L-Glutamine (Invitrogen, Carlsbad, CA) at 37° C., 5% $CO_2$, and 95% humidity and maintained at 50-80% confluency until use. Cells were plated at 500,000 cells/well in 24-well Elplasia plates (Corning, Glendale, AZ) with complete growth media at 1 mL/well and incubated overnight at 37° C., 5% $CO_2$, and 95% humidity to form spheroids. The next day, serial dilutions of test compounds were prepared in complete growth media and 500 μL existing media was removed from each well and replaced with fresh media containing compound titers. Spheroids were then incubated with test compounds for 4 hours or 24 hours under the same conditions. At the end of the incubation, spheroids were washed with PBS supplemented with 1× Halt protease inhibitor, 1× Halt phosphatase inhibitor (Invitrogen, Carlsbad, CA), 1× Sigma phosphatase inhibitor cocktail 2 (Sigma, St. Louis, MO) and 1×EDTA (Invitrogen, Carlsbad, CA) and then lysed with M-PER Mammalian Protein Extraction Reagent (Invitrogen, Carlsbad, CA) supplemented with 3× of the inhibitor mix as described above. Cell lysates were sonicated with a water bath sonicator (Qsonica, Newtown, CT) and supernatants were boiled with SDS buffer and reducing agent. Western blots were performed to quantify phospho-GCN2 (R&D Systems, Minneapolis, MN), ATF4, CHOP, cleaved PARP, cleaved Caspase 3 and 7, and beta-Actin (Cell Signaling Technology, Danvers, MA). Membranes were imaged with LI-COR Odyssey CLx Imaging System (LI-COR, Lincoln, NE).

Figure 10A:
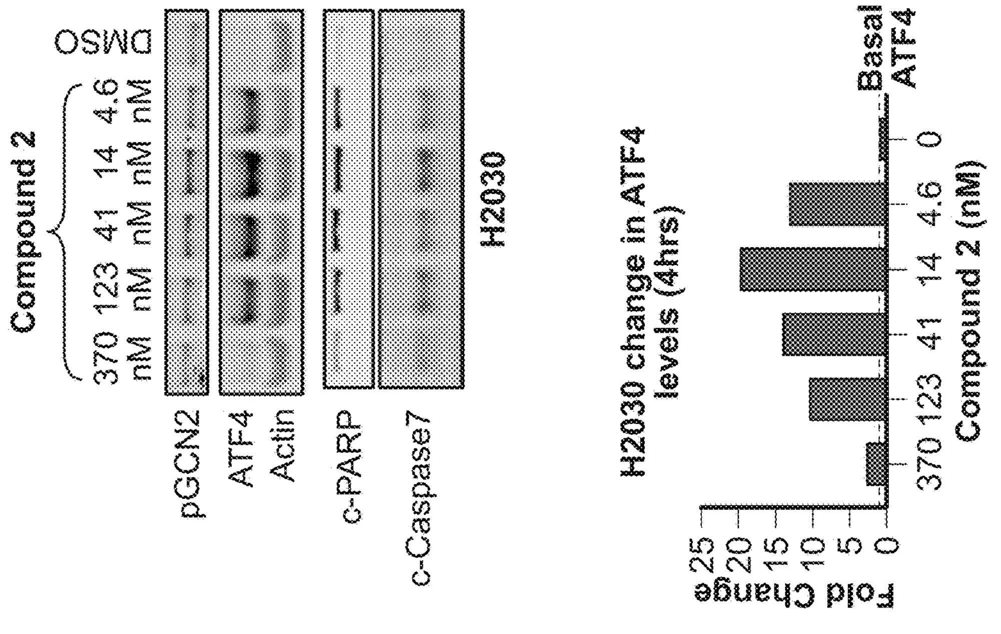
FIGS. 10A, 10B, and 10C show effects of Compound 2 on ISR and apoptosis pathways in solid tumor cancers (FIG. 10A, H2030.
Figure 10B:
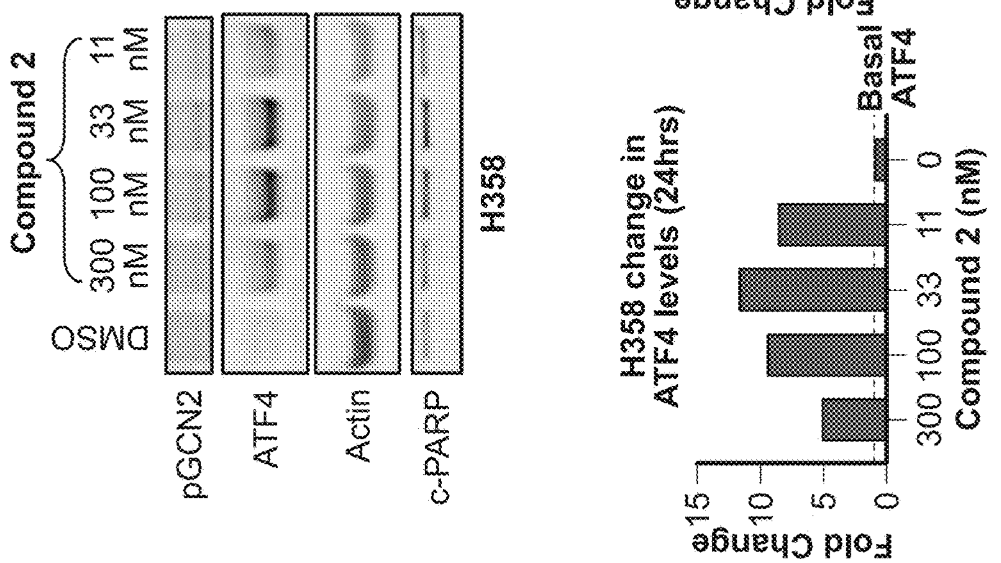
Figure 10C:
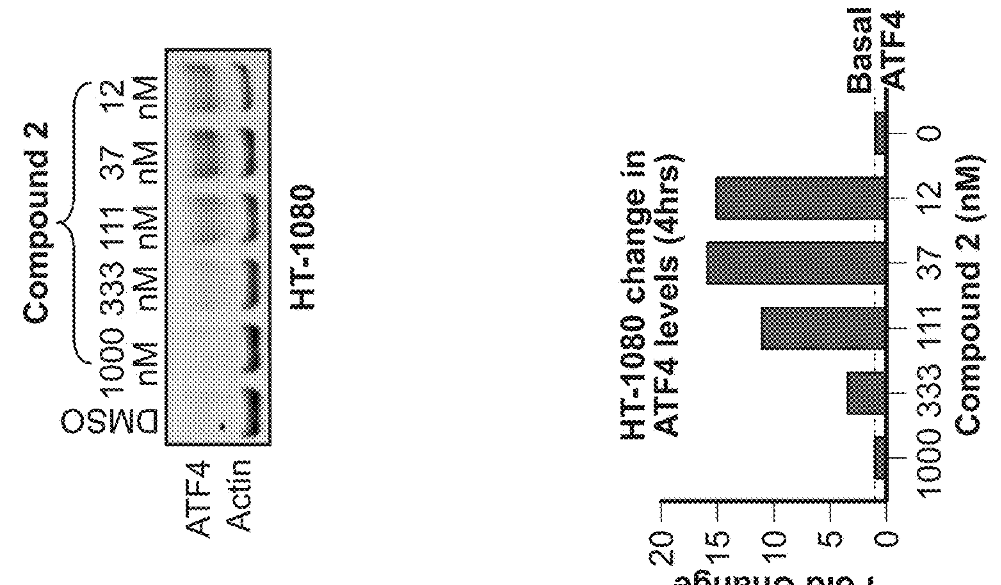

In FIGS. 10A, 10B, and 10C, Compound 2 unexpectedly exhibited stimulation of the ISR and the apoptosis pathways in solid tumor cancers (FIG. 10A, H2030; FIG. 10B, H358; FIG. 10C, HT-1080) cell lines. A Western blot image of the upregulated GCN2 phosphorylation (pGCN2) and downstream signaling protein ATF4 and pro-apoptosis pathway markers (cleaved-PARP1, cleaved-Caspase 3/7) (Actin as a loading control) is shown in FIGS. 10A, 10B, and 10C. Levels of pGCN2 were upregulated in H2030 and H358 cell lines, and ATF4, c-PARP and c-Caspase7 were upregulated across a concentration range of 4.6 nM and up to 300 nM. Western blot quantification of ATF4 signal is represented in the bar graph format. Compound 2 upregulated ATF4 up to 20-fold in the H2030 spheroid, 12-fold in the H358 spheroids and 15-fold in the HT-1080 spheroids.

Example 46. Spheroid Proliferation Assay

Non Small Cell Lung Cancer (NSCLC) cell lines H358 (catalog #CRL-5807) and H2030 (catalog #CRL-5914), and fibrosarcoma line HT-1080 (catalog #CRL-5807) were obtained from the American Type Culture Collect (ATTC, Manassas, VA). Cells were grown in RPMI-1640 medium supplemented with 10% heat-inactivated fetal bovine serum and 1% Penicillin/Streptomycin/L-Glutamine (Invitrogen, Carlsbad, CA) at 37° C., 5% $CO_2$, and 95% humidity and maintained at 50-80% confluency until use. 500-1000 cells were plated in 96-well ultra-low attachment plates (Corning, Glendale, AZ) with complete growth media at 80 μL/well and incubated overnight at 37° C., 5% $CO_2$, and 95% humidity to form spheroids. The next day, serial dilutions of test compounds were prepared in complete growth media and 20 μL/well media containing compound titers was added to spheroids in triplicate. Spheroids were then incubated with test compounds for 5 days under the same conditions. At the end of the incubation, spheroids were lysed with 100 μL/well CellTiter-Glo 3D Viability Assay (Promega, Madison, WI) and luminescence was detected using Synergy2 or equivalent reader (Biotek, Winooski, VT). Data was analyzed using GraphPad Prism software (GraphPad, San Diego, CA) to calculate $IC_{50}$ values.

Figure 11A:
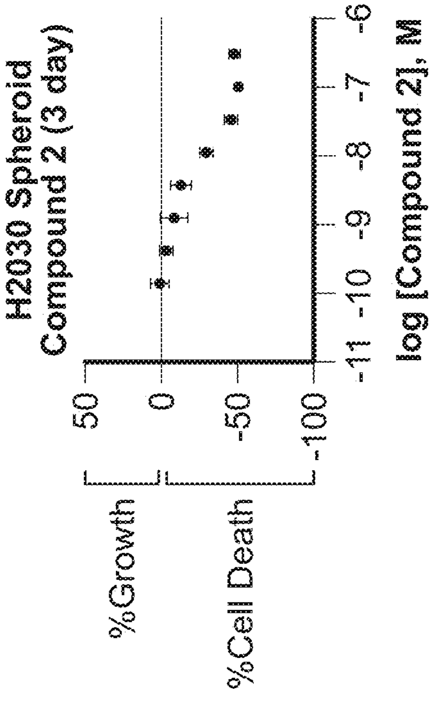
FIGS. 11A, 11B, and 11C show effects of Compound 2 in a spheroid proliferation assay.
Figure 11B:
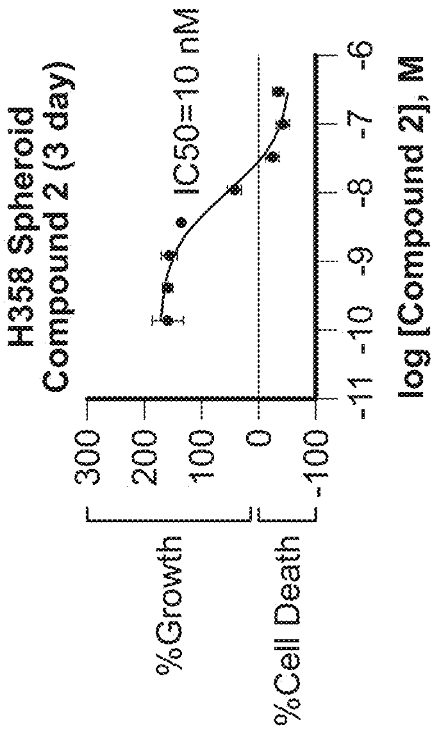
Figure 11C:
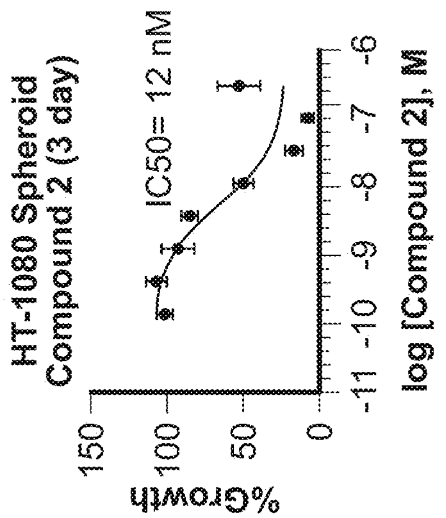

In FIGS. 11A, 11B, and 11C, Compound 2 induced 50% cell regression in the H2030 solid tumor spheroids as a single agent (FIG. 11A). Compound 2 inhibited the cell proliferation of the H358 ($IC_{50}$ 10 nM, FIG. 11B) and the HT-1080 ($IC_{50}$ 12 nM, FIG. 11C) solid tumor spheroids as a single agent.

Figure 12A:
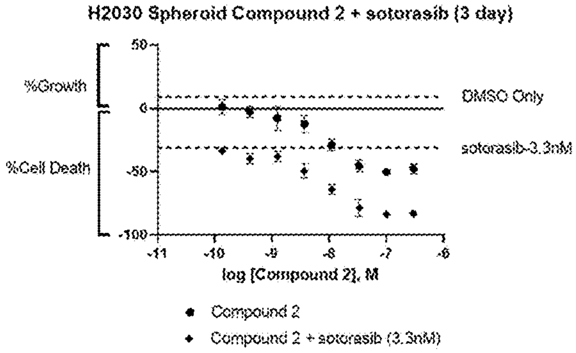
FIGS. 12A, 12B, and 12C illustrate effects of Compound 2 in combination with standard of care agents for inhibition of spheroid growth.
Figure 12B:
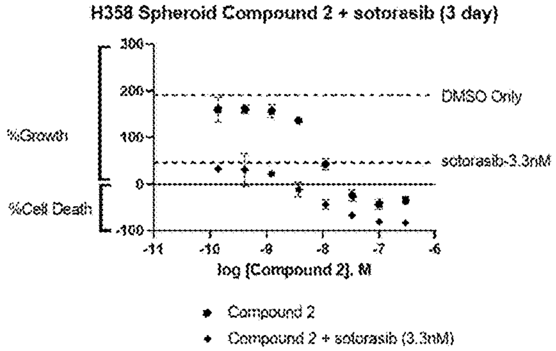
Figure 12C:
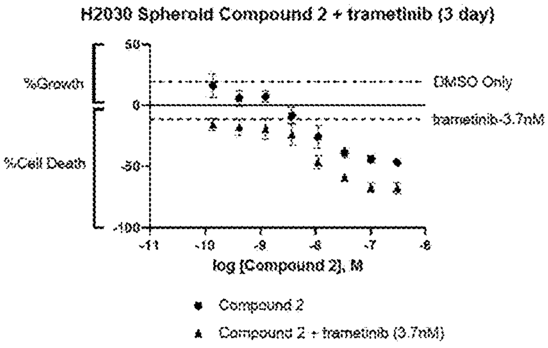

In FIGS. 12A, 12B, and 12C, Compound 2, in combination with standard of care (SOC) agents exhibited additivity or synergy for inhibition of spheroid growth. Representative graphs are shown in FIGS. 12A, 12B, and 12C. FIG. 12A represents a cell proliferation experiment of H2030 NSCLC spheroids treated with Compound 2 titer in combination with 3.3 nM sotorasib (diamonds) or without sotorasib (circles) for 96 h. FIG. 12B represents a cell proliferation experiment of H358 NSCLC spheroids treated with Compound 2 titer in combination with 3.3 nM sotorasib (diamonds) or without sotorasib (circles) for 96 h. FIG. 12C represents a cell proliferation experiment of H2030 NSCLC spheroids treated with Compound 2 titer in combination with 3.7 nM trametinib (triangles) or without trametinib (circles) for 96 h. In all three experiments the combination treatment resulted in greater spheroid regression compared to either single agent.

Example 47. HT-1080 shRNA Knockdown Assay

Fibrosarcoma cell line HT-1080 (catalog #CRL-5807) was obtained from the American Type Culture Collect (ATTC, Manassas, VA). Cells were grown in RPMI-1640 medium supplemented with 10% heat-inactivated fetal bovine serum and 1% Penicillin/Streptomycin/L-Glutamine (Invitrogen, Carlsbad, CA) at 37° C., 5% $CO_2$, and 95% humidity and maintained at 50-80% confluency until use. shRNAs-expressing constructs targeting PERK, GCN2 or scrambled control were obtained from MISSION (Sigma, St. Louis, MO) and lentiviruses containing each construct were produced in-house. Cells were plated at 400,000 cells/well in 6-well tissue culture plates (ThermoFisher Scientific, Waltham, MA) with complete growth media and incubated overnight at 37° C., 5% $CO_2$, and 95% humidity to attach. The next day, existing media was removed from each well and replenished with 1 mL/well fresh media containing 5 μg/mL polybrene (VectorBuilder, Chicago, IL). Cells were transduced with 200 μL/well corresponding lentivirus for 24 hours before being processed for western blot and cell proliferation assays.

Figure 13A:
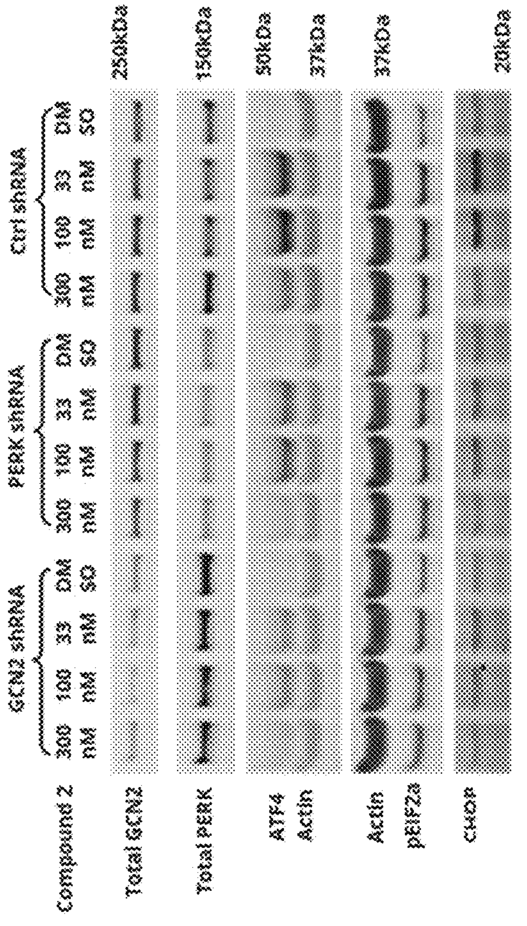
FIGS. 13A, 13B, and 13C show effects of Compound 2 in HT-1080 shRNA knockdown assay.
Figure 13B:
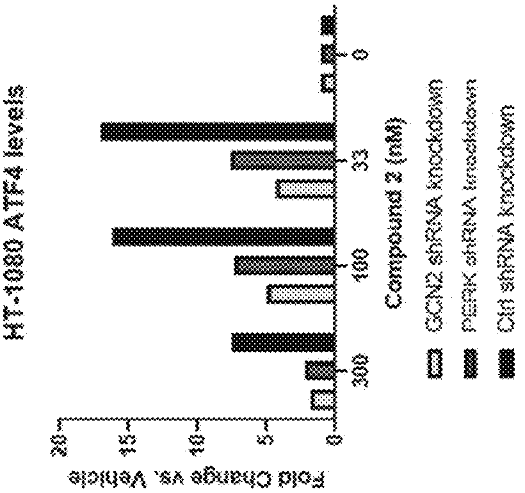
Figure 13C:
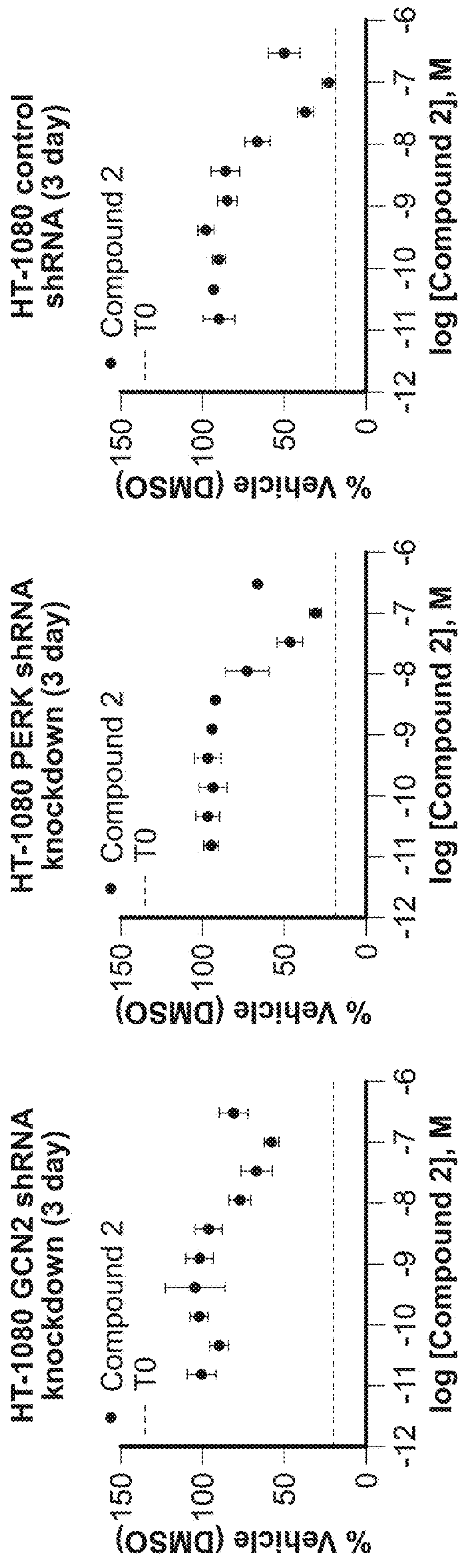

In FIG. 13A, total GCN2 was knocked down by 57% using targeting shRNAs in the HT-1080 cell line. PERK was knocked down by 65% using targeting shRNAs in the HT-1080 cell line. Compound 2-mediated upregulation of ISR markers (ATF4, pEIF2α and CHOP) was downregulated upon knockdown of GCN2 or PERK. FIG. 13B represents Western blot quantification of ATF4 signal. Compound 2 mediated upregulation of ATF4 was reduced by 75% upon knockdown of GCN2. Compound 2 mediated upregulation of ATF4 was reduced by 50% upon knockdown of PERK. In FIG. 13C, Compound 2-mediated spheroid growth inhibition was attenuated upon knockdown of GCN2 but not PERK in this solid tumor cell line.

Example 48. HT-1080 Fibrosarcoma Xenograft Pharmacokinetic/Pharmacodynamic (PK/PD) Model The HT-1080 xenograft model was performed in compliance with all the laws, regulations and guidelines of the National Institutes of Health (NIH) and with the approval of the Animal Care and Use Committee of Labcorp (Ann Arbor, MI), an AAALAC accredited facility. Food and water were provided ad libitum. All mice were observed for clinical signs at least once daily. Female nude mice (6-7 weeks old) were inoculated subcutaneously just below the right high axilla with two million cells in Dulbecco's Phosphate Buffered Saline, using a 27-gauge needle and syringe. When tumor burdens reached 150 mm 3 on average on day 6, mice were randomly assigned into groups such that the mean tumor burden for all groups was within 10% of the overall mean tumor burden for the study population. Groups were treated on days 6-11 as follows: vehicle control (dosed orally) (n=9); Compound 2 dosed orally at 10 mg/kg BID (n=9); Compound 2 dosed orally at 5 mg/kg BID; Compound 2 dosed orally at 1 mg/kg BID (n=9) prior to sample harvest at 2, 6 and 10 h post dose on day 11. Blood samples were collected in K2EDTA tubes and processed into plasma, snap frozen in liquid nitrogen then stored at −80° C. Plasma samples were subjected to pharmacokinetic analysis using liquid chromatography coupled with tandem mass spectrometry analysis (Cayman Chemical, Ann Arbor, MI). Tumors were harvested and powdered over liquid nitrogen in covaris bags and stored at −80° C. For tissue sample processing roughly 30 mg of tumor tissue was lysed in MPER lysis buffer (Thermo Fisher Scientific, Waltham, MA) supplemented with 3× Halt protease inhibitor, 3× Halt phosphatase inhibitor, 3× Sigma phosphatase inhibitor cocktail 2 and 3×EDTA on ice then homogenized using Bead Ruptor 96 (Omni, Kennesaw, GA). Samples were then centrifuged at 21,000 g for 10 min at 4° C. Cleared lysates were then transferred to ice-chilled conical bottom 96-well plates, sealed then stored at −80° C. The next day, samples were thawed on ice followed by centrifugation at 3739 g for 10 min at 4° C. Cleared lysates were then transferred to ice-chilled round bottom 96-well plates. Protein concentrations were determined using BCA protein assay kit (Thermo Fisher Scientific, Waltham, MA). Lysates were normalized to 10 μg/μL prior to boiling in 4×SDS-sample buffer and reducing agent. Samples were resolved using SDS-PAGE then analyzed using Western blot to quantify ATF4 and beta-Actin (Cell Signaling Technology, Danvers, MA). Membranes were imaged with LI-COR Odyssey CLx Imaging System (LI-COR, Lincoln, NE). Data was analyzed using GraphPad Prism software (GraphPad, San Diego, CA) to calculate % inhibition.

Figures 14A, 14B:
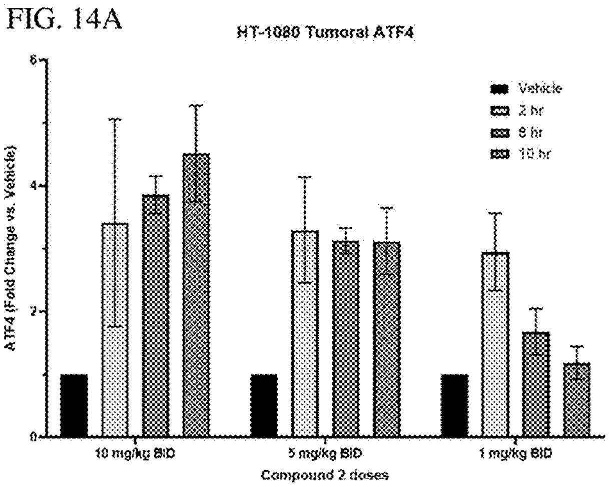
FIGS. 14A and 14B show effects of Compound 2 in HT-1080 fibrosarcoma xenograft PK/PD model.

In FIGS. 14 and 14B, Compound 2 upregulated ATF4 levels in an HT-1080 fibrosarcoma PK/PD xenograft model. As shown in FIG. 14A, Compound 2 upregulated ATF4 levels by 4.5-fold compared to vehicle control when dosed at 10 mg/kg BID orally, upregulated ATF4 levels by 3.5-fold compared to vehicle control when dosed at 5 mg/kg BID orally, and upregulated ATF4 levels by 3-fold compared to vehicle control when dosed at 1 mg/kg BID orally. Corresponding plasma levels of Compound 2 were determined at the PD time points of 2, 6, and 10 hours post dose (FIG. 14B).

Example 49. LoVo Xenograft Efficacy Model

The LoVo xenograft model was performed in compliance with all the laws, regulations and guidelines of the National Institutes of Health (NIH) and with the approval of the Animal Care and Use Committee of Crown Bioscience (Taicang, China), an AAALAC accredited facility. Food and water were provided ad libitum. All mice were observed for clinical signs at least once daily. Female Balb/c nude mice (5-9 weeks old) were inoculated subcutaneously just below the right high axilla with ten million cells in Dulbecco's Phosphate Buffered Saline, using a 27-gauge needle and syringe. When tumor burdens reached 100 mm 3 on average on day 6, mice were randomly assigned into groups such that the mean tumor burden for all groups was within 10% of the overall mean tumor burden for the study population. Groups were treated on days 6-27 as follows: vehicle control (dosed orally) (n=9); Compound 2 dosed orally at 5 mg/kg BID (n=9); Compound 2 dosed orally at 1 mg/kg BID. Tumor volume and body weights were measured three time per week. Tumor burden (mg) was estimated from caliper measurements by the formula: tumor burden (mg=mm 3)=(length×width$^2$)/2.

Example 50. HT-1080 Xenograft Efficacy Model

The HT-1080 xenograft model was performed in compliance with all the laws, regulations and guidelines of the National Institutes of Health (NIH) and with the approval of the Animal Care and Use Committee of Labcorp (Ann Arbor, MI), an AAALAC accredited facility. Food and water were provided ad libitum. All mice were observed for clinical signs at least once daily. Female nude mice (6-7 weeks old) were inoculated subcutaneously just below the right high axilla with two million cells in Dulbecco's Phosphate Buffered Saline, using a 27-gauge needle and syringe. When tumor burdens reached 100 mm 3 on average on day 6, mice were randomly assigned into groups such that the mean tumor burden for all groups was within 10% of the overall mean tumor burden for the study population. Groups were treated on days 6-14 as follows: vehicle control (dosed orally) (n=9); Compound 2 dosed orally at mg/kg BID (n=9); Compound 2 dosed orally at 5 mg/kg BID. Tumor volume and body weight were measured three time per week. Tumor burden (mg) was estimated from caliper measurements by the formula: tumor burden (mg=mm 3)=(length×width$^2$)/2.

Figure 15A:
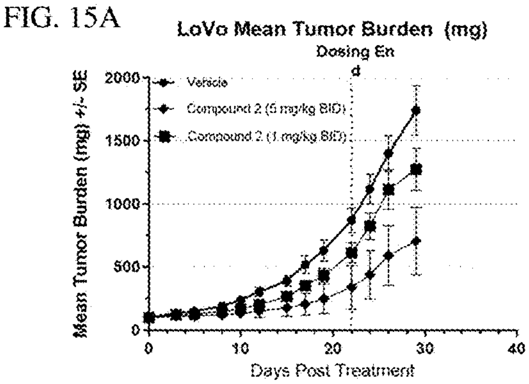
FIGS. 15A and 15B illustrate effects of Compound 2 in HT-1080 xenograft efficacy model.
Figure 15B:
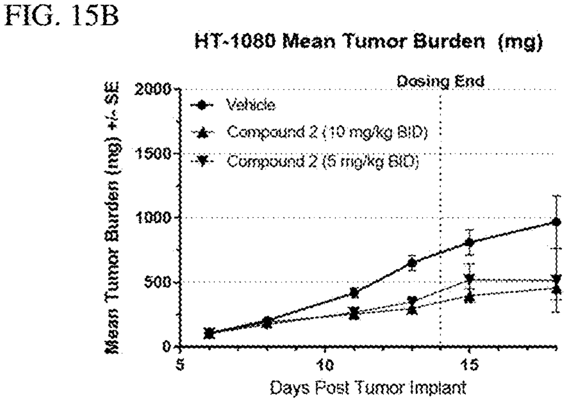

As shown in FIG. 15A, Compound 2 inhibited tumor growth in the LoVo colorectal xenograft model. The mean tumor growth inhibition was 69% after 22 days of dosing Compound 2 at 5 mg/kg BID. FIG. 15B, Compound 2 inhibited tumor growth of the HT-1080 fibrosarcoma xenograft model. The mean tumor growth inhibition was 50% after 14 days of dosing Compound 2 at 10 mg/kg BID.

EQUIVALENTS

While specific embodiments have been discussed, the above specification is illustrative and not restrictive. Many variations of the embodiments will become apparent to those skilled in the art upon review of this specification. The full scope of what is disclosed should be determined by reference to the claims, along with their full scope of equivalents, and the specification, along with such variations.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained.

What is claimed is:

1. A compound represented by Formula I-A:

Formula I-A

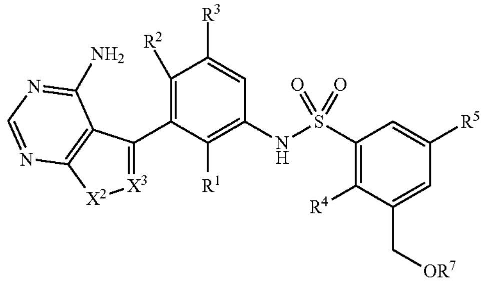

or a pharmaceutically acceptable salt, enantiomer, stereoisomer, or tautomer thereof, wherein:

$X^1$ and $X^3$ are each independently selected from the group consisting of CH and N;

$X^2$ is selected from the group consisting of $NR^6$, O, and S;

$R^1$, $R^2$, and $R^3$ are each independently selected from the group consisting of H, halogen, cyano, and alkoxy;

$R^4$ is selected from the group consisting of halogen, alkoxy and alkyl;

$R^5$ is selected from the group consisting of H, halogen and alkyl;

$R^6$ is selected from the group consisting of H, alkyl, alkenyl, alkenylalkyl, alkynyl, alkynylalkyl, cycloalkyl, cycloalkylalkyl, alkoxyalkyl, cycloalkenyl, heterocyclyl, heterocyclylalkyl, aryl, heteroaryl, and heteroarylalkyl; and $R^7$ is selected from the group consisting of H, alkyl, and acyl.

2. The compound of claim 1, wherein at least one of $R^1$, $R^2$, and $R^3$ is halogen.

3. The compound of claim 1, wherein at least one of $R^1$, $R^2$, and $R^3$ is fluoro.

4. The compound of claim 1 represented by Formula I-B:

Formula I-B

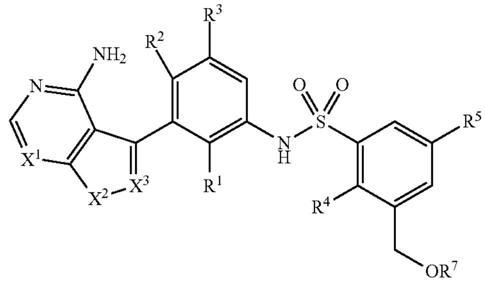

or a pharmaceutically acceptable salt, enantiomer, stereoisomer, or tautomer thereof, wherein:

$X^1$ and $X^3$ are each independently selected from the group consisting of CH and N;

$X^2$ is selected from the group consisting of $NR^6$, O, and S;

$R^2$ and $R^3$ are each independently selected from the group consisting of H, halogen, cyano, and alkoxy;

$R^4$ is selected from the group consisting of halogen, alkoxy and alkyl;

$R^5$ is selected from the group consisting of H, halogen and alkyl;

$R^6$ is selected from the group consisting of H, alkyl, alkenyl, alkenylalkyl, alkynyl, alkynylalkyl, cycloalkyl, cycloalkylalkyl, alkoxyalkyl, cycloalkenyl, heterocyclyl, heterocyclylalkyl, aryl, heteroaryl, and heteroarylalkyl; and $R^7$ is selected from the group consisting of H, alkyl, and acyl.

5. The compound of claim 1 represented by Formula I-C:

Formula I-C

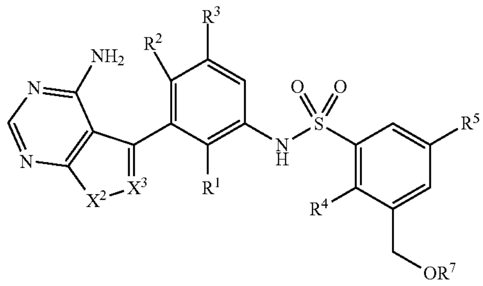

or a pharmaceutically acceptable salt, enantiomer, stereoisomer, or tautomer thereof, wherein:

$X^2$ is selected from the group consisting of $NR^6$, O, and S;

$X^3$ is selected from the group consisting of CH and N;

$R^2$ and $R^3$ are each independently selected from the group consisting of H, halogen, cyano, and alkoxy;

$R^4$ is selected from the group consisting of halogen, alkoxy, and alkyl;

$R^5$ is selected from the group consisting of H, halogen, and alkyl;

$R^6$ is selected from the group consisting of H, alkyl, alkenyl, alkenylalkyl, alkynyl, alkynylalkyl, cycloalkyl, cycloalkylalkyl, alkoxyalkyl, cycloalkenyl, heterocyclyl, heterocyclylalkyl, aryl, heteroaryl, and heteroarylalkyl; and $R^7$ is selected from the group consisting of H, alkyl, and acyl.

6. The compound of claim 1 represented by Formula I-D:

Formula I-D

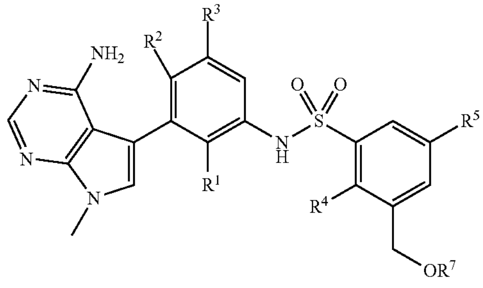

or a pharmaceutically acceptable salt, enantiomer, stereoisomer, or tautomer thereof, wherein:

$R^2$ and $R^3$ are each independently selected from the group consisting of H, halogen, cyano, and alkoxy;

$R^4$ is selected from the group consisting of halogen, alkoxy and alkyl;

$R^5$ is selected from the group consisting of H, halogen and alkyl;

$R^6$ is selected from the group consisting of H, alkyl, alkenyl, alkenylalkyl, alkynyl, alkynylalkyl, cycloalkyl, cycloalkylalkyl, alkoxyalkyl, cycloalkenyl, heterocyclyl, heterocyclylalkyl, aryl, heteroaryl, and heteroarylalkyl; and $R^7$ is selected from the group consisting of H, alkyl, and acetate.

7. The compound of claim 4, wherein $R^2$ is H and $R^3$ is H.

8. The compound of claim 4, wherein $R^2$ is F and $R^3$ is H.

9. The compound of claim 4, wherein $R^2$ is H and $R^3$ is F.

10. The compound of claim 1, wherein $R^6$ is selected from the group consisting of $(C_1-C_8)$alkyl, $(C_2-C_8)$alkenyl, $(C_2-C_8)$alkenyl-$(C_1-C_4)$alkyl, $(C_2-C_8)$alkynyl, $(C_2-C_8)$alkynyl-$(C_1-C_4)$alkyl, $(C_3-C_8)$cycloalkyl, $(C_3-C_8)$cycloalkyl-$(C_1-C_4)$alkyl, $(C_3-C_8)$alkoxy-$(C_1-C_4)$alkyl, $(C_3-C_8)$cycloalkenyl, $(C_3-C_8)$cycloalkenyl-$(C_1-C_4)$alkyl, heterocyclyl, heterocyclyl-$(C_1-C_4)$alkyl, aryl, heteroaryl, and heteroaryl-$(C_1-C_4)$alkyl.

11. The compound of claim 1, wherein $R^6$ is selected from the group consisting of $(C_1-C_8)$alkyl, $(C_3-C_8)$cycloalkyl, $(C_3-C_8)$alkoxy-$(C_1-C_4)$alkyl, heterocyclyl, and heteroaryl.

12. The compound of claim 1, wherein $R^6$ is selected from the group consisting of

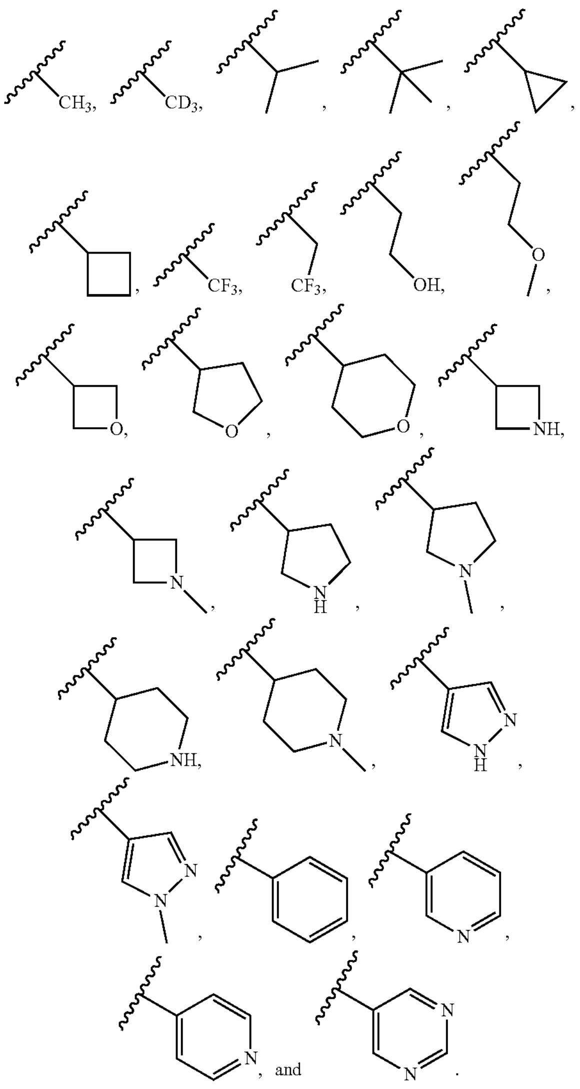

13. The compound of claim 1, wherein $R^4$ is selected from the group consisting of halogen, $(C_1-C_6)$alkoxy and $(C_1-C_6)$alkyl.

14. The compound of claim 1, wherein $R^4$ is selected from the group consisting of chloro, fluoro, methoxy, and methyl.

15. The compound of claim 1, wherein $R^5$ is selected from the group consisting of H, halogen, and $(C_1-C_6)$alkyl.

16. The compound of claim 1, wherein $R^5$ is selected from the group consisting of chloro, fluoro, and methyl.
17. The compound of claim 1, wherein $R^7$ is H.
18. A compound selected from the group consisting of:
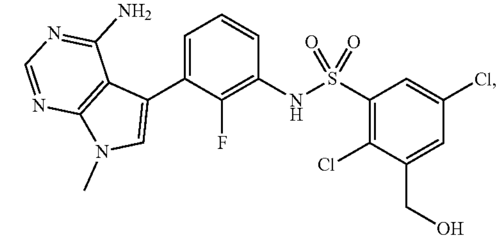
,
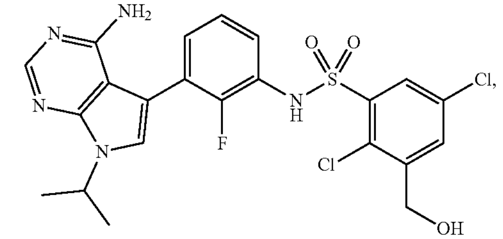
,
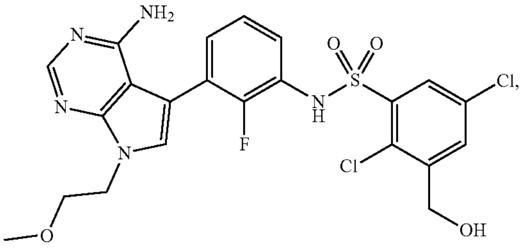
,
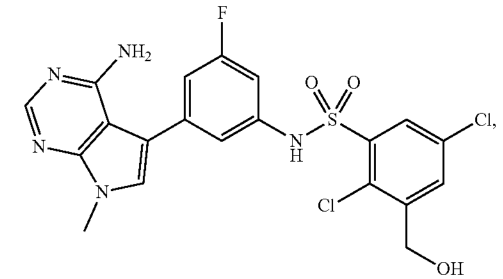
,
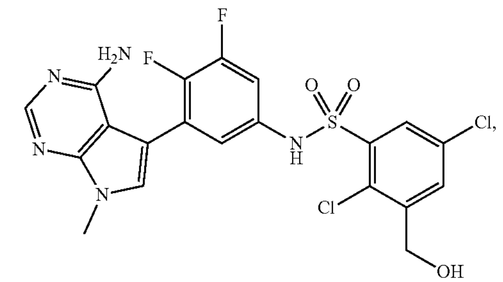
,
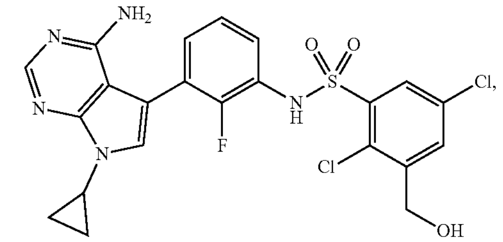
,
-continued
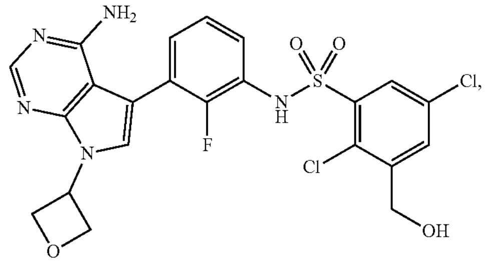
,
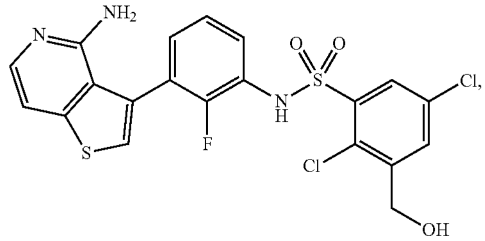
,
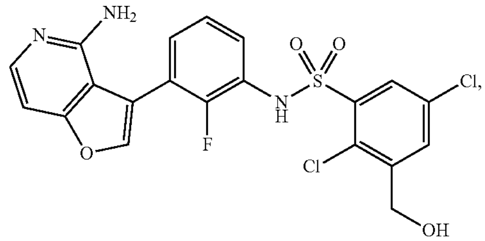
,
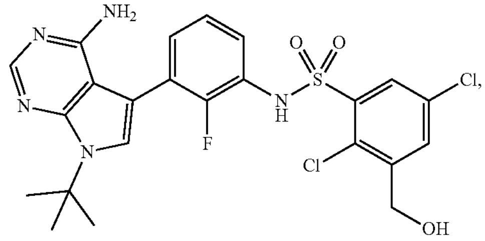
,
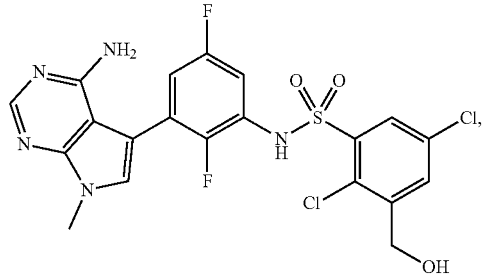
,
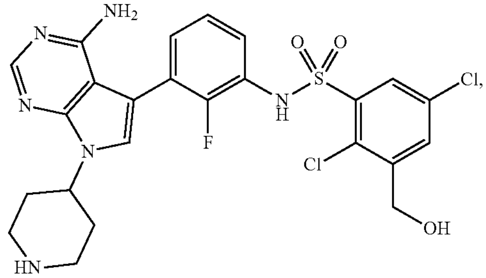
, -continued
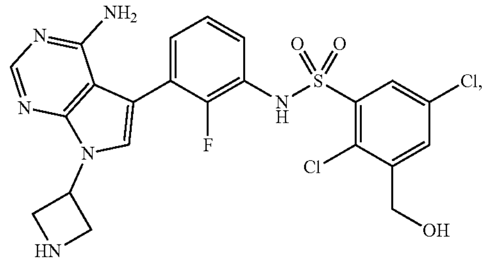
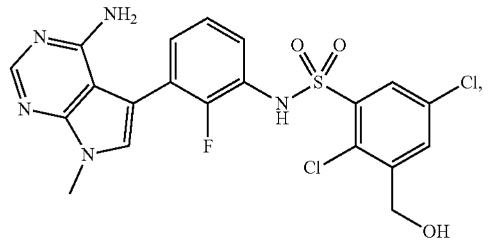
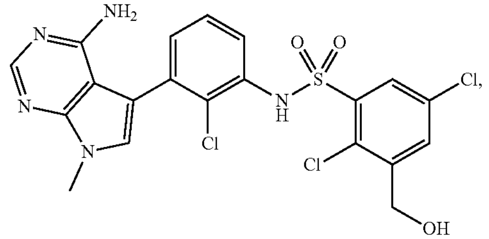
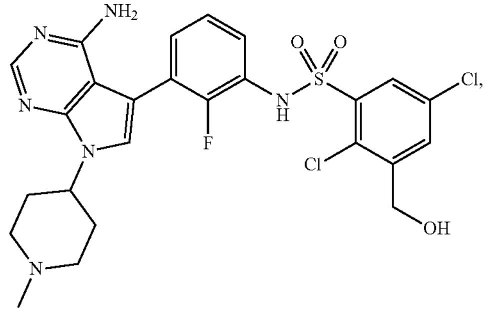
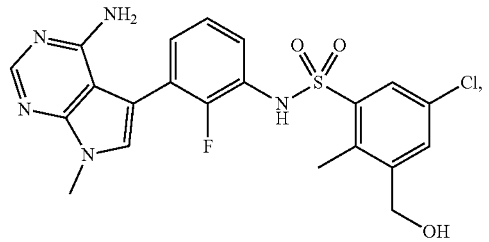
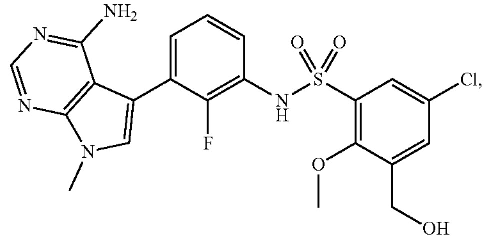
-continued
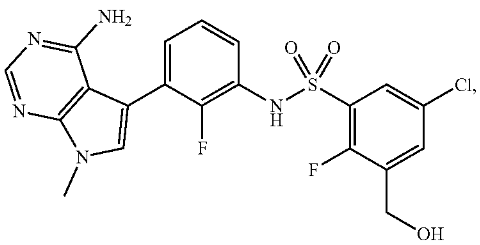
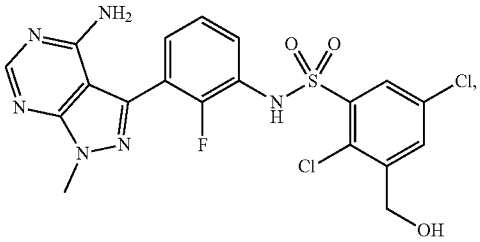
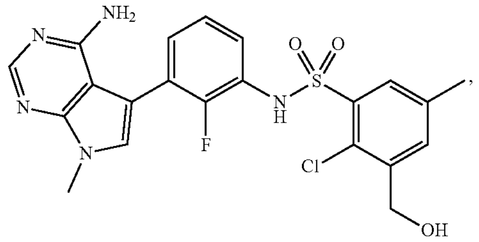
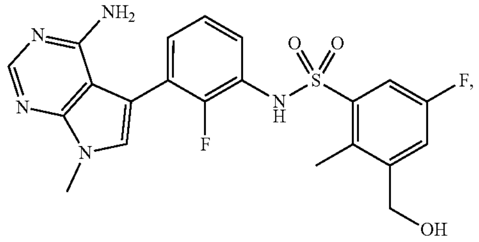
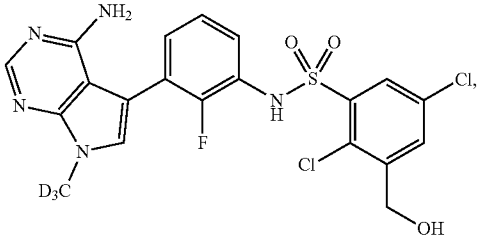
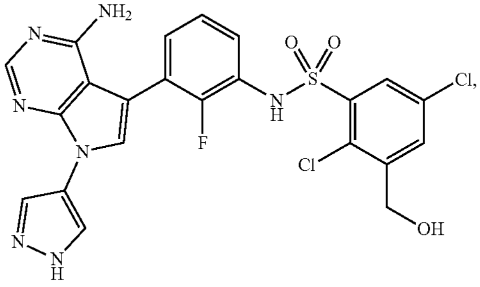

-continued

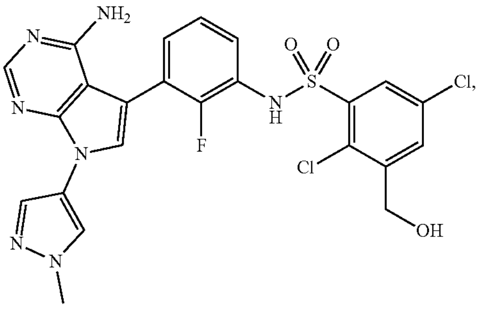

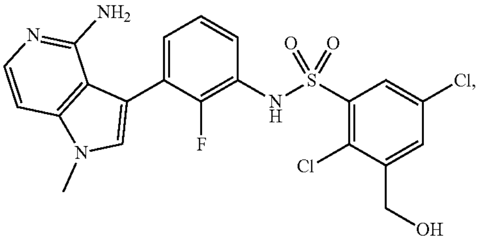

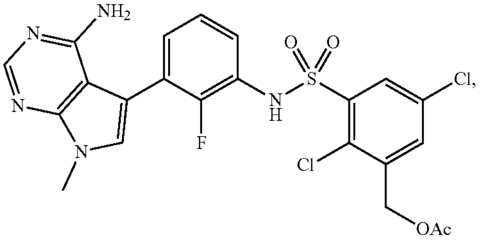

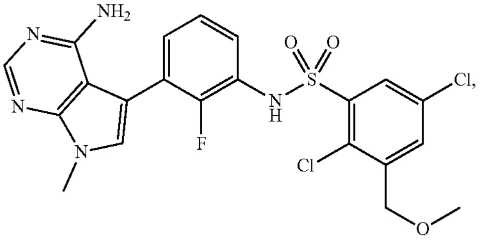

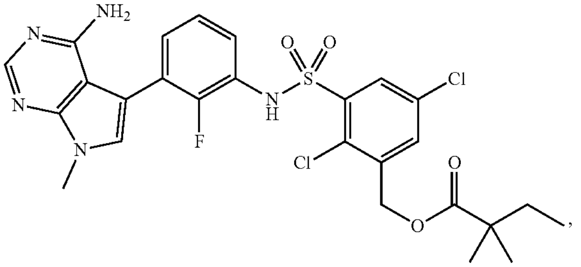

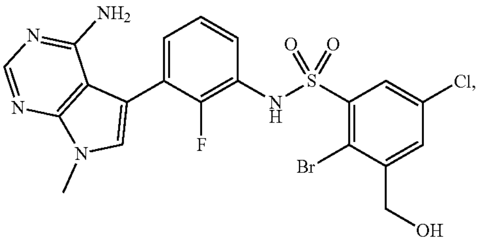

-continued

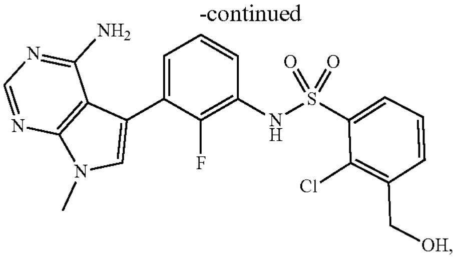

and

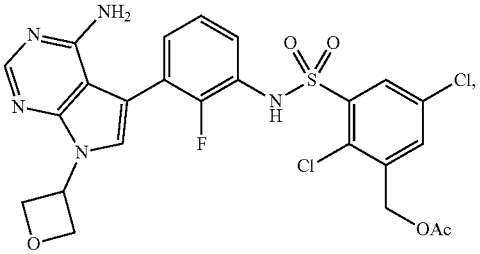

and pharmaceutically acceptable salts, enantiomers, stereoisomers, and tautomers thereof.

19. A pharmaceutical composition comprising a compound according to claim 1, or a pharmaceutically acceptable salt thereof, and a pharmaceutically acceptable carrier or excipient.

20. A method of treating a disease caused by a dysregulation of the integrated stress response in a patient in need thereof, comprising administering to the patient a therapeutically effective amount of the compound of claim 1, or a pharmaceutically acceptable salt thereof.

21. The method of claim 20, wherein the dysregulation of the integrated stress response and/or an unfolded protein response is caused by PERK kinase and/or GCN2 kinase.

22. A method of treating a cancer in a patient in need thereof, comprising administering to the patient a therapeutically effective amount of the compound of claim 1, or a pharmaceutically acceptable salt thereof.

23. The method of claim 22, wherein the cancer is selected from the group consisting of colorectal cancer, lung cancer, mesothelioma, pancreatic cancer, pharyngeal cancer, laryngeal cancer, esophagus cancer, gastric, duodenal cancer, small intestinal cancer, breast cancer, ovarian cancer, testis tumor, prostate, liver cancer, thyroid cancer, renal cancer, uterine cancer, gestational choriocarcinoma, brain tumor, retinoblastoma, skin cancer, melanoma, sarcoma, fibrosarcoma, malignant bone tumor, urinary bladder cancer, hematologic cancer, leukemia, acute myeloid leukemia, acute lymphoblastic leukemia, chronic lymphocytic leukemia, chronic myeloid leukemia, multiple myeloma, B-cell lymphoma, Follicular lymphoma, mantle cell lymphoma, diffuse large B cell lymphoma, T-cell lymphoma, erythroleukemia, histocyctic lymphoma, waldenstrom macroglobulinemia, light chain amyloidosis, and malignant lymphoma.

24. A method of treating a disease selected from a GCN2 associated disease and/or a PERK associated disease, in a patient in need thereof, comprising administering to the patient a therapeutically effective amount of the compound according to claim 1, or a pharmaceutically acceptable salt thereof.

25. The method of claim 24, wherein the disease is a cancer.

26. The method of claim 25, wherein the cancer is selected from the group consisting of colorectal cancer, lung cancer, mesothelioma, pancreatic cancer, pharyngeal cancer, laryngeal cancer, esophagus cancer, gastric, duodenal cancer, small intestinal cancer, breast cancer, ovarian cancer, testis tumor, prostate, liver cancer, thyroid cancer, renal cancer, uterine cancer, gestational choriocarcinoma, brain tumor, retinoblastoma, skin cancer, melanoma, sarcoma, fibrosarcoma, malignant bone tumor, urinary bladder cancer, hematologic cancer, leukemia, acute myeloid leukemia, acute lymphoblastic leukemia, chronic lymphocytic leukemia, chronic myeloid leukemia, multiple myeloma, B-cell lymphoma, Follicular lymphoma, mantle cell lymphoma, diffuse large B cell lymphoma, T-cell lymphoma, erythroleukemia, histocyctic lymphoma, waldenstrom macroglobulinemia, light chain amyloidosis, and malignant lymphoma.

27. The method of claim 24, further comprising administering one or more therapeutic agents, wherein the one or more therapeutic agents is selected from the group consisting of an IMiD agent, a proteasome inhibitor, a steroid, an anti-CD38 agent, an anti-CD20 agent, a Bcl-2 inhibitor, a PI3K inhibitor, a bi-specific antibody, a nucleoside analog, a BTK inhibitor, a DNA alkylating agent, an EZH2 inhibitor, an anthracycline, a topoisomerase inhibitor, a platin, a tyrosine kinase inhibitor, an HDAC inhibitor, a nuclear export inhibitor, an anti-microtubule agent, L-asparaginase, pegylated asparaginase, a PERK inhibitor, a mTOR inhibitor, an immunomodulatory agent, a MAPK pathway inhibitor, a MEK inhibitor, an ERK inhibitor, and a Ras inhibitor.

28. The method of claim 24, further comprising administering one or more therapeutic agents, wherein the one or more therapeutic agents is selected from the group consisting of L-asparaginase, pegaspargase, calaspargase pegol-mnkl, bortezomib, carfilzomib, ixazomib, thalidomide, pomalidomide, lenalidomide, dexamethasone, prednisone, daratumumab, daratumumab/hyaluronidase, isatuximab, rituximab, obinutuzumab, venetoclax, idelalisib, copanlisib, duvelisib, umbralisib, gemcitabine, cytarabine, ibrutinib, acalabrutinib, zanubrutinib, bendamustine, cyclophosphamide, tazemetostat, doxorubicin, daunorubicin, etoposide, oxaloplatin, carboplatin, cisplatin, bosutinib, dasatinib, imatinib, nilotinib, ponatinib, panobinostat, selinexor, vincristine, JZP-458, eryaspase, PF745 (JZP-341), asparaginase *Erwinia chrysanthemi* (crisantaspase), *Escherichia coli* asparaginase (colaspase), an anti-PD1 agent, an anti-PDL1 agent, and an anti-CTLA4 agent.

* * * * *